US008260624B2

(12) United States Patent
Firminger et al.

(10) Patent No.: US 8,260,624 B2
(45) Date of Patent: *Sep. 4, 2012

(54) PERSONALIZED PLAN DEVELOPMENT BASED ON OUTCOME IDENTIFICATION

(75) Inventors: Shawn P. Firminger, Redmond, WA (US); Jason Garms, Redmond, WA (US); Roderick A. Hyde, Redmond, WA (US); Edward K. Y. Jung, Bellevue, WA (US); Chris D. Karkanias, Sammamish, WA (US); Eric C. Leuthardt, St. Louis, MO (US); Royce A. Levien, Lexington, MA (US); Richard T. Lord, Tacoma, WA (US); Robert W. Lord, Seattle, WA (US); Mark A. Malamud, Seattle, WA (US); John D. Rinaldo, Jr., Bellevue, WA (US); Clarence T. Tegreene, Bellevue, WA (US); Kristin M. Tolle, Redmond, WA (US); Lowell L. Wood, Jr., Bellevue, WA (US)

(73) Assignee: The Invention Science Fund I, LLC

( * ) Notice: Subject to any disclaimer, the term of this patent is extended or adjusted under 35 U.S.C. 154(b) by 312 days.

This patent is subject to a terminal disclaimer.

(21) Appl. No.: 12/587,018

(22) Filed: Sep. 29, 2009

(65) Prior Publication Data

US 2011/0055094 A1 Mar. 3, 2011

Related U.S. Application Data

(63) Continuation-in-part of application No. 12/584,489, filed on Sep. 3, 2009, and a continuation-in-part of application No. 12/584,653, filed on Sep. 8, 2009.

(51) Int. Cl.
*G06Q 10/00* (2012.01)
(52) U.S. Cl. .......................................................... 705/1.1
(58) Field of Classification Search .................... None
See application file for complete search history.

(56) References Cited

U.S. PATENT DOCUMENTS

| 4,853,854 A | 8/1989 | Behar et al. |
| 5,961,446 A | 10/1999 | Beller et al. |
| 6,338,044 B1 | 1/2002 | Cook et al. |
| 6,353,447 B1 | 3/2002 | Truluck et al. |

(Continued)

OTHER PUBLICATIONS

Agger, Michael; "Every Day We Write the Book: What would happen if Facebook made its data available for research?"; Slate; bearing date of Nov. 30, 2010; printed on Dec. 10, 2010; pp. 1-3; located at: http://www.slate.com/formatdynamics/CleanPrintProxy.aspx?1292008532368.

(Continued)

*Primary Examiner* — Jonathan Ouellette

(57) ABSTRACT

A computationally implemented method includes, but is not limited to: receiving a request for one or more personalized plans designed to facilitate an end user to achieve one or more target outcomes when one or more emulatable aspects indicated by the one or more personalized plans are emulated, the request identifying the one or more target outcomes; seeking one or more reported aspects that are relevant to achieving the one or more target outcomes in response to receiving the request; and developing the one or more personalized plans based, at least in part, on the seeking. In addition to the foregoing, other method aspects are described in the claims, drawings, and text forming a part of the present disclosure.

42 Claims, 41 Drawing Sheets

U.S. PATENT DOCUMENTS

| | | | |
|---|---|---|---|
| 6,842,604 | B1 | 1/2005 | Cook et al. |
| 7,587,368 | B2 | 9/2009 | Felsher |
| 7,668,735 | B2 | 2/2010 | Grace et al. |
| 7,702,685 | B2 | 4/2010 | Shrufi et al. |
| 7,860,852 | B2 | 12/2010 | Brunner et al. |
| 7,908,182 | B1 | 3/2011 | Gupta |
| 7,959,567 | B2 | 6/2011 | Stivoric et al. |
| 8,005,906 | B2 | 8/2011 | Hayashi et al. |
| 2002/0107707 | A1 | 8/2002 | Naparstek et al. |
| 2004/0015337 | A1* | 1/2004 | Thomas et al. ............... 703/11 |
| 2005/0197553 | A1 | 9/2005 | Cooper |
| 2005/0216300 | A1 | 9/2005 | Appelman et al. |
| 2006/0036619 | A1* | 2/2006 | Fuerst et al. ................ 707/100 |
| 2007/0088576 | A1 | 4/2007 | de Beus et al. |
| 2008/0091471 | A1 | 4/2008 | Michon et al. |
| 2008/0288425 | A1* | 11/2008 | Posse et al. ................ 706/12 |
| 2008/0294012 | A1* | 11/2008 | Kurtz et al. ................ 600/300 |
| 2009/0044113 | A1 | 2/2009 | Jones et al. |
| 2009/0070679 | A1 | 3/2009 | Shen et al. |
| 2009/0075242 | A1 | 3/2009 | Schwarzberg et al. |
| 2009/0076335 | A1 | 3/2009 | Schwarzberg et al. |
| 2009/0100469 | A1 | 4/2009 | Conradt et al. |
| 2009/0176526 | A1* | 7/2009 | Altman .................. 455/556.1 |
| 2009/0258710 | A1* | 10/2009 | Quatrochi et al. ............. 463/43 |
| 2009/0271247 | A1 | 10/2009 | Karelin et al. |
| 2009/0292814 | A1 | 11/2009 | Ting et al. |
| 2009/0299990 | A1* | 12/2009 | Setlur et al. ................ 707/5 |
| 2009/0313041 | A1* | 12/2009 | Eder ........................ 705/2 |
| 2009/0319288 | A1 | 12/2009 | Slaney et al. |
| 2009/0326981 | A1* | 12/2009 | Karkanias et al. ............. 705/3 |
| 2010/0063993 | A1* | 3/2010 | Higgins et al. ............... 709/203 |
| 2010/0114788 | A1 | 5/2010 | White et al. |
| 2010/0268830 | A1 | 10/2010 | McKee et al. |
| 2010/0281364 | A1* | 11/2010 | Sidman .................... 715/713 |
| 2010/0293247 | A1 | 11/2010 | McKee et al. |
| 2010/0305806 | A1* | 12/2010 | Hawley .................... 701/33 |
| 2011/0022602 | A1 | 1/2011 | Luo et al. |
| 2011/0179161 | A1 | 7/2011 | Guy et al. |
| 2011/0185020 | A1 | 7/2011 | Ramamurthy et al. |
| 2011/0252101 | A1* | 10/2011 | Davis et al. ................ 709/206 |

OTHER PUBLICATIONS

"Self-tracking links to get you started"; The Quantified Self: self knowledge through numbers; printed on Dec. 10, 2010; pp. 1-5; located at: http://quantifiedself.com/self-tracking-links-to-get-you-started/.

"Free Exercise Programs—Workout Routines & Weight Loss Diet Plans"; Freetrainers.com; Bearing dates of 2000-2008; pp. 1-2; located at: http://www.freetrainers.com/FT/jsp/index.jsp; printed on Sep. 2, 2009.

"Your Personalized Development Plan"; Central Michigan University; Bearing a date of 2004; p. 1; located at: http://www.chsbs.cmich.edu/leader_model/dplanintro.htm; printed on Sep. 2, 2009.

U.S. Appl. No. 12/655,582, Firminger et al.
U.S. Appl. No. 12/655,581, Firminger et al.
U.S. Appl. No. 12/655,365, Firminger et al.
U.S. Appl. No. 12/655,250, Firminger et al.
U.S. Appl. No. 12/655,075, Firminger et al.
U.S. Appl. No. 12/653,972, Firminger et al.
U.S. Appl. No. 12/653,387, Firminger et al.
U.S. Appl. No. 12/653,386, Firminger et al.
U.S. Appl. No. 12/653,180, Firminger et al.
U.S. Appl. No. 12/653,117, Firminger et al.
U.S. Appl. No. 12/592,946, Firminger et al.
U.S. Appl. No. 12/592,944, Firminger et al.
U.S. Appl. No. 12/592,548, Firminger et al.
U.S. Appl. No. 12/592,544, Firminger et al.
U.S. Appl. No. 12/592,161, Firminger et al.
U.S. Appl. No. 12/592,075, Firminger et al.
U.S. Appl. No. 12/590,841, Firminger et al.
U.S. Appl. No. 12/590,600, Firminger et al.
U.S. Appl. No. 12/590,039, Firminger et al.
U.S. Appl. No. 12/590,027, Firminger et al.
U.S. Appl. No. 12/587,127, Firminger et al.
U.S. Appl. No. 12/584,653, Firminger et al.
U.S. Appl. No. 12/584,489, Firminger et al.

Chen, Jason; "You Can Soon Track Your Heart Rate with Your iPhone"; Gizmodo; Bearing a date of Oct. 9, 2009; p. 1; Creative Commons License; located at: http://gizmodo.com/5378340/you-can-soon-track-your-heart-rate-with-your-iphone; printed on Oct. 29, 2009.

Diaz, Jesus; "One Day, This Will Be Remembered as the First Real Tricorder"; gizmodo.com; bearing a date of Nov. 12, 2009; pp. 1-2; located at http://gizmodo.com/5403126/one-day-this-will-be-remembered-as-the...; printed on Nov. 25, 2009.

"Exercise Pro Software Active Care Version 5"; BioEX Systems, Inc.; bearing dates of 1995-2009; pp. 1-4; located at http://www.bioexsystems.com/ActiveCare.htm; printed on Dec. 17, 2009.

"Fitbit automatically tracks your fitness & sleep"; fitbit.com; bearing a date of 2009; pp. 1-2; located at http://www.fitbit.com; printed on Oct. 29, 2009.

Gross, Daniel; "A Jewish Mother in Your Cell Phone"; Slate; bearing a date of Nov. 10, 2009; pp. 1-3; located at http://www.slate.com/formatdynamics/CleanPrintProxy.aspx?125919...; printed on Nov. 25, 2009.

Guez, Tomer; "Weight Loss Software, Food Diary, Exercise Tracker, and Medical Diary. 'The Food and Exercise Diary Software Version 6.0'"; bearing a date of Sep. 2009; pp. 1-17; located at http://www.weightlosssoftware.com/?ti=135&wn=2; printed on Dec. 17, 2009.

"Nutrition tracking software is critical for learning about foods and planning meals"; NutriCoach; bearing a date of Mar. 29, 2006; 6 total pgs.; located at http://www.nutricoach.net/diet_software.html; printed on Dec. 17, 2009.

"Nutritionmaker Focus Nutrition Software Motivate—Analyze—Instruct"; BioEX Systems, Inc.; bearing dates of 1995-2009; pp. 1-4; located at http://www.bioexsystems.com/NutritionMakerChiro.htm; printed on Dec. 17, 2009.

"Tired of a stiff neck and shoulders? Ergo Pro Computer Fatigue Software reminds you when to stretch and shows you how"; BioEX Systems, Inc.; bearing dates of 1995-2009; pp. 1-3; located at http://www.bioexsystems.com/ExerciseBreak.htm; printed on Dec. 17, 2009.

"VHI PC-Kits Desktop Edition"; Visual Health Information; pp. 1-2; located at http://www.vhikits.com/products/software/PCKitsDesktop.aspx; printed on Dec. 17, 2009.

Wilson, Mark; "Philips DirectLife Turns Exercise Into a Status Bar"; Gizmodo; Bearing a date of Oct. 21, 2009; pp. 1-2; Creative Commons License; located at: http://gizmodo.com/5386577/philips-directlife-turns-exercise-into-a-status-bar; printed on Oct. 29, 2009.

Gaonkar, Shravan, et al.; "Micro-Blog: Sharing and Querying Content Through Mobile Phones and Social Participation"; MobiSys '08; Jun. 17-20, 2008; pp. 174-186; ACM.

* cited by examiner

US 8,260,624 B2

PERSONALIZED PLAN DEVELOPMENT BASED ON OUTCOME IDENTIFICATION

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 12/584,489, entitled PERSONALIZED PLAN DEVELOPMENT, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 3 Sep. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/584,653, entitled PERSONALIZED PLAN DEVELOPMENT, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 8 Sep. 2009, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

A computationally implemented method includes, but is not limited to receiving a request for one or more personalized plans designed to facilitate an end user to achieve one or more target outcomes when one or more emulatable aspects indicated by the one or more personalized plans are emulated, the request identifying the one or more target outcomes; seeking one or more reported aspects that are relevant to achieving the one or more target outcomes in response to receiving the request; and developing the one or more personalized plans based, at least in part, on the seeking. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

A computationally implemented system includes, but is not limited to: means for receiving a request for one or more personalized plans designed to facilitate an end user to achieve one or more target outcomes when one or more emulatable aspects indicated by the one or more personalized plans are emulated, the request identifying the one or more target outcomes; means for seeking one or more reported aspects that are relevant to achieving the one or more target outcomes in response to receiving the request; and means for developing the one or more personalized plans based, at least in part, on the seeking. In addition to the foregoing, other system aspects are described in the claims, drawings, and text forming a part of the present disclosure.

A computationally implemented system includes, but is not limited to: circuitry for receiving a request for one or more personalized plans designed to facilitate an end user to achieve one or more target outcomes when one or more emulatable aspects indicated by the one or more personalized plans are emulated, the request identifying the one or more target outcomes; circuitry for seeking one or more reported aspects that are relevant to achieving the one or more target outcomes in response to receiving the request and circuitry for developing the one or more personalized plans based, at least in part, on the seeking. In addition to the foregoing, other system aspects are described in the claims, drawings, and text forming a part of the present disclosure.

A computer program product including a signal-bearing medium bearing one or more instructions for receiving a request for one or more personalized plans designed to facilitate an end user to achieve one or more target outcomes when one or more emulatable aspects indicated by the one or more personalized plans are emulated, the request identifying the one or more target outcomes; one or more instructions for seeking one or more reported aspects that are relevant to achieving the one or more target outcomes in response to receiving the request; and one or more instructions for developing the one or more personalized plans based, at least in part, on the seeking. In addition to the foregoing, other computer program product aspects are described in the claims, drawings, and text forming a part of the present disclosure.

A method for developing one or more personalized plans that includes receiving a request for one or more personalized plans designed to facilitate an end user to achieve one or more target outcomes when one or more emulatable aspects indicated by the one or more personalized plans are emulated, the request identifying the one or more target outcomes; seeking, using a microprocessor, one or more reported aspects that are relevant to achieving the one or more target outcomes in response to receiving the request; and developing the one or more personalized plans based, at least in part, on the seeking.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 7l is a high-level logic flowchart of a process depicting alternate implementations of the seeking operation 504 of FIG. 5.

DETAILED DESCRIPTION

Figure 1A:
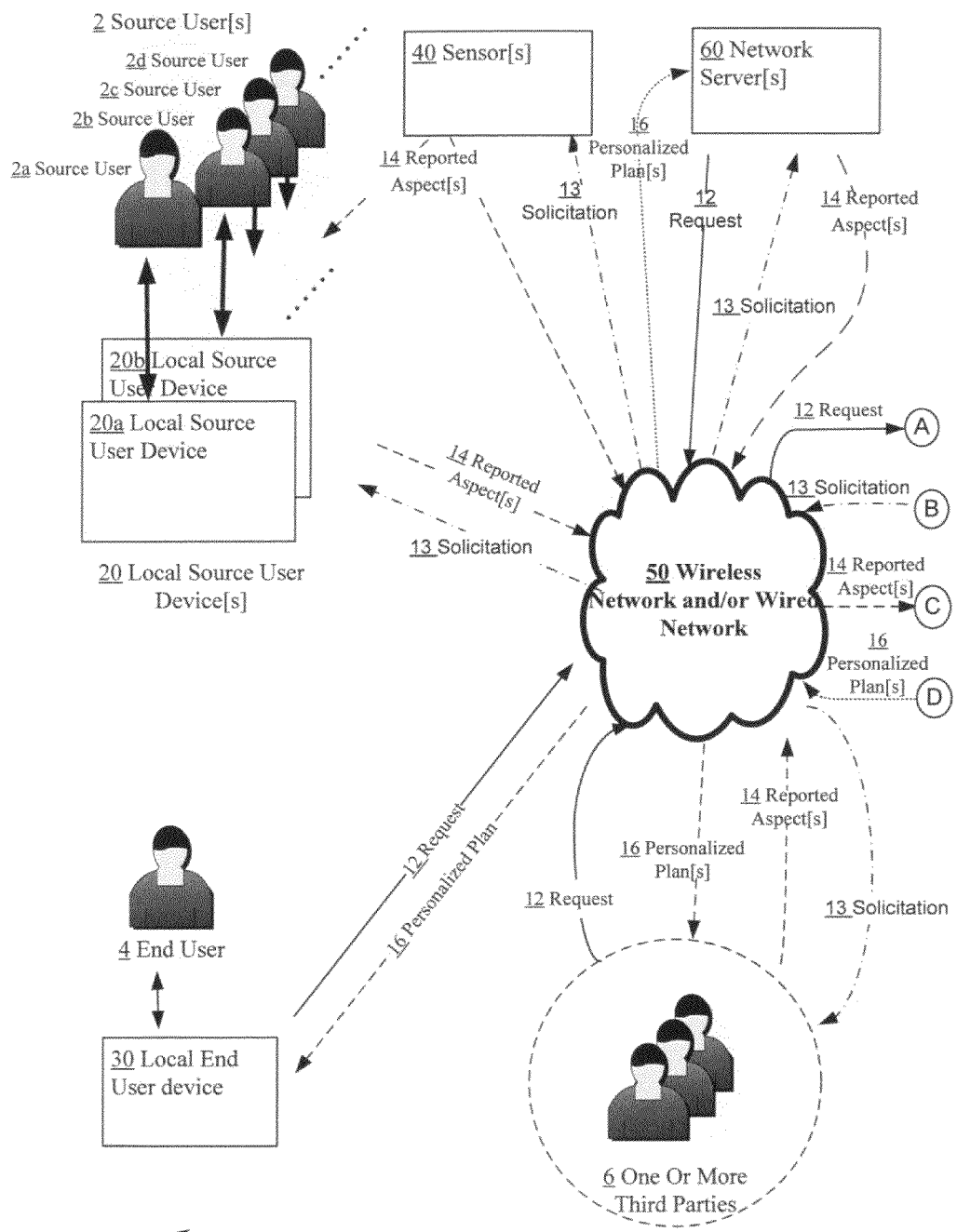
FIGS. 1a and 1b show a high-level block diagram of a server 10 operating in a network environment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

A recent trend that has enjoyed explosive popularity in the computing/communication field is to electronically record one's daily activities, behaviors, thoughts, beliefs, traits, physical or mental states, physical characteristics, and other aspects of the person's everyday life onto an open diary. One place where such open diaries are maintained is at social networking sites commonly known as "blogs" where one or more users may report or post every aspect of their daily lives. The process of reporting or posting blog entries is commonly referred to as blogging. A newer type of blogging that has become very popular is microblogging, otherwise known as "twittering" or "tweeting." In microblogging, each of the microblogs that are posted are typically relatively short posts or entries, usually not more than 140 characters long.

Other types of social networking sites may also allow users to maintain open diaries and to allow users to easily update their personal information. Such updates are typically made via, for example, social networking status reports. These social networking sites allow a user to report or post for others to view the latest status or other aspects related to the user. Although a wealth of personal information in the form of, for example, log data are now available through these social networking sites, it is only recently has there been any effort to exploit such potentially useful data.

In various embodiments, robust methods, systems, circuitry, and computer program products are provided that may facilitate in the development of one or personalized plans designed to facilitate an end user to achieve one or more target outcomes when one or more emulatable aspects indicated by the one or more personalized plans are emulated. The methods, systems, circuitry, and computer program products may be implemented in a variety of computing/communication devices including in a network device such as a server (e.g., network servers) or a local client device. In various embodiments, the development of the one or more personalized plans may be prompted when, for example, a request is received that identifies at least the one or more target outcomes.

In response to receiving the request, the methods, systems, circuitry, and computer program products may be designed to cause at least the execution of an operation to seek one or more reported aspects that are determined to be relevant to achieving the one or more target outcomes. A reported aspect may be any indication (e.g., in the form of electronic data such as text data, numerical data, image data, digital data, analog data, etc.) that indicates a reported occurrence of an aspect (e.g., behavior, act, trait, physical state, mental state, social state, declaration, belief, or any other facet) that may be associated with one or more source users. In some cases, the one or more relevant reported aspects to be found may be found from a plurality of reported aspects that may include both relevant and not relevant reported aspects for achieving the one or more target outcomes. Various locations or sources may be searched in order to find the one or more reported aspects that are relevant to achieving the one or more targeted outcomes in various embodiments. For example, in some embodiments, a memory (e.g., mass storage, volatile memory, non-volatile memory, and so forth) and/or a wireless and/or wired network may be searched for the one or more reported aspects that are relevant to achieving the one or more target outcomes.

Each reported aspect that is found to be relevant to achieving the one or more target outcomes may be associated with one or more source users and may have been at least originally reported by, for example, the one or more source users, one or more sensors, and/or one or more third parties. In some embodiments, a reported aspect may also be associated with a particular point or interval in time and/or associated with a particular location or locations. In certain cases, at least a portion of the one or more reported aspects that have been found to be relevant to the achievement of the one or more target outcomes may have been reported through social networking entries (e.g., microblog entry or status report).

Note that although the request for the one or more personalized plans may indicate the one or more target outcomes, in some embodiments, the request may not indicate any source user. In other embodiments, however, the request for the one or more personalized plans may, in addition to identifying the one or more target outcomes, may identify at least a source user or a group of source users.

Based at least in part on the seeking operations for the one or more reported aspects, the one or more personalized plans may be developed. The development of the one or more personalized plans may be by, for example, including into the one or more personalized plans one or more emulatable aspects that corresponds to the one or more reported aspects that have been determined to be relevant to the achievement of the one or more target outcomes. As will be further described, other types of information may also be included into the one or more personalized plans to be developed in various alternative embodiments.

A number of different approaches may be employed in various embodiments in order to determine whether a reported aspect is relevant to the achievement of one or more target outcomes. For example, in some embodiments, the operation to seek the one or more reported aspects that are relevant to achieving the one or more target outcomes may involve initially seeking one or more reported outcomes (e.g., final outcomes that have been reported) that corresponds to the one or more target outcomes. Note that in some cases a reported outcome may merely be a particular type of reported aspect. For example, if a request has been received for a personalized plan for losing 20 pounds of body weight (e.g., target outcome), a seeking operation may be executed that includes initially searching for one or more reported outcomes or aspects that indicates 20 pounds of body weight loss by one or more source users.

Once the one or more reported outcomes are found that corresponds to the one or more target outcomes, one or more source users may be identified that are associated with the one or more reported outcomes, which corresponds to the one or more target outcomes. By identifying those source users who have achieved the one or more target outcomes (e.g., reported outcomes that corresponds to the target outcomes), the search for the one or more reported aspects that are relevant to achieving the one or more target outcomes may be narrowly focused. The seeking operation may then exam only those reported aspects that are associated with the one or more source users who have been identified as having achieved the one or more target outcomes in order to find the one or more reported aspects that are relevant to achieving the one or more target outcomes.

The seeking operation to seek one or more reported aspects that are relevant to achieving the one or more target outcomes may be further narrowed by seeking or identifying only those reported aspects associated with the one or more identified source users (e.g., source users who have achieved the target outcomes) and that occurred within one or more predefined time periods from the one or more occurrences of the one or more reported outcomes. That is, not all reported aspects associated with the one or more source users previously identified as having achieved the one or more target outcomes may be relevant to the achievement of the one or more target outcomes. This may be particularly true with reported aspects that may have occurred well before (or well after) the achievement of the one or more target outcomes (e.g., as represented by the one or more reported outcomes that have been found to be corresponding to the one or more target outcomes) by the one or more identified source users. Thus, a reported aspect may only be relevant to the achievement of the one or more target outcomes if it falls within some time period (e.g., predefined time period) from the one or more occurrences of the one or more reported outcomes that have been found to be corresponding to the one or more target outcomes. The amount of time period or predefined time period described above may, of course, vary depending on a number of factors.

For example, in some embodiments, the one or more predefined time periods (e.g., each of the one or more target outcomes as represented by the one or more reported outcomes may be associated with a different predefined time period) may be set based on the types of the one or more personalized plans being requested and/or may be provided by the end user, a source user, or some third party. For example, in the above weight loss example, the end user may only be interested in reported aspects (e.g., dietary and/or exercise behaviors) that occurred within one month of the one or more occurrences of the one or more reported outcomes (e.g., body weight loss of 20 pounds). Based on this criteria, only those reported aspects that occurred within one month of the occurrence of the reported target outcome (e.g., 20 pounds of body weight loss) and that are associated with the same one or more source users that were identified as achieving the target outcome may qualify as being relevant to the achievement of the one or more target outcomes. As will be further described herein, other factors (e.g., types of reported aspects that the end user may be interested in or indications provided by one or more third party sources such as publications or research advisories that indicate what types of reported aspects may be relevant to achieving the types of target outcomes being sought) may also determine which reported aspects are "relevant" to achieving the one or more target outcomes.

In some cases, the one or more reported aspects that are found to be relevant to achieving the one or more target outcomes may have been originally acquired in the form of, for example, log data. In some embodiments, such log data may have been at least originally received via social networking entries (e.g., microblog entries and/or status reports), diary entries, sensor readings and/or other means of obtaining log data. Upon finding the one or more reported aspects that are determined to be relevant to achieving the one or more target outcomes, the one or more personalized plans may be developed by including into the one or more personalized plans one or more emulatable aspects that corresponds to the one or more reported aspects that have been found to be relevant to achieving the one or more target outcomes. As will be further described herein, other types of information such as "emulatable intermediate outcomes" may also be included in the one or more personalized plans in various alternative embodiments. After developing the one or more personalized plans, the personalized plans may be presented to the end user or to one or more third parties in various embodiments.

In some embodiments, a personalized plan may merely be a collection of one or more emulatable aspects. An emulatable aspect may be any behavior, act, trait, physical state, mental state, social state, declaration, belief, or any other facet that may be emulated in order to achieve one or more target outcomes. In cases where a personalized plan includes multiple emulatable aspects, the personalized plan may or may not define a relationship or relationships (e.g., temporal, specific time, or spatial relationships) between the emulatable aspects included in the personalized plan. In some cases, a personalized plan may also indicate one or more emulatable intermediate outcomes that may be associated with the target outcomes. For example, if a personalized plan includes a plurality of emulatable aspects, one or more emulatable intermediate outcomes may also be included in the personalized plan that may represent one or more outcomes that preferably or ideally occurs before the target outcome is achieved. In some cases, the emulatable intermediate outcomes that may be included in a personalized plan may be based on, for example, one or more reported intermediate outcomes (e.g., intermediate outcomes that have been reported). By including one or more emulatable intermediate outcomes into a personalized plan, an end user may be able to better monitor his/her progress towards reaching the one or more target outcomes by comparing his/her actual intermediate results with the one or more emulatable intermediate outcomes that may be included in a personalized plan, A "target outcome" may be any type of goal or desired result that may be sought by an end user or by a third party. Examples of target outcomes include, for example, health-related outcomes such as weight loss or improved cardiovascular conditioning, athletic outcomes such as developing a particular athletic skill including being able to pitch a curve ball or achieving a particular golf handicap, physiological outcomes such as reduced blood pressure or blood glucose levels, social outcomes such as obtaining membership into an elite social club or attaining a particular social status, mental state outcomes such as achieving certain level of calmness or happiness, interpersonal or relational outcomes such as having lots of friends or developing skill to make friends, employment outcomes such as being promoted or developing certain work skills, academic or intellectual outcomes, and so forth.

A source user may be any real or fictitious person who may be associated with one or more reported aspects. In some cases, a source user may be an actual person who may be the source or is associated with one or more reported aspects. In other cases, a source user may be a fictional person such as a composite of multiple actual source users. For example, reported aspects of actual aspects associated with a plurality of source user may be compiled and processed (e.g., normalized or averaged out) in order to create such a fictional source user.

Figure 1B:
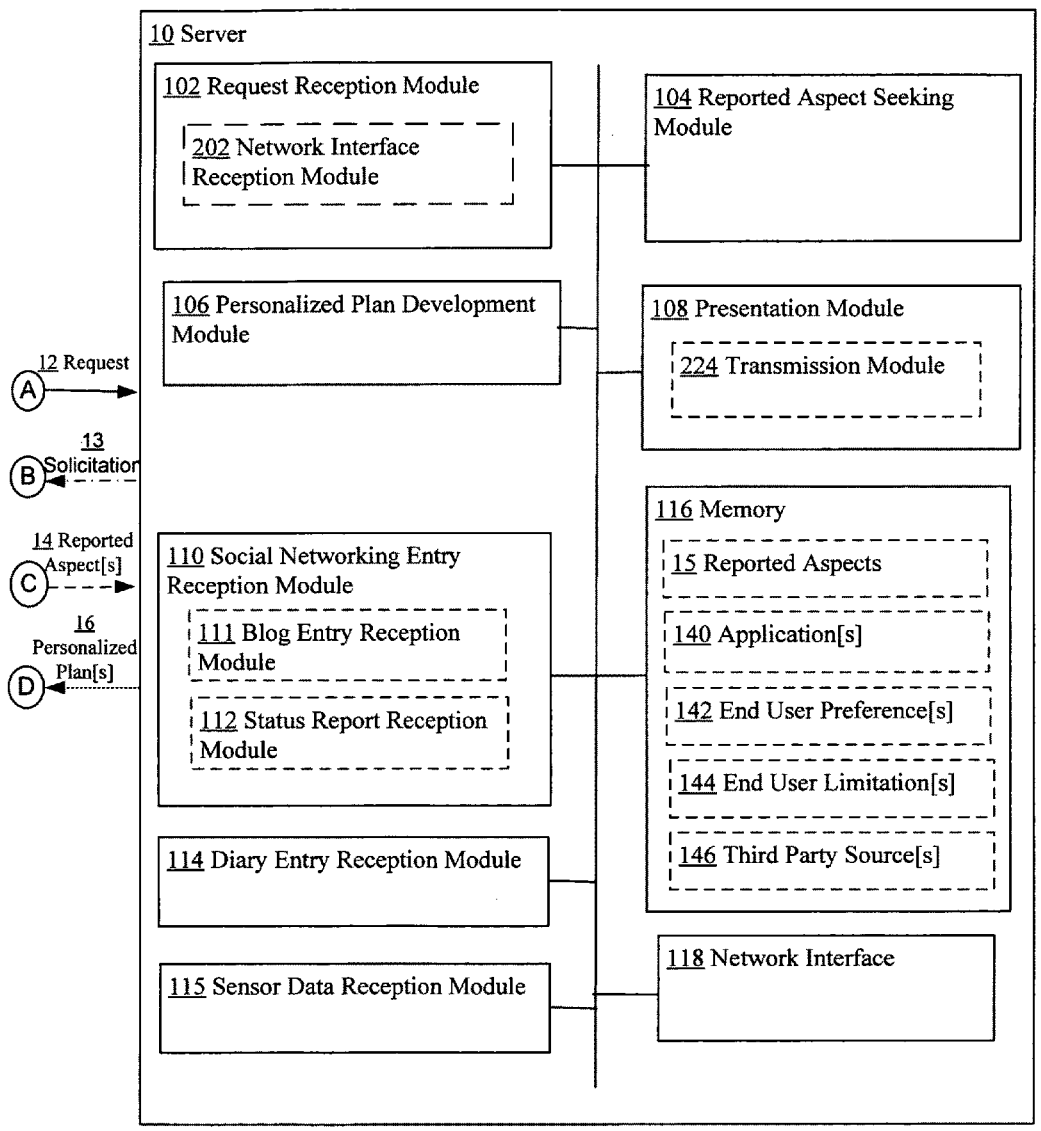
Figure 2A:
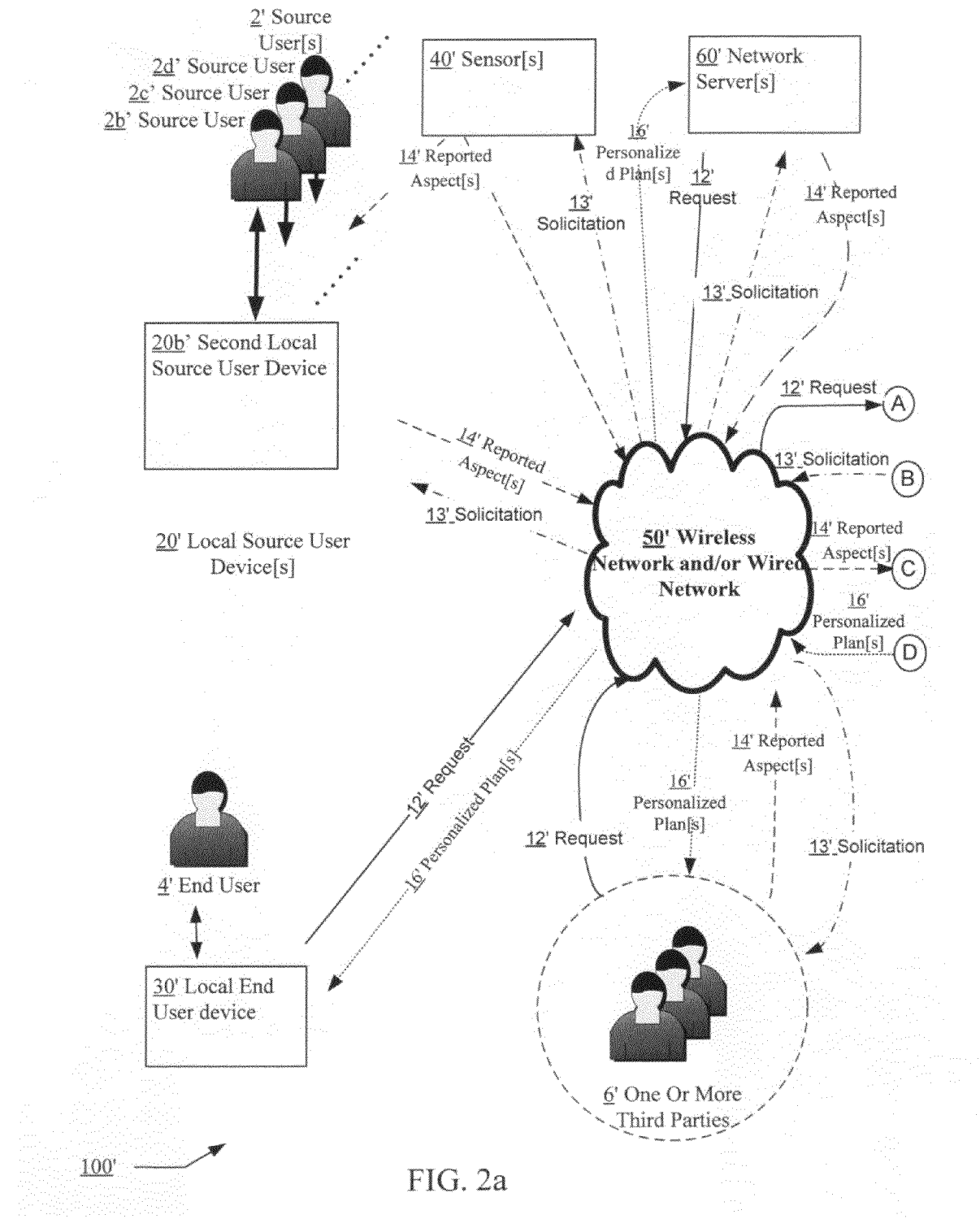
FIGS. 2a and 2b show a high-level block diagram of a local source user device 20' operating in a network environment.
Figure 2B:
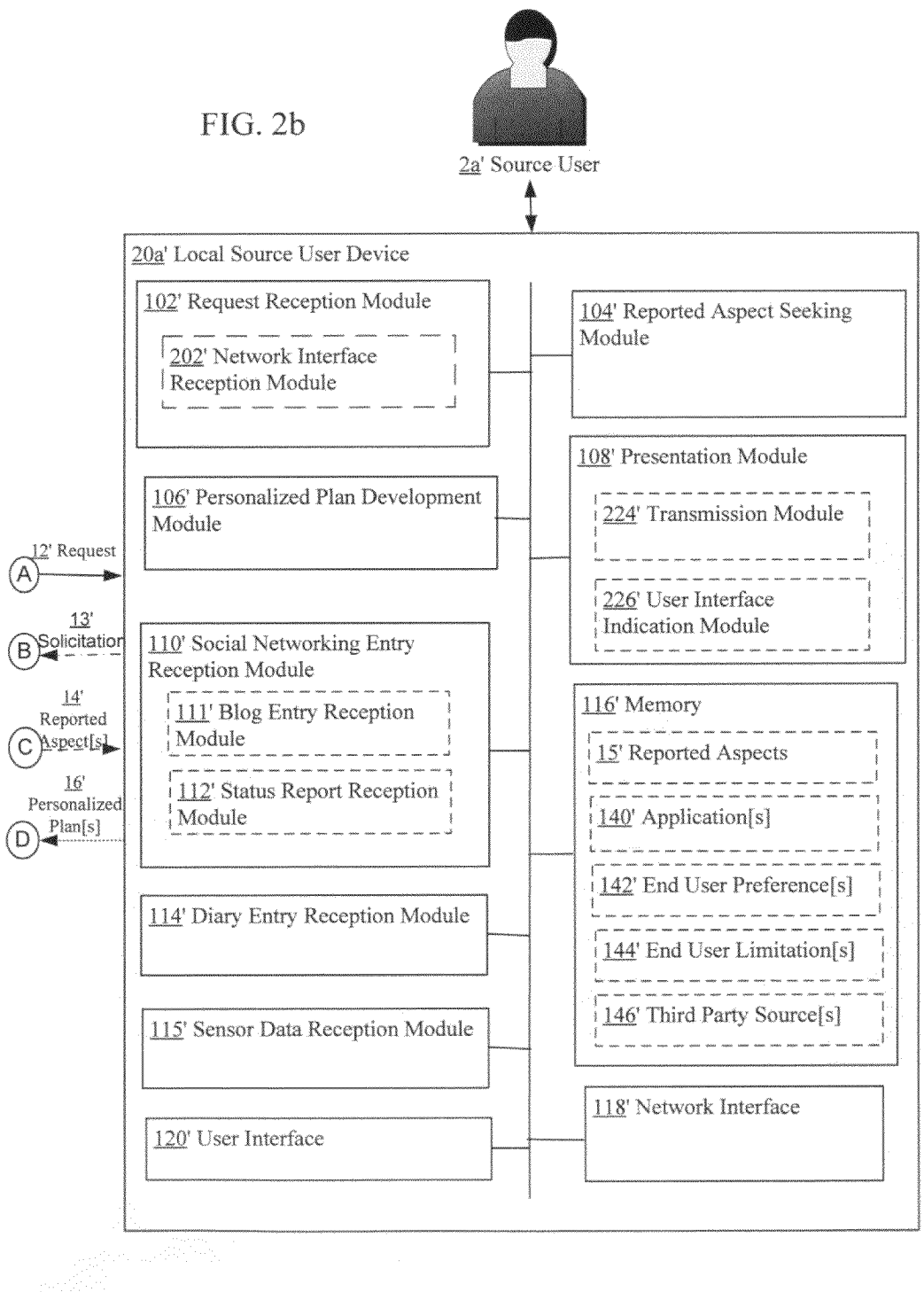
Figure 3A:
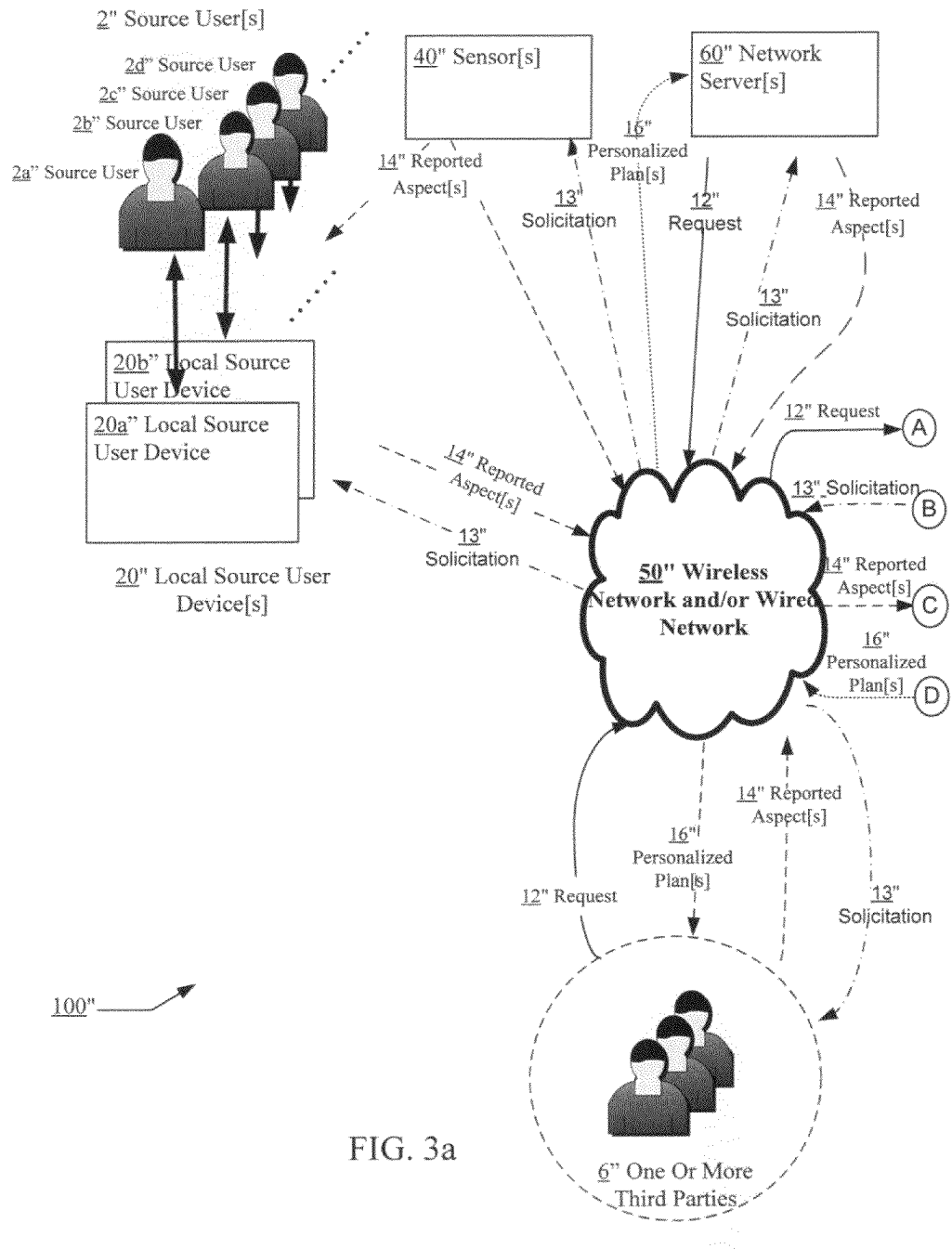
FIGS. 3a and 3b show a high-level block diagram of a local end user device 30" operating in a network environment.
Figure 3B:
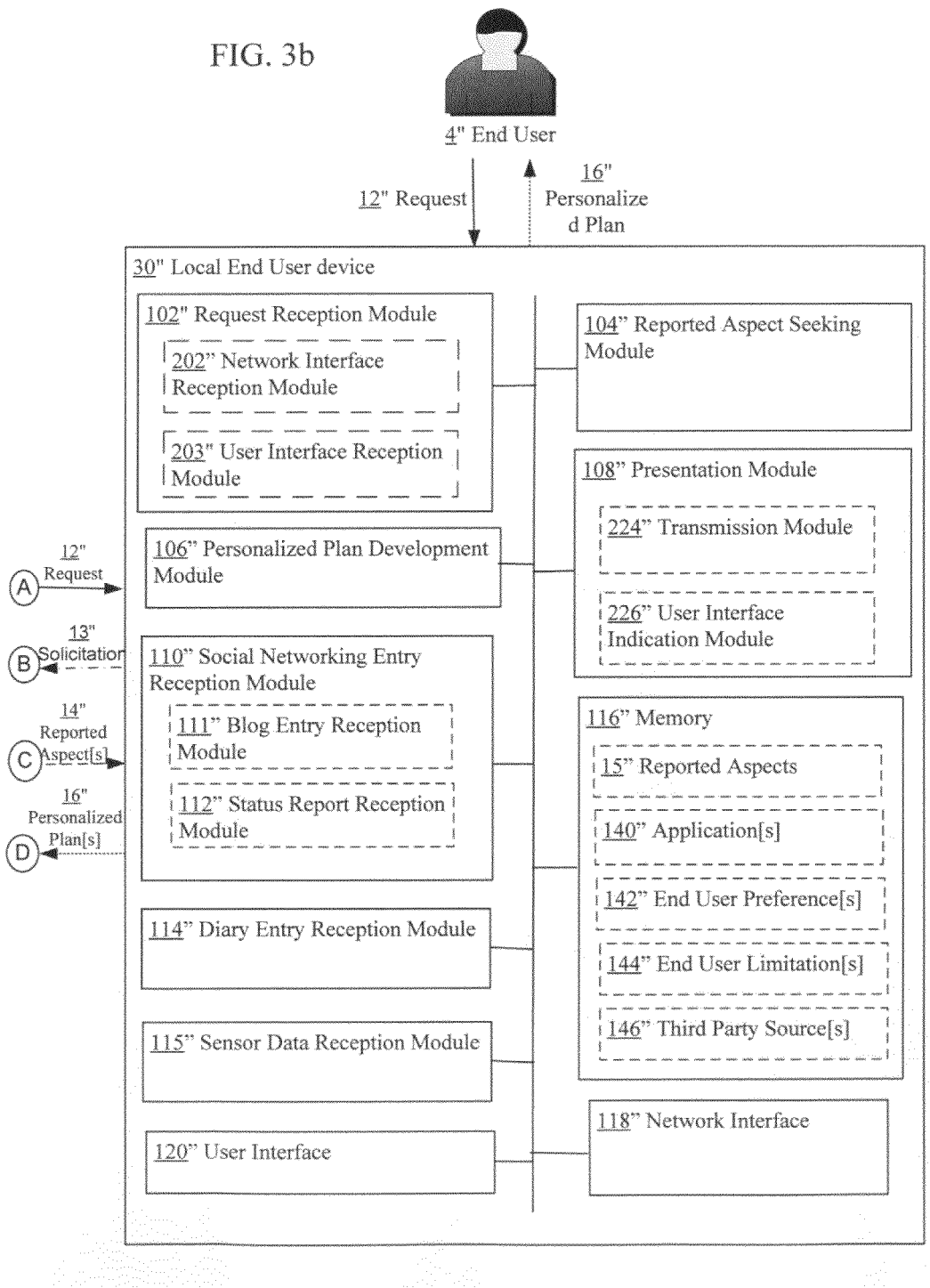

Turning now to FIGS. 1a, 1b, 2a, 2b, 3a, and 3b, illustrating three example environments in which the methods, systems, circuitry, and computer program products in accordance with various embodiments may be implemented by a computing device such as a server or a local client device. In particular, FIGS. 1a and 1b illustrates a first example environment in which the methods, systems, circuitry, and computer program products in accordance with some embodiments may be implemented at a server 10. FIGS. 2a and 2b illustrate a second example environment in which the methods, systems, circuitry, and computer program products in accordance with some embodiments may be implemented at a local source user device 20a'. FIGS. 3a and 3b illustrate a third example environment in which the methods, systems, circuitry, and computer program products in accordance with some embodiments may be implemented at a local end user device 30".

Note that in the following, "*" represents a wildcard. Thus, references in the following description to "one or more source users 2*'" is in reference to the one or more source users 2 of the first example environment of FIGS. 1a and 1b, to the one or more source users 2' of the second example environment of FIGS. 2a and 2b, or to the one or more source users 2" of the third example environment of FIGS. 3a and 3b. Further, references in the following to "a source user 2**" is in reference to any one of the source users (e.g., source user 2a, source user 2b, source user 2a', source user 2b', source user 3a", source user 3b", and so forth) depicted in the three example environments of FIGS. 1a, 1b, 2a, 2b, 3a, and 3b.

In various embodiments, the server 10 of FIG. 1b, the local source user device 20a' of FIG. 1d, and the local end user device 30" of FIG. 1f may be designed to, among other things, receive a request 12* for one or more personalized plans 16* that are designed to facilitate an end user 4* to achieve one or more target outcomes when one or more emulatable aspects indicated by the one or more personalized plans 16* are emulated, the request 12* identifying at least the one or more target outcomes. In some implementations, the request 12* may identify the one or more target outcomes without identifying any source user 2**. In response to the receiving the request 12*, the server 10, the local source user device 20', and the local end user device 30" may be designed to seek (e.g., search or identify) one or more reported aspects 14* that are relevant to achieving the one or more target outcomes. In various implementations, the one or more reported aspects 14* that are found to be relevant to the achievement of the one or more target outcomes may be associated with one or more source users 2* who have achieved the one or more target outcomes.

After seeking for (and finding) the one or more reported aspects 14* that are relevant to achieving the one or more target outcomes, the server 10, the local source user device 20a', and the local end user device 30" may be designed to develop the one or more personalized plans 16* by, for example, including into the one or more personalized plans 16* at least one or more emulatable aspects that corresponds to the one or more reported aspects that were found to be relevant to the achievement of the one or more target outcomes. In some implementations, the server 10, the local source user device 20a', and the local end user device 30" may be further designed to present the resulting one or more personalized plans 16*.

Referring particularly now to FIGS. 1a and 1b illustrated the first example environment in accordance with various embodiments. Included in the illustrated first environment of FIGS. 1a and 1b is a first exemplary system 100, which includes at least a server 10 (see FIG. 1b) that may be designed to communicate with one or more source users 2 (via one or more local source user devices 20) and an end user 4 (via a local end user device 30) through a wireless network and/or wired network 50. In some implementations, the server 10 may further communicate with, via the wireless network and/or wired network 50, one or more third parties 6 (e.g., one or more other end users, one or more content providers, one or more network service providers, and/or one or more other parties), one or more other servers (illustrated as one or more network servers 60), and/or one or more sensors 40.

In various implementations, the server 10 of FIG. 1b (as well as the one or more network servers 60* of FIGS. 1a, 2a, and 3b) may be a computing/communication device that is designed to interface with a wireless network and/or wired network 50. Further, the server 10 of FIG. 1b, as will be described herein, may be in reference to a network server that may be located at a single network site or located across multiple network sites or a conglomeration of servers located at multiple network sites.

The one or more source users 2 may include a first source user 2a, a second source user 2b, a third source user 2c, a fourth source user 2d, and so forth. The one or more local source user devices 20 may include a first local source user device 20a (e.g., to be used by the first source user 2a to communicate via wireless network and/or wired network 50), a second local source user device 20b (e.g., to be used by the second source user 2b to communicate via wireless network and/or wired network 50), and so forth. The one or more local source user devices 20 (as well as the local source user devices 20 of FIGS. 2a and 2b and the one or more local source user devices 20" of FIG. 3a) and the local end user device 30 (as well as the local end user device 30' of FIG. 2a and the local end user device 30" of FIG. 3b) may be any one of a variety of computing/computing devices including, for example, a cellular phone, a personal digital assistant (PDA), a laptop, a desktop, or other types of computing/communication devices. In some embodiments, the one or more local source user devices 20 (as well as the local source user devices 20 of FIGS. 2a and 2b and the one or more local source user devices 20" of FIG. 3a) and/or the local end user device 30 (as well as the local end user device 30' of FIG. 2a and the local end user device 30" of FIG. 2b) may be a handheld device such as a cellular telephone, a smartphone, a Mobile Internet Device (MID), an Ultra Mobile Personal Computer (UMPC), a convergent device such as a personal digital assistant (PDA), and so forth.

In various embodiments, the one or more sensors 40 (as well as the one or more sensors 40' of FIG. 2a and the one or more sensors 40" of FIG. 3a) may include one or more of a wide range of sensing devices that can monitor various aspects or events associated with one or more source users 2. For example, in some implementations, the one or more sensors 40* may include devices that can monitor a user's physiological characteristics such as blood pressure sensors, heart rate monitors, glucometers, and so forth. In some implementations, the one or more sensors 40* may include devices that can monitor activities of a user (e.g., a source user 2*) such as a pedometer, a toilet monitoring system (e.g., to monitor bowel movements), exercise machine sensors, an accelerometer to measure a person's movements which may indicate specific activities, and so forth. The one or more sensors 40* may also include other types of sensor/monitoring devices such as video or digital camera to provide electronic images of, for example, the one or more target outcomes as displayed by a source user 20*, global positioning system (GPS) to provide location data related to a user (e.g., locations of the source user 2*), and so forth. In various implementations, the one or more sensors 40 may be designed to communicate directly with the wireless network and/or wired network 50 or indirectly with the wireless network and/or wired network 50 via the one or more local source user devices 20.

Referring back to the first exemplary environment of FIGS. 1a and 1b, the server 10 may receive a request 12 for one or more personalized plans 16 designed to facilitate an end user 4 to achieve one or more target outcomes from, for example, the end user 4 (e.g., via the local end user device 30), from one or more third parties 6, or from one or more network servers 60. The request 12 may identify at least the one or more target outcomes. In various implementations, the requested one or more personalized plans 16 may be designed to facilitate the end user 4 to achieve the one or more target outcomes when one or more emulatable aspects indicated by the one or more personalized plans 16 are emulated.

In response to receiving the request 12, the server 10 may execute an operation to seek (e.g., identify or search) one or more reported aspects 14 that are relevant to achieving the one or more target outcomes. This may involve searching for the relevant reported aspects 14 at a number of different locations via a wireless network and/or a wired network 50. For example, in some implementations, a solicitation 13 for the one or more reported aspects 14 may be transmitted to one or more local source user devices 20, to one or more third parties 6, to one or more sensors 40, and/or to one or more network servers 60. In alternative or in the same implementations, a memory 116 may be searched for the one or more reported aspects 14. The determination of whether a reported aspect 14 is relevant to the achievement of the one or more target outcomes may be based on a number of factors as will be further described in greater detail herein.

Once the one or more reported aspects 14 relevant to the achievement of the one or more target outcomes have been found, the server 10 may develop the one or more personalized plans 16 by, for example, including into the one or more personalized plans 16, one or more emulatable aspects that corresponds to the reported aspects 14 that have been found to be relevant to the achievement of the one or more target outcomes. In some implementations, a personalized plan 16 may merely be a collection of one or more emulatable aspects, while in other implementations, a personalized plan 16 may define the specific relationships (e.g. spatial or time relationships) between emulatable aspects. In some implementations, a personalized plan 16 may include other information such as emulatable intermediate outcomes to determine, for example, how well an end user 4 when following a personalized plan 16 is progressing towards achieving a target outcome. In some implementations, the server 10 may then be designed to present the developed one or more personalized plans 16 to the end user 4 (via the local end user device 30) and/or to one or more third parties 6.

Figure 4A:
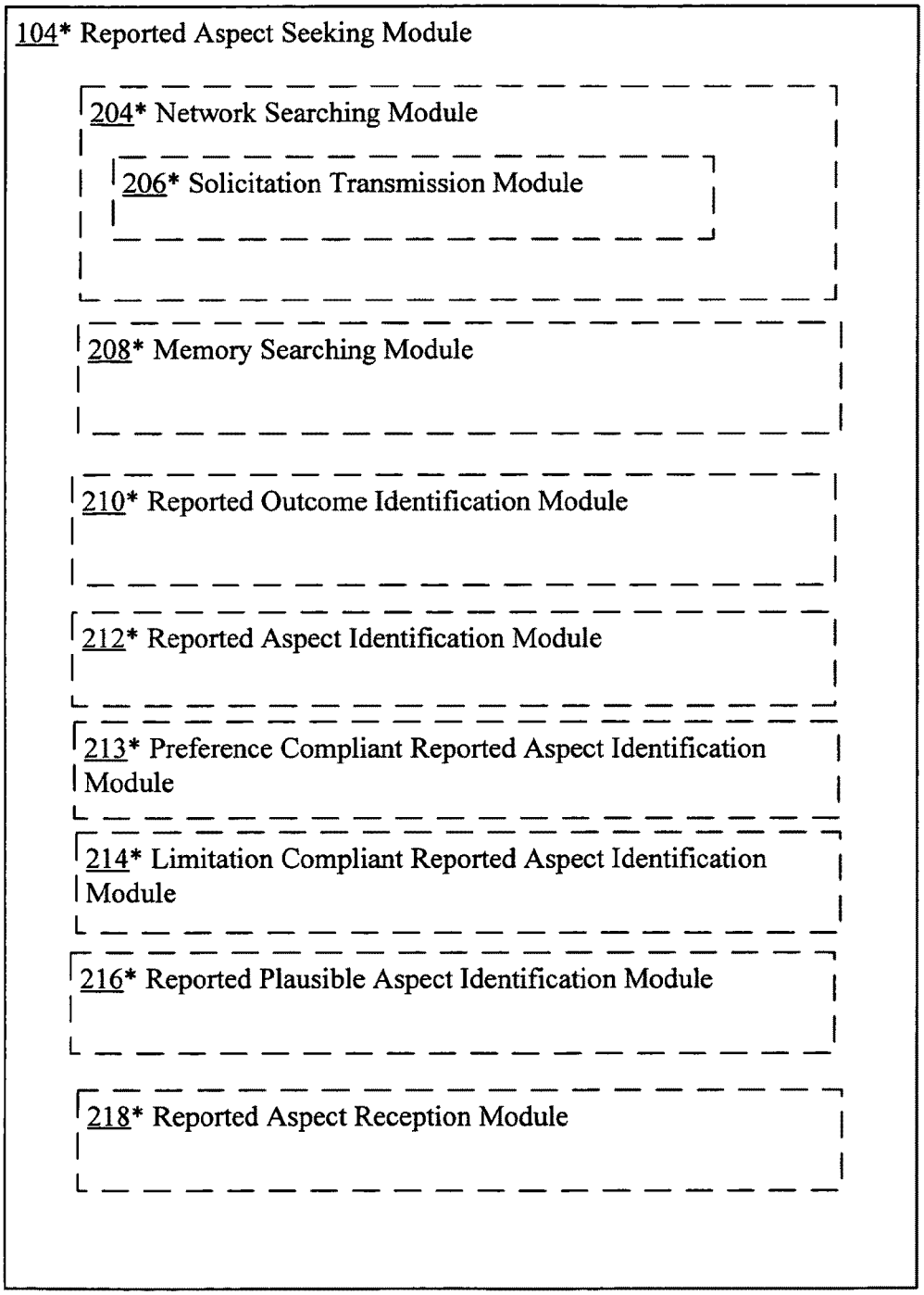
FIG. 4a shows another perspective of the reported aspect seeking module 104* of the server 10 of FIG. 1b, of the local source user device 20' of FIG. 2b, and of the local end user device 30" of FIG. 3b.
Figure 4B:
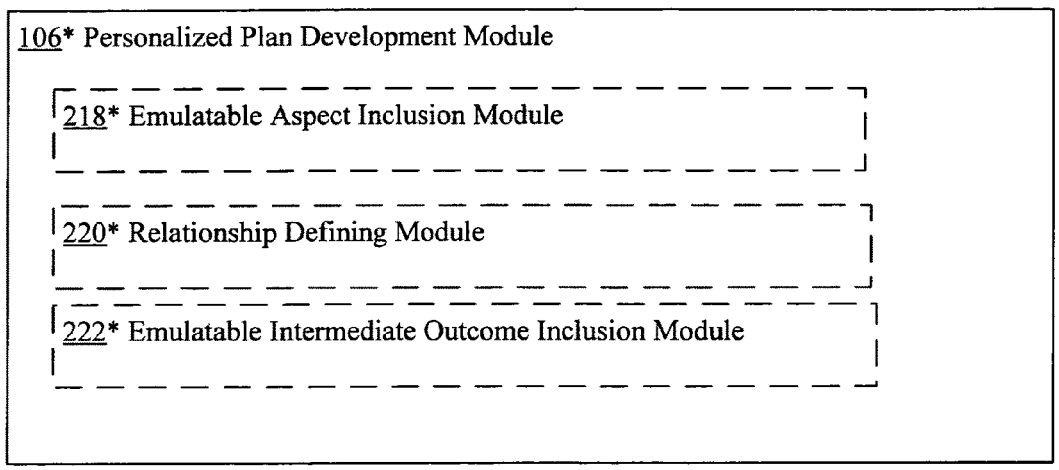
FIG. 4b shows another perspective of the personalized plan development module 106* of the server 10 of FIG. 1b, of the local source user device 20' of FIG. 2b, and of the local end user device 30" of FIG. 3b.

The server 10 as illustrated in FIG. 1b may include a variety of modules, sub-modules, and other components. As shown, the server 10 may include a request reception module 102 (which may further include a network interface reception module 202), a reported aspect seeking module 104 (which may further include one or more sub-modules as illustrated in FIG. 4a), a personalized plan development module 106 (which may further include one or more sub-modules as illustrated in FIG. 4b), a presentation module 108 (which may further include a transmission module 224), a memory 116 (which may store a plurality of reported aspects 15, one or more applications 140, one or more end user preferences 142, one or more end user limitations 144, and/or one or more third party sources 146), and/or a network interface 118 (e.g., a network interface card or NIC). The server 10, in various implementations, may further include a social networking entry reception module 110 (which may further include a blog entry reception module 111 and/or status report reception module 112), a diary entry reception module 114, and/or a sensor data reception module 115.

The request reception module 102 may be configured to, among other things, receive a request 12 for one or more personalized plans 16 that are designed to facilitate an end user 4 to achieve one or more target outcomes when one or more emulatable aspects indicated by the personalized plan 16 are emulated. The request 12 to be received by the request reception module 102 may at least identify the one or more target outcomes. In some implementations, the request 12 to be received by the request reception module 102 may further include other information that may facilitate in the development of the one or more personalized plans 16 as will be further described herein. In order to facilitate reception of a request 12 from, for example, a network device (e.g., local end user device 30 or a network server 60), the request reception module 102 may include a network interface reception module 202 configured to receive the request 12 via a wireless network and/or wired network 50.

The reported aspect seeking module 104 may be configured to seek (e.g., search or identify), in response to the request reception module 102 receiving the request 12, one or more reported aspects 14 that are determined to be relevant to achieving the one or more target outcomes. In various implementations, the reported aspect seeking module 104 may be configured to seek the one or more reported aspects 14 that are relevant to achieving the one or more reported outcomes by transmitting a solicitation for the one or more reported aspects 14 to one or more potential sources (e.g., one or more network servers 60 and/or one or more local source user devices 20) via a wireless network and/or wired network 50. In the same or different implementations, the reported aspect seeking module 104 may be designed to search a memory 116 for the one or more reported aspects 14 that are relevant to achieving the one or more target outcomes. In various implementations, memory 116 may store a plurality of reported aspects 15 that may include both reported aspects 14 that are relevant to the achievement of the one or more target outcomes and reported aspects that are not relevant to achieving the one or more target outcomes. Thus, the reported aspect seeking module 104 may be designed to search or filter through a plurality of reported aspects (e.g., plurality of reported aspects 15 that may be found throughout the wireless network and/or wired network 50 or the plurality of reported aspects 15 that may be included in memory 116) to find the one or more reported aspects 14 that are relevant to the achieving of the one or more target outcomes.

The personalized plan development module 106 may be configured to, among other things, develop one or more personalized plans 16 by, for example, including into the one or more personalized plans 16 at least one or more emulatable aspects that corresponds to the one or more reported aspects 14 found by the reported aspect seeking module 104 that have been determined to be relevant to the achievement of the one or more target outcomes. The personalized plan development module 106 may also be configured to include into the one or more personalized plans 16 other types of information in various alternative implementations. For example, in some implementations, the personalized plan development module 106 may be designed to define in a personalized plan 16 one or more spatial, temporal, or specific time relationships between a plurality of emulatable aspects that may be included in the personalized plan 16. In the same or different implementations, the personalized plan development module 106 may be configured to include into a personalized plan 16 one or more emulatable intermediate outcomes. As will be further described herein, the personalized plan development module 106, in various implementations, may further include one or more sub-modules as will be further described herein and as illustrated in FIG. 4b.

The presentation module 108 may be configured to present the personalized plan 16 developed by the personalized plan development module 106 to the end user 4, one or more source users 2, one or more third parties 6, and/or one or more network servers 60. In some implementations, the presentation module 108 may further include a transmission module 224 that is configured to transmit the one or more personalized plans 16 via, for example, the wireless network and/or wired network 50.

A more detailed discussion relating to the request reception module 102, the reported aspect seeking module 104, the personalized plan development module 106, the presentation module 108, and their sub-modules, will be provided below with respect to the various operational flows to be described herein. The social networking entry reception module 110 may be configured to receive social networking entries from various sources including, for example, one or more source users 2, an end user 4, and/or one or more third parties 6. The social networking entry reception module 110 may further include a blog entry reception module 111 that is configured to receive blog entries (e.g. microblog entries) and/or a status report reception module 112 configured to receive social networking status reports. Similarly, the diary entry reception module 114 may be configured to receive diary entries from, for example, the one or more source users 2, the end user 4, and/or from the one or more third parties 6.

The sensor data reception module 115 may be configured to receive sensing data from one or more sensors 40. The memory 116 may comprise one or more volatile and/or non-volatile devices that may be used to store data. In various implementations, the memory 116 may include, for example, a mass storage device, read-only memory (ROM), programmable read-only memory (PROM), erasable programmable read-only memory (EPROM), cache memory such as random access memory (RAM), flash memory, synchronous random access memory (SRAM), dynamic random access memory (DRAM), and/or other types of memory devices.

In various implementations, memory 116 may store a plurality of reported aspects 15, one or more applications 140, one or more end user preferences 142 (e.g., preferences indicating the types of reported or emulatable aspects that an end user 4 is interested in), one or more end user limitations 144 (e.g., contextual limitations, physical limitations, personal limitations, and so forth that may prevent certain types of aspects from being emulated by, for example, an end user 4), and/or one or more third party sources 146 (e.g., publications, research advisories, and so forth that may indicate the types of reported aspects that may be relevant to achieving one or more target outcomes). The plurality of reported aspects 15 may be associated with one or more source users 2 and may include different types of reported aspects 14 (e.g., behaviors, traits, beliefs, and so forth associated with one or more source users 2). The one or more applications 140 that may be included in the memory 116 may comprise of, for example, one or more communication applications (e.g., text messaging application, instant messaging application, email application, voice recognition system, and so forth), Web 1.0 application, and/or Web 2.0 application to facilitate in communicating via, for example, the World Wide Web.

Referring now to FIGS. 2a and 2b, which as previously indicated, illustrates a second example environment in which the methods, systems, circuitry, and computer program products in accordance with various embodiments may be implemented at a local source user device 20' rather than at a server 10' as was the case in the first example environment of FIGS. 1a and 1b. As illustrated, the second example environment of FIGS. 2a and 2b is similar to the first example environment of FIGS. 1a and 1b.

In general, the second example environment of FIGS. 2a and 2b may include a second exemplary system 100', which includes at least a local source user device 20a' (see FIG. 2b). In various implementations, the local source user device 20a', as was the case for server 10 of FIGS. 1a and 1b, may be designed to receive a request 12' for one or more personalized plans 16' that are designed to facilitate an end user 4' to achieve one or more target outcomes. In some implementations, the request 12' may be received from an end user 4' via a wireless network and/or wired network 50'. Alternatively, the request 12' may be received from a network server 60' or from one or more third parties 6'. As before in the first exemplary environment, the request 12' may identify one or more target outcomes in various implementations. Also as before, in some implementations, the request 12' may not identify any source user 2*'.

In response to receiving the request 12', the local source user device 20a' may be designed to execute an operation to seek (e.g., identify or search) one or more reported aspects 14' that are relevant to achieving the one or more target outcomes. Such an operation may involve searching for the relevant one or more reported aspects 14' at a number of different locations via, for example, a wireless network and/or a wired network 50'. For example, such searching may be accomplished by transmitting a solicitation 13' for the one or more reported aspects 14' that are relevant to achieving the one or more target outcomes to one or more network servers 60', to one or more sensors 40', to one or more third parties 6', and/or to other one or more local source user devices 20'. In alternative or in the same implementations, a memory 116' may be searched for the one or more reported aspects 14'.

Once the one or more reported aspects 14' relevant to the achievement of the one or more target outcomes have been found, the local source user device 20a' may develop the one or more personalized plans 16' by, for example, including into the one or more personalized plans 16', one or more emulatable aspects that corresponds to one or more reported aspects 14' that have been found to be relevant to the achievement of the one or more target outcomes. As in the case of the first exemplary environment of FIGS. 1a and 1b, a personalized plan 16' may, in some cases, merely be a collection of one or more emulatable aspects. In other cases, however, a personalized plan 16' may define the specific relationships (e.g., spatial, temporal, or specific time relationships) between multiple emulatable aspects. And as in the case of the first exemplary environment, a personalized plan 16' may include other information such as emulatable intermediate outcomes. After developing the one or more personalized plans 16', the local source user device 20a' may then be designed to present the developed one or more personalized plans 16' to, for example, an end user 4' (via the local end user device 30), one or more network servers 60, a source user 2a' (e.g., via user interface 120'), and/or one or more third parties 6'.

The local source user device 20a', as illustrated in FIG. 2b, may include the same or similar modules, sub-modules, and other components included in the server 10 of FIG. 1b. As illustrated, the local source user device 20a' may include a request reception module 102' (which may further include a network interface reception module 202', a reported aspect seeking module 104', a personalized plan development module 106', a presentation module 108' (which may further include a transmission module 224'), a memory 116' (which may store a plurality of reported aspects 15', one or more applications 140', one or more end user preferences 142', one or more end user limitations 144', and/or one or more third party sources 146'), and/or a network interface 118', similar to the server 10 of FIG. 1b.

Also similar to server 10 of FIG. 1b, the local source user device 20a' may also include a social networking entry reception module 110' (which may further include a blog entry reception module 111' and/or a status report reception module 112'), a diary entry reception module 114', and/or a sensor data reception module 115'. All of these modules, sub-modules, and other components of the local source user device 20a' may perform the same or similar functions as their counterparts that may be included in the server 10 of FIG. 1b. In addition to these modules, sub-modules, and other components, the local source user device 20' may include a user interface 120' and a user interface indication module 226' (which may be included with the presentation module 108'). The user interface indication module 226' may be designed to indicate, for example, the one or more personalized plans 16' via the user interface 120'. The user interface 120' may include one or more of, for example, a display monitor, a touchscreen, a keyboard, a keypad, a mouse, an audio system including one or more speakers, a microphone, an image capturing device such as a digital camera, and so forth.

Turning now to FIGS. 3a and 3b, which as previously indicated, illustrates a third example environment in which the methods, systems, circuitry, and computer program products in accordance with various embodiments may be implemented at a local end user device 30" rather than at a server 10" or at a local source user device 20a' as was the case in the first and second example environments of FIGS. 1a and 1b and FIGS. 2a and 2b. The third example environment of FIGS. 3a and 3b is similar to the first example environment of FIGS. 1a and 1b and the second example environment of FIGS. 2a and 2b with few minor differences. For example, in the third example environment, the local end user device 30" may receive a request 12" for the one or more personalized plans 16" directly from an end user 4" via a user interface 120" rather than via the wireless network and/or wired network 50" as was the case for the server 10 of the first example environment of FIGS. 1a and 1b and as was the case for the local source user device 20a' of the second example environment of FIGS. 2a and 2b. However, and as with the server 10 and the local source user device 20a' of FIGS. 1b and 2b, the local end user device 30" may also alternatively receive a request 12" via the wireless network and/or wired network 50" from other sources such as from one or more third parties 6" or from a network server 60".

As illustrated, the third example environment of FIGS. 3a and 3b may include a third exemplary system 100", which includes at least a local end user device 30" (see FIG. 3b). In general, the local end user device 30" may be designed to receive a request 12" for one or more personalized plans 16" that are designed to facilitate an end user 4" to achieve one or more target outcomes. In some implementations, the request 12" may be received directly from the end user 4" via a user interface 120". Alternatively, and although not depicted, the request 12" may be received via wireless network and/or wired network 50" from, for example, one or more third parties 6" or from a network server 60". As before in the first and second exemplary environments, the request 12" may identify one or more target outcomes in various implementations. Also as before, in some implementations, the request 12" may not identify any source user **2*"**.

In response to receiving the request 12", the local end user device 30" may be designed to execute an operation to seek (e.g., identify or search) one or more reported aspects 14" that are relevant to achieving the one or more target outcomes. Such an operation may involve, in some cases, searching for the relevant one or more reported aspects 14" at a number of different locations via, for example, a wireless network and/or a wired network 50". For example, such searching may be accomplished by transmitting a solicitation 13" for the one or more reported aspects 14" that are relevant to achieving the one or more target outcomes to one or more network servers 60", to one or more sensors 40", to one or more third parties 6", and/or to one or more local source user devices 20". In alternative or in the same implementations, a memory 116" may be searched for the one or more reported aspects 14" that are relevant to achieving the one or more target outcomes.

Once the one or more reported aspects 14" relevant to the achievement of the one or more target outcomes have been found, the local end user device 30" may develop the one or more personalized plans 16" by, for example, including into the one or more personalized plans 16", at least one or more emulatable aspects that corresponds to one or more reported aspects 14" that have been found to be relevant to the achievement of the one or more target outcomes. As in the case of the first exemplary environment of FIGS. 1a and 1b and the second exemplary environment of FIGS. 2a and 2b, a personalized plan 16" may, in some cases, merely be a collection of one or more emulatable aspects. In other cases, however, a personalized plan 16" may define the specific relationships (e.g., spatial, temporal, or specific time relationships) between multiple emulatable aspects. And as in the case of the first and second exemplary environments, a personalized plan 16" may include other information such as emulatable intermediate outcomes. After developing the one or more personalized plans 16", the local end user device 30" may then be designed to present the developed one or more personalized plans 16" to, for example, an end user 4" (via the user interface 120"), one or more network servers 60", and/or one or more third parties 6".

In various implementations, the local end user device 30" may include the same or similar modules, sub-modules, and other components included in the local source user device 20a' of FIG. 2b. For example, the local end user device 30" may include a request reception module 102", a reported aspect seeking module 104", a personalized plan development module 106", a presentation module 108" (which may further include a transmission module 224" and a user interface indication module 226"), a memory 116" (which may store a plurality of reported aspects 15", one or more applications 140", one or more end user preferences 142", one or more end user limitations 144", and/or one or more third party sources 146"), a user interface 120", and/or a network interface 118", similar to the local source user device 20a' of FIG. 2b.

Also similar to the local source user device 20a' of FIG. 2b, the local end user device 30" may also include a social networking entry reception module 110" (which may further include a blog entry reception module 111" and/or a status report reception module 112"), a diary entry reception module 114", and/or a sensor data reception module 115". All of these modules, sub-modules, and components of the local end user device 30" may perform the same or similar functions as their counterparts that may be included in the local source user device 20a' of FIG. 2b. In addition to these modules, sub-modules, and components, the local end user device 30" may include a user interface reception module 203" (which may be included in the request reception module 102") for receiving the request 12" via a user interface 120". The user interface 120" may include one or more of, for example, a display monitor, a touchscreen, a keyboard, a keypad, a mouse, an audio system including one or more speakers, a microphone, an image capturing device such as a digital camera, and so forth.

FIG. 4a illustrates particular implementations of the reported aspect seeking module 104*(e.g., the reported aspect seeking module 104, the reported aspect seeking module 104', and the reported aspect seeking module 104") of FIGS. 1b, 2b, and 3b. As illustrated, the reported aspect seeking module 104* may include a network searching module 204* that is configured to, among other things, search for the one or more reported aspects 14* that are relevant to achieving the one or more target outcomes via at least one of a wireless network and a wired network 50. In various implementations, the network searching module 204* may further include a solicitation transmission module 206* configured to, among other things, transmit a solicitation 13* for the one or more reported aspects 14* that are relevant to achieving the one or more target outcomes to one or more remote network devices (e.g., in the embodiment depicted in FIGS. 1a and 1b, transmitting the solicitation 13 to one or more local source user devices 20, to one or more sensors 40, or to one or more network servers 60).

In various implementations, the reported aspect seeking module 104* may include a memory searching module 208*, a reported outcome identification module 210*, a reported aspect identification module 212*, a preference compliant reported aspect identification module 213*, a limitation compliant reported aspect identification module 214*, a reported plausible aspect identification module 216*, and/or a reported aspect reception module 218*. The memory searching module 208* may be configured to search a memory 116* for the one or more reported aspects 14* associated with at least the one or more target outcomes. The reported outcome identification module 210* may be configured to identify one or more reported outcomes that correspond to the one or more target outcomes to, for example, facilitate the seeking of the one or more reported aspects 14* that are relevant to achieving the one or more target outcomes. The reported aspect identification module 212* may be configured to, among other things, identify the one or more reported aspects 14* that are relevant to achieving the one or more target outcomes including identifying one or more reported aspects that occurred within one or more predefined time periods, respectively, from one or more occurrences of the one or more reported outcomes (e.g. as identified by the reported outcome identification module 210*).

The preference compliant reported aspect identification module 213* may be configured to, among other things, identify one or more reported aspects 14* that are relevant to achieving the one or more target outcomes including identifying one or more reported aspects 14* that complies with one or more preferences of an end user 4* and that are associated with the one or more reported outcomes (e.g., as identified by the reported outcome identification module 210*). The limitation compliant reported aspect identification module 214* may be configured to, among other things, identify one or more reported aspects 14* that are relevant to achieving the one or more target outcomes including identifying one or more reported aspects 14* that complies with one or more limitations associated with an end user 4* and that are associated with the one or more reported outcomes (e.g., as identified by the reported outcome identification module 210*). The reported plausible aspect identification module 216* may be configured to, among other things, identify one or more reported aspects 14* that are relevant to achieving the one or more target outcomes including identifying one or more reported plausible aspects that are associated with the one or more reported outcomes (e.g., as identified by the reported outcome identification module 210*) that corresponds to the one or more target outcomes, the one or more reported plausible aspects being aspects that have been successfully emulated by one or more third parties 6*. The reported aspect reception module 218* may be configured to receive one or more reported aspects 14* that are found by the reported aspect seeking module 104 to be relevant to achieving the one or more target outcomes.

FIG. 4b illustrates particular implementations of the personalized plan development module 106*(e.g., the personalized plan development module 106, the personalized plan development module 106', and the personalized plan development module 106") of FIGS. 1b, 2b, and 3b. In various implementations, the personalized plan development module 106* may include an emulatable aspect inclusion module 218*, a relationship defining module 220*, and/or an emulatable intermediate outcome inclusion module 222*. The emulatable aspect inclusion module 218* may be configured to, among other things, include into each of one or more personalized plans 16* to be developed one or more emulatable aspects that corresponds to one or more reported aspects that have been found to be relevant to achieving the one or more target outcomes of the one or more personalized plans 16*. The relationship defining module 220* may be configured to, among other things, define in each of the one or more personalized plans 16* to be developed one or more relationships (e.g., spatial, temporal, and/or specific time relationships) between the plurality of emulatable aspects included in each of the one or more personalized plans 16*. The emulatable intermediate outcome inclusion module 222* may be configured to, among other things, include into at least one of the one or more personalized plans 16* to be developed one or more emulatable intermediate outcomes related to the one or more target outcomes of the at least one of the one or more personalized plans 16*.

Referring back to the server 10 of FIG. 1b, the local source user device 20a' of FIG. 2b, and the local end user device 30", the various modules (e.g., the request reception module 102*, the reported aspect seeking module 104*, the personalized plan development module 106*, the presentation module 108*, and so forth) along with their sub-modules included in the server 10, the local source user device 20a', and the local end user device 30" may be implemented using hardware, software, firmware, or any combination thereof. For example, in some implementations the request reception module 102*, the reported aspect seeking module 104*, the personalized plan development module 106*, and/or the presentation module 108* may be implemented with a processor 1102 (e.g., microprocessor, controller, and so forth) executing computer readable instructions 1104 (e.g., computer program product) stored in a storage medium 1106 (e.g., volatile or non-volatile memory) such as a signal-bearing medium as depicted in the computing device 1100 of FIG. 11. Alternatively, hardware such as application specific integrated circuit (ASIC) may be employed in order to implement such modules in some alternative implementations.

Figure 5:
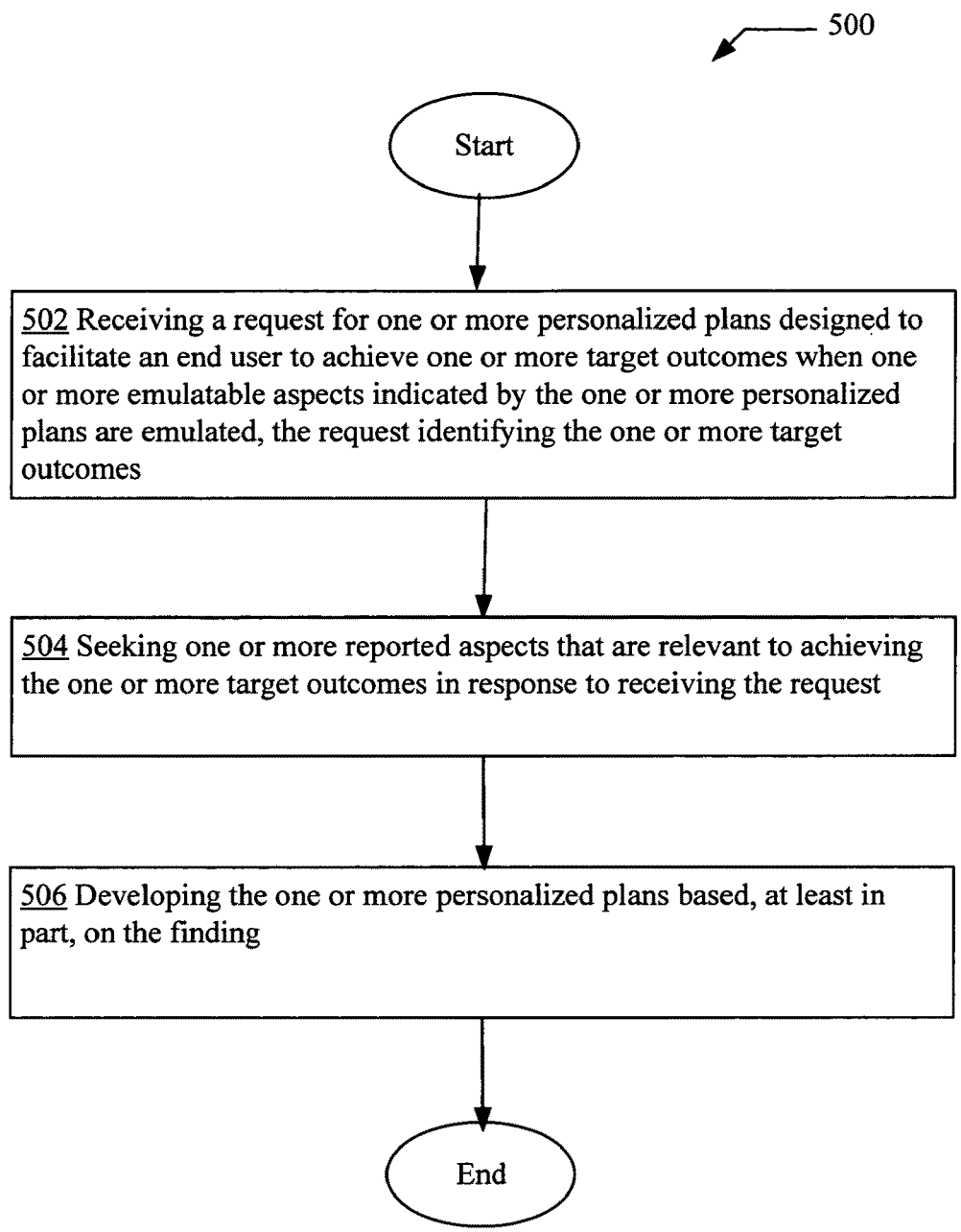
FIG. 5 is a high-level logic flowchart of a process.

A more detailed discussion related to the server 10 of FIG. 1b, the local source user device 20a' of FIG. 2b, and the local end user device 30" of FIG. 3b will now be provided with respect to the processes and operations to be described herein. FIG. 5 illustrates an operational flow 500 representing example operations related to, among other things, development of one or more personalized plans 16 designed to facilitate an end user 4 to achieve one or more target outcomes, the development of the one or more personalized plans 16 being in response to a reception of a request 12 that at least identifies the one or more target outcomes. In some embodiments, the operational flow 500 may be executed by, for example, the server 10 of FIG. 1b, the local source user device 20' of FIG. 2b, or the local end user device 30" of FIG. 3b.

In FIG. 5 and in the following figures that include various examples of operational flows, discussions and explanations may be provided with respect to the three exemplary environments described above as illustrated in FIGS. 1a and 1b, FIGS. 2a and 2b, and FIGS. 3a and 3b, and/or with respect to other examples (e.g., as provided in FIGS. 4a and 4b) and contexts. However, it should be understood that the operational flows may be executed in a number of other environments and contexts, and/or in modified versions of FIGS. 1a, 1b, 2a, 2b, 3a, 3b, 4a and 4b. Also, although the various operational flows are presented in the sequence(s) illustrated, it should be understood that the various operations may be performed in other orders than those which are illustrated, or may be performed concurrently.

Further, in FIG. 5 and in the figures to follow thereafter, various operations may be depicted in a box-within-a-box manner. Such depictions may indicate that an operation in an internal box may comprise an optional example embodiment of the operational step illustrated in one or more external boxes. However, it should be understood that internal box operations may be viewed as independent operations separate from any associated external boxes and may be performed in any sequence with respect to all other illustrated operations, or may be performed concurrently.

In any event, after a start operation, the operational flow 500 may move to a reception operation 502 for receiving a request for one or more personalized plans designed to facilitate an end user to achieve one or more target outcomes when one or more emulatable aspects indicated by the one or more personalized plans are emulated, the request identifying the one or more target outcomes. For instance, and as an illustration, the request reception module 102*(e.g., the request reception module 102, the request reception module 102', or the request reception module 102") of the server 10 of FIG. 1b, the local source user device 20' of FIG. 2b, or the local end user device 30" of FIG. 3b receiving a request 12*(e.g., via a wireless network and/or wired network 50* or via a user interface 120*) for one or more personalized plans 16* designed to facilitate an end user 4* to achieve one or more target outcomes when one or more emulatable aspects (e.g., one or more behaviors, one or more acts, one or more beliefs, one or more traits, and/or other types of characteristics or traits) indicated by the one or more personalized plans 16* are emulated, the request 12* identifying the one or more target outcomes (e.g., weight loss, development or improvement of user skills such as work skills, athletic or game skills, or social skills, developing or having particular subjective user states such as well-rested and/or well-being, and so forth). Note that in various implementations, the request 12* may not specify or identify any source user 2** (e.g., source user 2a, source user 2b, source user 2a', source user 2b', and so forth). Instead, the development of the one or more personalized plans 16* may at least be prompted by the identification of the one or more target outcomes by the request 12*. The identification of the one or more target outcomes may be made by various means including, for example, textual or audio descriptions of the one or more target outcomes, textual or audio names of the one or more target outcomes, images such as digital images of the target outcomes as displayed by a source user 2**, and so forth.

Operational flow 500 may also include a seeking operation 504 for seeking one or more reported aspects that are relevant to achieving the one or more target outcomes in response to receiving the request. For instance, the reported aspect seeking module 104* of the server 10 of FIG. 1b, of the local source user device 20' of FIG. 2b, or of the local end user device 30" of FIG. 3b seeking (e.g., searching in a memory 116* and/or searching through a wireless network and/or wired network 50*) one or more reported aspects 14 that are relevant (e.g., as indicated by a source user 2**, an end user 4*, a third party 6*, one or more third party sources such as a publication or research, or based on other factors) to achieving the one or more target outcomes in response to receiving the request 12*.

Finally, operational flow 500 may include a development operation 506 for developing the one or more personalized plans based, at least in part, on the seeking. For instance, the personalized plan development module 106* of the server 10 of FIG. 1b, of the local source user device 20' of FIG. 2b, or of the local end user device 30" of FIG. 3b developing (e.g., creating) the one or more personalized plans 16* based, at least in part, on the seeking.

Figure 6A:
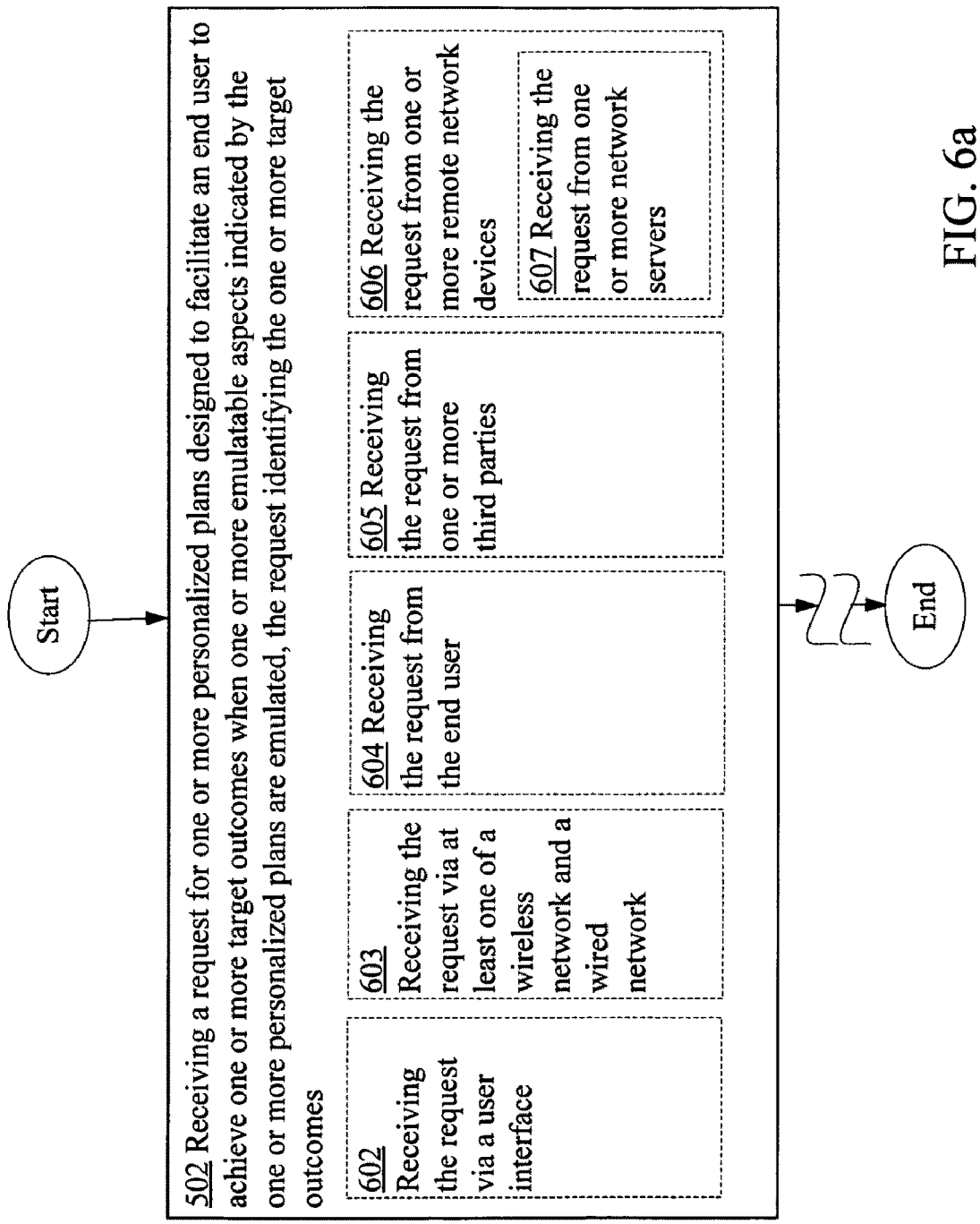
FIG. 6a is a high-level logic flowchart of a process depicting alternate implementations of the reception operation 502 of FIG. 5.

In various implementations, the reception operation 502 of FIG. 5 may be executed in a number of different ways as illustrated in FIGS. 6a, 6b, 6c, 6d, 6e, and 6f. For example, the request 12* received through the reception operation 502 may be received by various means depending upon, for example, whether the operation is being implemented at a server 10 (e.g., as in the embodiment depicted in FIGS. 1a and 1b), at a xlocal source user device 20' (e.g., as in the embodiment depicted in FIGS. 2a and 2b), or at a local end user device 30" (e.g., as in the embodiment depicted in FIGS. 3a and 3b). For example, in some implementations the reception operation 502 may include an operation 602 for receiving the request via a user interface as depicted in FIG. 6a. For instance, the user interface reception module 203" of the local end user device 30" of FIG. 3b receiving the request 12" via a user interface 120" (e.g., an audio system including a microphone, a keypad, a touchscreen, a mouse, and so forth).

Alternatively, the reception operation 502 may include an operation 603 for receiving the request via at least one of a wireless network and a wired network as depicted in FIG. 6a. For instance, the network interface reception module 202* (e.g., network interface reception module 202 or network interface reception module 202') of the server 10 of FIG. 1b or the local source user device 20' of FIG. 2b receiving the request 12*(e.g., request 12 or request 12') via at least one of wireless network and a wired network 50*.

The request 12* may be received from a variety of sources in various alternative implementations. For example, in some implementations the reception operation 502 may include an operation 604 for receiving the request from the end user as depicted in FIG. 6a. For instance, the request reception module 102* of the server 10 of FIG. 1b, the local source user device 20' of FIG. 2b, or the local end user device 30" of FIG. 3b receiving the request 12* from the end user 4*. For example, in the embodiment depicted in FIGS. 1a and 1b the request reception module 102 of the server 10 receiving the request 12 from the end user 4 via a wireless network and/or wired network 50. In the embodiment depicted in FIGS. 3a and 3b the request reception module 102" of the local end user device 30" receiving the request 12" from the end user 4" via a user interface 120". Note that in various alternative implementations, the request 12* may not specifically identify a source user 2**, but instead may merely identify one or more target outcomes.

In some implementations, the reception operation 502 may include an operation 605 for receiving the request from one or more third parties as depicted in FIG. 6a. For instance, the request reception module 102* of the server 10 of FIG. 1b, the local source user device 20' of FIG. 2b, or the local end user device 30" of FIG. 3b receiving the request 12* from one or more third parties 6*(e.g., network service provider, content provider, social networking sites, other end users, and so forth).

In some implementations, the reception operation 502 may include an operation 606 for receiving the request from one or more remote network devices as depicted in FIG. 6a. For instance, the request reception module 102* of the server 10 of FIG. 1b, the local source user device 20' of FIG. 2b, or the local end user device 30" of FIG. 3b receiving the request 12* from one or more remote network devices. For example, in the case of the request reception module 102 of the server 10 of FIGS. 1*a* and 1*b* receiving the request 12 from a local end user device 30 or from a network server 60.

In some implementations, operation 606 may include an operation 607 for receiving the request from one or more network servers as depicted in FIG. 6*a*. For instance, the request reception module 102* of the server 10 of FIG. 1*b*, the local source user device 20' of FIG. 2*b*, or the local end user device 30" of FIG. 3*b* receiving the request 12* from one or more network servers 60*.

Figure 6B:
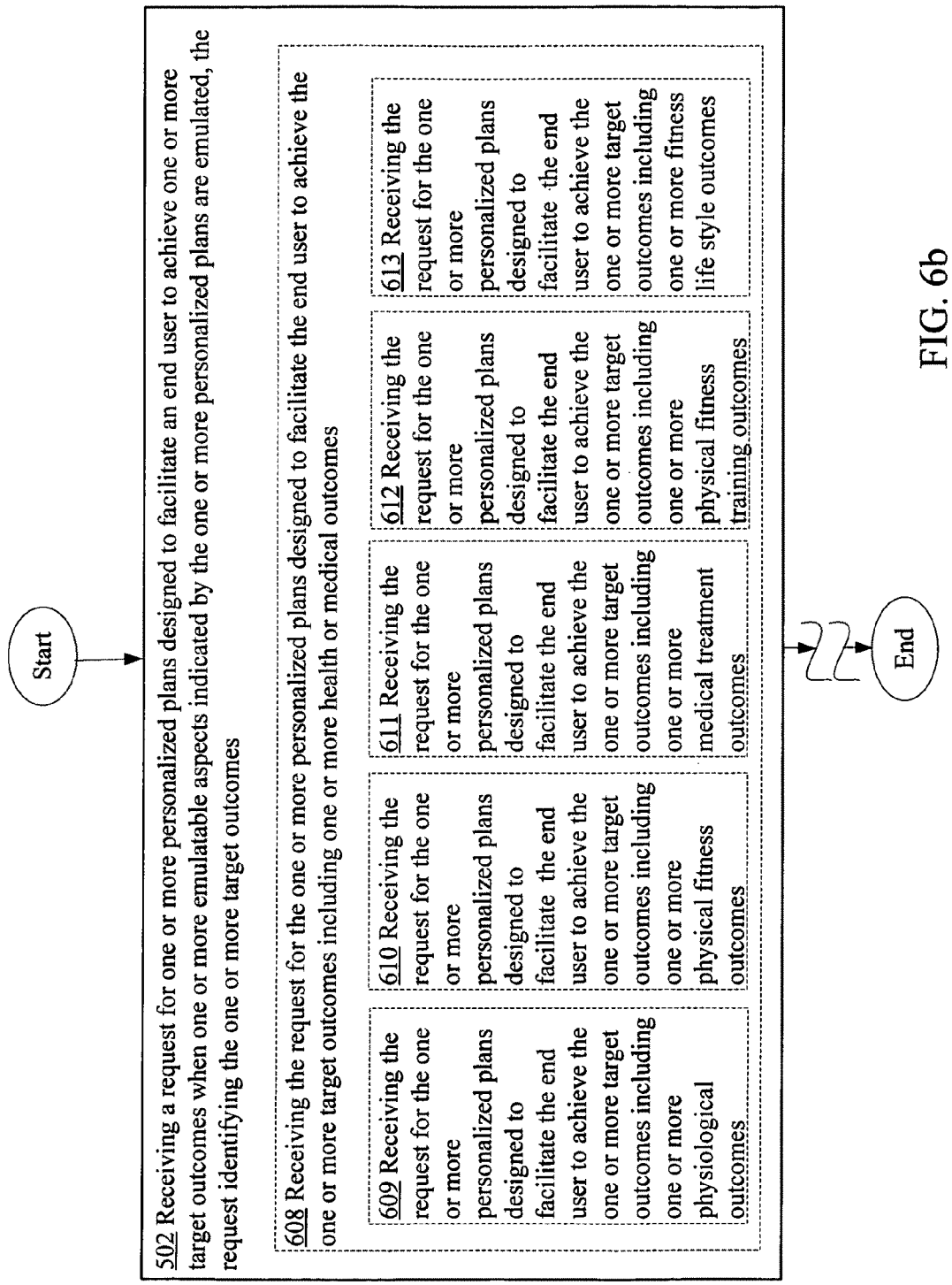
FIG. 6b is a high-level logic flowchart of a process depicting alternate implementations of the reception operation 502 of FIG. 5.

The one or more personalized plans 16* that may be requested may be designed to achieve one or more of a wide variety of target outcomes. For example, in some implementations, the reception operation 502 may include an operation 608 for receiving the request for the one or more personalized plans designed to facilitate the end user to achieve the one or more target outcomes including one or more health or medical outcomes as depicted in FIG. 6*b*. For instance, the request reception module 102* of the server 10 of FIG. 1*b*, the local source user device 20' of FIG. 2*b*, or the local end user device 30" of FIG. 3*b* receiving the request 12* for the one or more personalized plans 16* designed to facilitate the end user 4* to achieve the one or more target outcomes including one or more health or medical outcomes (e.g., recovery time or recovery success related to an illness, weight loss, blood pressure reduction, blood glucose level reduction, lifespan, and so forth).

Operation 608 may in turn include one or more additional operations in various implementations. For example, in some implementations, operation 608 may include an operation 609 for receiving the request for the one or more personalized plans designed to facilitate the end user to achieve the one or more target outcomes including one or more physiological outcomes as depicted in FIG. 6*b*. For instance, the request reception module 102* of the server 10 of FIG. 1*b*, the local source user device 20' of FIG. 2*b*, or the local end user device 30" of FIG. 3*b* receiving the request 12* for the one or more personalized plans 16* designed to facilitate the end user 4* to achieve the one or more target outcomes including one or more physiological outcomes (e.g., reducing blood pressure or blood glucose levels, increase red blood cell count, improve and so forth).

In the same or different implementations, operation 608 may include an operation 610 for receiving the request for the one or more personalized plans designed to facilitate the end user to achieve the one or more target outcomes including one or more physical fitness outcomes as depicted in FIG. 6*b*. For instance, the request reception module 102* of the server 10 of FIG. 1*b*, the local source user device 20' of FIG. 2*b*, or the local end user device 30" of FIG. 3*b* receiving the request 12* for the one or more personalized plans 16* designed to facilitate the end user 4* to achieve the one or more target outcomes including one or more physical fitness outcomes (e.g., reduced body fat level, increased lung air capacity, reduce time it takes to run a mile, increase amount of sit-ups or push-ups, and so forth).

In the same or different implementations, operation 608 may include an operation 611 for receiving the request for the one or more personalized plans designed to facilitate the end user to achieve the one or more target outcomes including one or more medical treatment outcomes as depicted in FIG. 6*b*. For instance, the request reception module 102* of the server 10 of FIG. 1*b*, the local source user device 20' of FIG. 2*b*, or the local end user device 30" of FIG. 3*b* receiving the request 12* for the one or more personalized plans 16* designed to facilitate the end user 4* to achieve the one or more target outcomes including one or more medical treatment outcomes (e.g., improved recovery from stroke or other types of disease, reduction of side-effects from a medical treatment such as chemotherapy, and so forth).

In the same or different implementations, operation 608 may include an operation 612 for receiving the request for the one or more personalized plans designed to facilitate the end user to achieve the one or more target outcomes including one or more physical fitness training outcomes as depicted in FIG. 6*b*. For instance, the request reception module 102* of the server 10 of FIG. 1*b*, the local source user device 20' of FIG. 2*b*, or the local end user device 30" of FIG. 3*b* receiving the request 12* for the one or more personalized plans 16* designed to facilitate the end user 4* to achieve the one or more target outcomes including one or more physical fitness training outcomes (e.g., reduce soreness from exercising, improve results of a training program, and so forth).

In the same or different implementations, operation 608 may include an operation 613 for receiving the request for the one or more personalized plans designed to facilitate the end user to achieve the one or more target outcomes including one or more fitness life style outcomes as depicted in FIG. 6*b*. For instance, the request reception module 102* of the server 10 of FIG. 1*b*, the local source user device 20' of FIG. 2*b*, or the local end user device 30" of FIG. 3*b* receiving the request 12* for the one or more personalized plans 16* designed to facilitate the end user 4* to achieve the one or more target outcomes including one or more fitness life style outcomes (e.g., quit smoking, getting regular eight hours of nightly sleep, sticking with a vegan or low carbohydrate diet, and so forth).

Figure 6C:
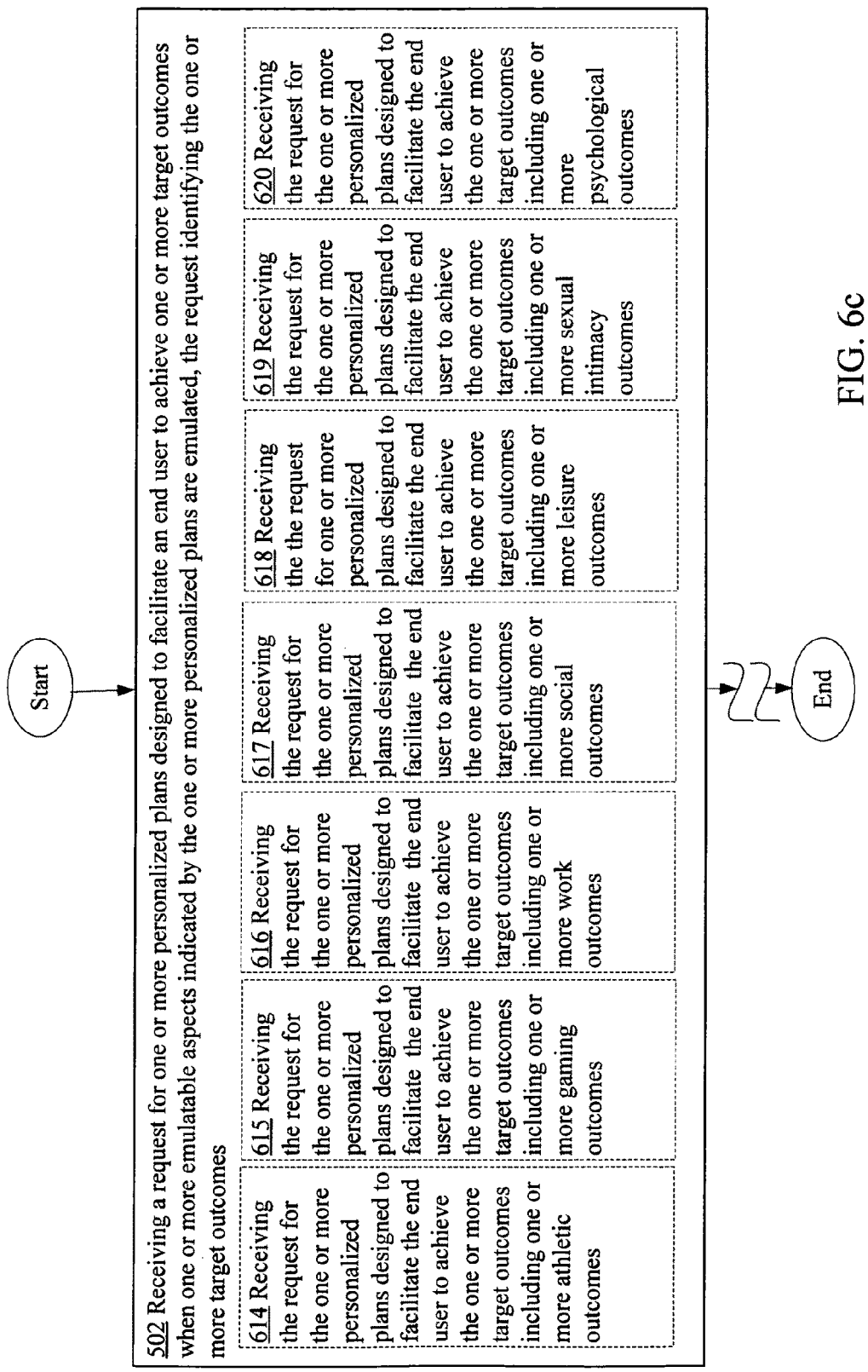
FIG. 6c is a high-level logic flowchart of a process depicting alternate implementations of the reception operation 502 of FIG. 5.

In some implementations, the reception operation 502 of FIG. 5 may include an operation 614 for receiving the request for the one or more personalized plans designed to facilitate the end user to achieve the one or more target outcomes including one or more athletic outcomes as depicted in FIG. 6*c*. For instance, the request reception module 102* of the server 10 of FIG. 1*b*, the local source user device 20' of FIG. 2*b*, or the local end user device 30" of FIG. 3*b* receiving the request 12* for the one or more personalized plans 16* designed to facilitate the end user 4* to achieve the one or more target outcomes including one or more athletic outcomes (e.g., improve golf scores, win a bicycle or swimming race, develop a curve ball pitch, and so forth).

In some implementations, the reception operation 502 may include an operation 615 for receiving the request for the one or more personalized plans designed to facilitate the end user to achieve the one or more target outcomes including one or more gaming outcomes as depicted in FIG. 6*c*. For instance, the request reception module 102* of the server 10 of FIG. 1*b*, the local source user device 20' of FIG. 2*b*, or the local end user device 30" of FIG. 3*b* receiving the request 12* for the one or more personalized plans 16* designed to facilitate the end user 4* to achieve the one or more target outcomes related to one or more gaming outcomes (e.g., winning a chest tournament or improve video gaming skills).

In some implementations, the reception operation 502 may include an operation 616 for receiving the request for the one or more personalized plans designed to facilitate the end user to achieve the one or more target outcomes including one or more work outcomes as depicted in FIG. 6*c*. For instance, the request reception module 102* of the server 10 of FIG. 1*b*, the local source user device 20' of FIG. 2*b*, or the local end user device 30" of FIG. 3*b* receiving the request 12* for the one or more personalized plans 16* designed to facilitate the end user 4* to achieve the one or more target outcomes including one or more work outcomes (e.g., a job promotion, finish a project on time, and so forth).

In some implementations, the reception operation 502 may include an operation 617 for receiving the request for the one or more personalized plans designed to facilitate the end user to achieve the one or more target outcomes including one or more social outcomes as depicted in FIG. 6c. For instance, the request reception module 102* of the server 10 of FIG. 1b, the local source user device 20' of FIG. 2b, or the local end user device 30" of FIG. 3b receiving the request 12* for the one or more personalized plans 16* designed to facilitate the end user 4* to achieve the one or more target outcomes including one or more social outcomes (e.g., attaining a certain social class, having a dinner date with a particular person, developing a particular reputation, and so forth).

In some implementations, the reception operation 502 may include an operation 618 for receiving the request for the one or more personalized plans designed to facilitate the end user to achieve the one or more target outcomes including one or more leisure outcomes as depicted in FIG. 6c. For instance, the request reception module 102* of the server 10 of FIG. 1b, the local source user device 20' of FIG. 2b, or the local end user device 30" of FIG. 3b receiving the request 12* for one or more personalized plans 16* designed to facilitate the end user 4* to achieve the one or more target outcomes including one or more leisure outcomes (e.g., learn how to knit, finding time to go on vacation, finish reading a book, and so forth).

In some implementations, the reception operation 502 may include an operation 619 for receiving the request for the one or more personalized plans designed to facilitate the end user to achieve the one or more target outcomes including one or more sexual intimacy outcomes as depicted in FIG. 6c. For instance, the request reception module 102* of the server 10 of FIG. 1b, the local source user device 20' of FIG. 2b, or the local end user device 30" of FIG. 3b receiving the request 12* for the one or more personalized plans 16* designed to facilitate the end user 4* to achieve the one or more target outcomes including one or more sexual intimacy outcomes (e.g., increased sexual activities, increased sexual performance, and so forth).

In some implementations, the reception operation 502 may include an operation 620 for receiving the request for the one or more personalized plans designed to facilitate the end user to achieve the one or more target outcomes including one or more psychological outcomes as depicted in FIG. 6c. For instance, the request reception module 102* of the server 10 of FIG. 1b, the local source user device 20' of FIG. 2b, or the local end user device 30" of FIG. 3b receiving the request 12* for the one or more personalized plans 16* designed to facilitate the end user 4* to achieve the one or more target outcomes including one or more psychological outcomes (e.g., overcoming a phobia, overcoming certain addictive behavior such as compulsion to be clean, and so forth).

Figure 6D:
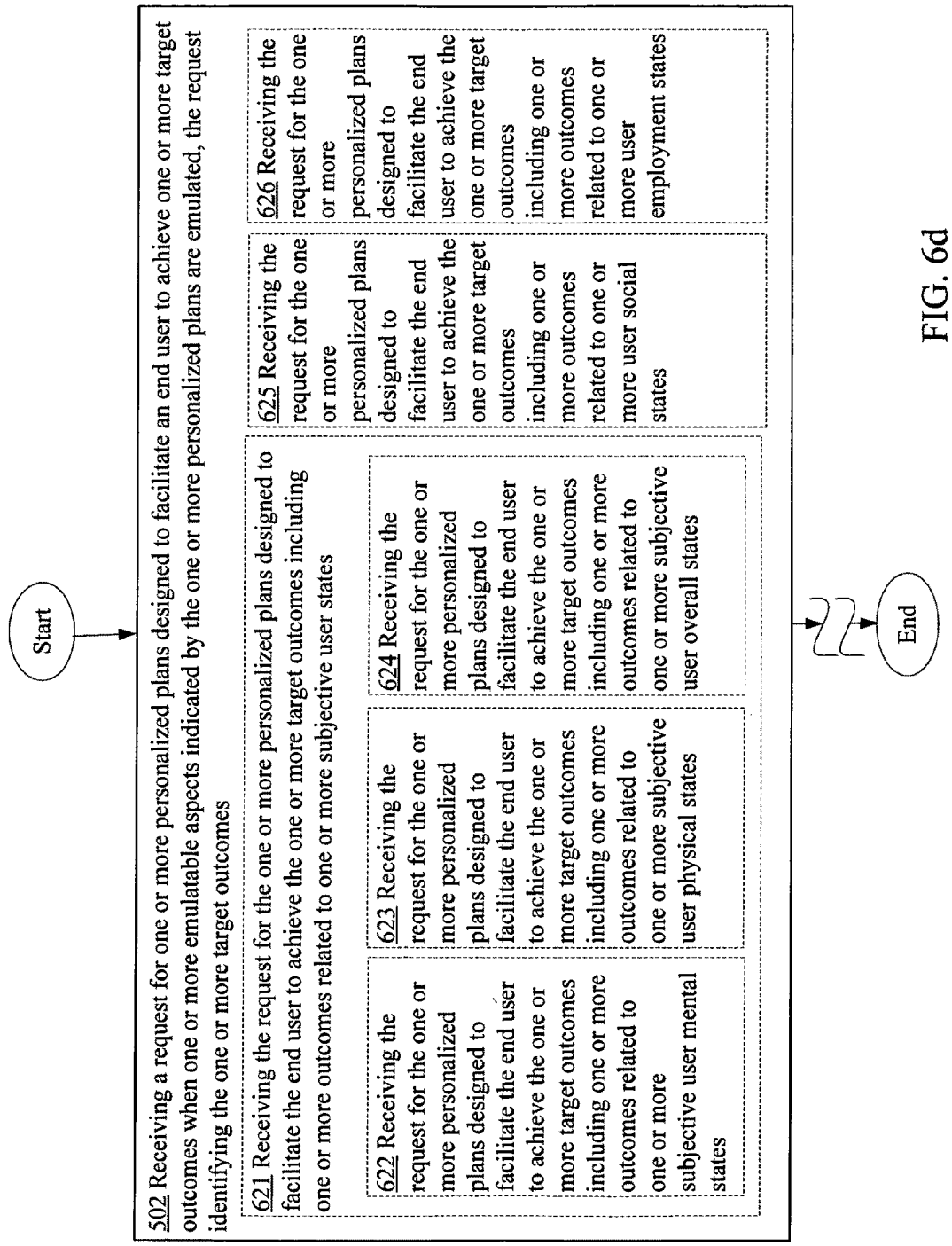
FIG. 6d is a high-level logic flowchart of a process depicting alternate implementations of the reception operation 502 of FIG. 5.

In some implementations, the reception operation 502 may include an operation 621 for receiving the request for the one or more personalized plans designed to facilitate the end user to achieve the one or more target outcomes including one or more outcomes related to one or more subjective user states as depicted in FIG. 6d. For instance, the request reception module 102* of the server 10 of FIG. 1b, the local source user device 20' of FIG. 2b, or the local end user device 30" of FIG. 3b receiving the request 12* for the one or more personalized plans 16* designed to facilitate the end user 4* to achieve the one or more target outcomes including one or more outcomes related to one or more subjective user states. A subjective user state may be any user state or status associated with a user that may generally only be subjectively indicated by the user. The one or more personalized plans 16* that may be requested may be designed to facilitate the end user 4* to achieve various types of subjective user states in various alternative implementations.

For example, in some implementations, operation 621 may include an operation 622 for receiving the request for the one or more personalized plans designed to facilitate the end user to achieve the one or more target outcomes including one or more outcomes related to one or more subjective user mental states as depicted by FIG. 6d. For instance, the request reception module 102* of the server 10 of FIG. 1b, the local source user device 20' of FIG. 2b, or the local end user device 30" of FIG. 3b receiving the request 12* for the one or more personalized plans 16* designed to facilitate the end user 4* to achieve the one or more target outcomes including one or more outcomes related to one or more subjective user mental states (e.g., happiness, alertness, clarity of thinking, calmness, and so forth). A subjective user mental state is any subjective user state related to any mental aspect of a subject (e.g., user).

In the same or different implementations, operation 621 may include an operation 623 for receiving the request for the one or more personalized plans designed to facilitate the end user to achieve the one or more target outcomes including one or more outcomes related to one or more subjective user physical states as depicted in FIG. 6d. For instance, the request reception module 102* of the server 10 of FIG. 1b, the local source user device 20' of FIG. 2b, or the local end user device 30" of FIG. 3b receiving the request 12* for the one or more personalized plans 16* designed to facilitate the end user 4* to achieve the one or more target outcomes including one or more outcomes related to one or more subjective user physical states (e.g., physical fatigue, pain, blurry vision, and so forth). A subjective user physical state is any subjective user state related to any physical aspect of a subject (e.g., user).

In the same or different implementations, operation 621 may include an operation 624 for receiving the request for the one or more personalized plans designed to facilitate the end user to achieve the one or more target outcomes including one or more outcomes related to one or more subjective user overall states as depicted in FIG. 6d. For instance, the request reception module 102* of the server 10 of FIG. 1b, the local source user device 20' of FIG. 2b, or the local end user device 30" of FIG. 3b receiving the request 12* for the one or more personalized plans 16* designed to facilitate the end user 4* to achieve the one or more target outcomes including one or more outcomes related to one or more subjective user overall states (e.g., "good," "bad," "well," "tired," "available," "busy," and so forth). A subjective user overall state is any subjective user state related to a subject and is not a subjective user mental state or a subjective user physical state.

In some implementations, the reception operation 502 of FIG. 5 may include an operation 625 for receiving the request for the one or more personalized plans designed to facilitate the end user to achieve the one or more target outcomes including one or more outcomes related to one or more user social states as depicted in FIG. 6d. For instance, the request reception module 102* of the server 10 of FIG. 1b, the local source user device 20' of FIG. 2b, or the local end user device 30" of FIG. 3b receiving the request 12* for the one or more personalized plans 16* designed to facilitate the end user 4* to achieve the one or more target outcomes including one or more outcomes related to one or more user social states (e.g., membership to a social group, being married, being single and so forth).

In some implementations, the reception operation 502 of FIG. 5 may include an operation 626 for receiving the request for the one or more personalized plans designed to facilitate the end user to achieve the one or more target outcomes including one or more outcomes related to one or more user employment states as depicted in FIG. 6d. For instance, the request reception module 102* of the server 10 of FIG. 1b, the local source user device 20' of FIG. 2b, or the local end user device 30" of FIG. 3b receiving the request 12* for the one or more personalized plans 16* designed to facilitate the end user 4* to achieve the one or more target outcomes including one or more outcomes related to one or more user employment states (e.g., being employed, attaining a particular employment position, attaining managerial authority, and so forth).

Figure 6E:
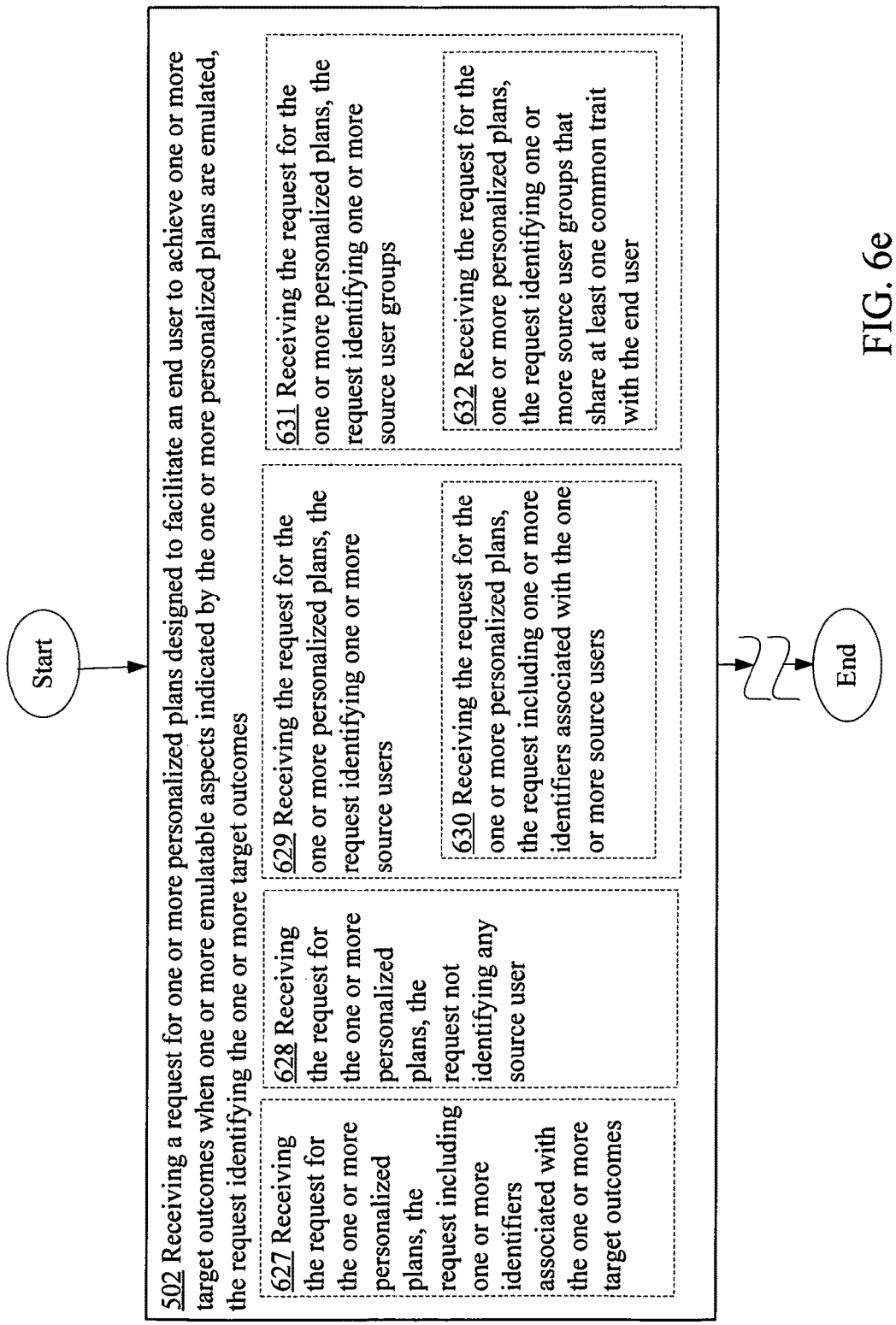
FIG. 6e is a high-level logic flowchart of a process depicting alternate implementations of the reception operation 502 of FIG. 5.

In some implementations, the reception operation 502 of FIG. 5 may include an operation 627 for receiving the request for the one or more personalized plans, the request including one or more identifiers associated with the one or more target outcomes as depicted in FIG. 6e. For instance, the request reception module 102* of the server 10 of FIG. 1b, the local source user device 20' of FIG. 2b, or the local end user device 30" of FIG. 3b receiving the request 12* for the one or more personalized plans 16*, the request 12* including one or more identifiers (e.g., one or more images of a source user 2* showing the one or more desired or target outcomes, textual or audio indications of the one or more target outcomes, and so forth) associated with the one or more target outcomes.

In some implementations, the reception operation 502 of FIG. 5 may include an operation 628 for receiving the request for the one or more personalized plans, the request not identifying any source user as depicted in FIG. 6e. For instance, the request reception module 102* of the server 10 of FIG. 1b, the local source user device 20' of FIG. 2b, or the local end user device 30" of FIG. 3b receiving the request 12* for the one or more personalized plans 16*, the request 12* not identifying any source user 2**. For these implementations, the development of the one or more personalized plans 16* may be based primarily on the identification of the one or more target outcomes (e.g., as identified in the request 12*) and may not rely on any identification of any source user 2**.

In alternative implementations, however, the request 12* received through the reception operation 502 of FIG. 5 may identify one or more source users 2*. For example, in some implementations, the reception operation 502 may include an operation 629 for receiving the request for the one or more personalized plans, the request identifying one or more source users as depicted in FIG. 6e. For instance, the request reception module 102* of the server 10 of FIG. 1b, the local source user device 20' of FIG. 2b, or the local end user device 30" of FIG. 3b receiving the request 12* for the one or more personalized plans 16*, the request 12* identifying one or more source users 2*.

In some implementations, operation 629 may, in turn, include an operation 630 for receiving the request for the one or more personalized plans, the request including one or more identifiers associated with the one or more source users as depicted in FIG. 6e. For instance, the request reception module 102* of the server 10 of FIG. 1b, the local source user device 20' of FIG. 2b, or the local end user device 30" of FIG. 3b receiving the request 12* for the one or more personalized plans 16*, the request 12* including one or more identifiers associated with the one or more source users 2* (e.g., one or more images of the one or more source users 2*, voice identifications of the one or more source users 2*, user names of the one or more source users 2*, actual names of the one or more source users 2*, locational identification of the one or more source users 2*, radio frequency identifications (RFIDs) of the one or more source users 2*, and so forth).

In some implementations, the reception operation 502 may include an operation 631 for receiving the request for the one or more personalized plans, the request identifying one or more source user groups as depicted in FIG. 6e. For instance, the request reception module 102* of the server 10 of FIG. 1b, the local source user device 20' of FIG. 2b, or the local end user device 30" of FIG. 3b receiving the request 12* for the one or more personalized plans 16*, the request 12* identifying one or more source user groups (e.g., one or more social networking groups, one or more ethnic or cultural groups, a gender group, one or more business groups, one or more medical patient groups, and so forth).

Operation 631, in turn, may further include an operation 632 for receiving the request for the one or more personalized plans, the request identifying one or more source user groups that share at least one common trait with the end user as depicted in FIG. 6e. For instance, the request reception module 102* of the server 10 of FIG. 1b, the local source user device 20' of FIG. 2b, or the local end user device 30" of FIG. 3b receiving the request 12* for the one or more personalized plans 16*, the request 12* identifying one or more source user groups that share at least one common trait (e.g., one or more physical characteristics, one or more ailments or illnesses, one or more handicaps, one or more social or employment status, belonging to the same social networking groups, and so forth) with the end user 4*.

Figure 6F:
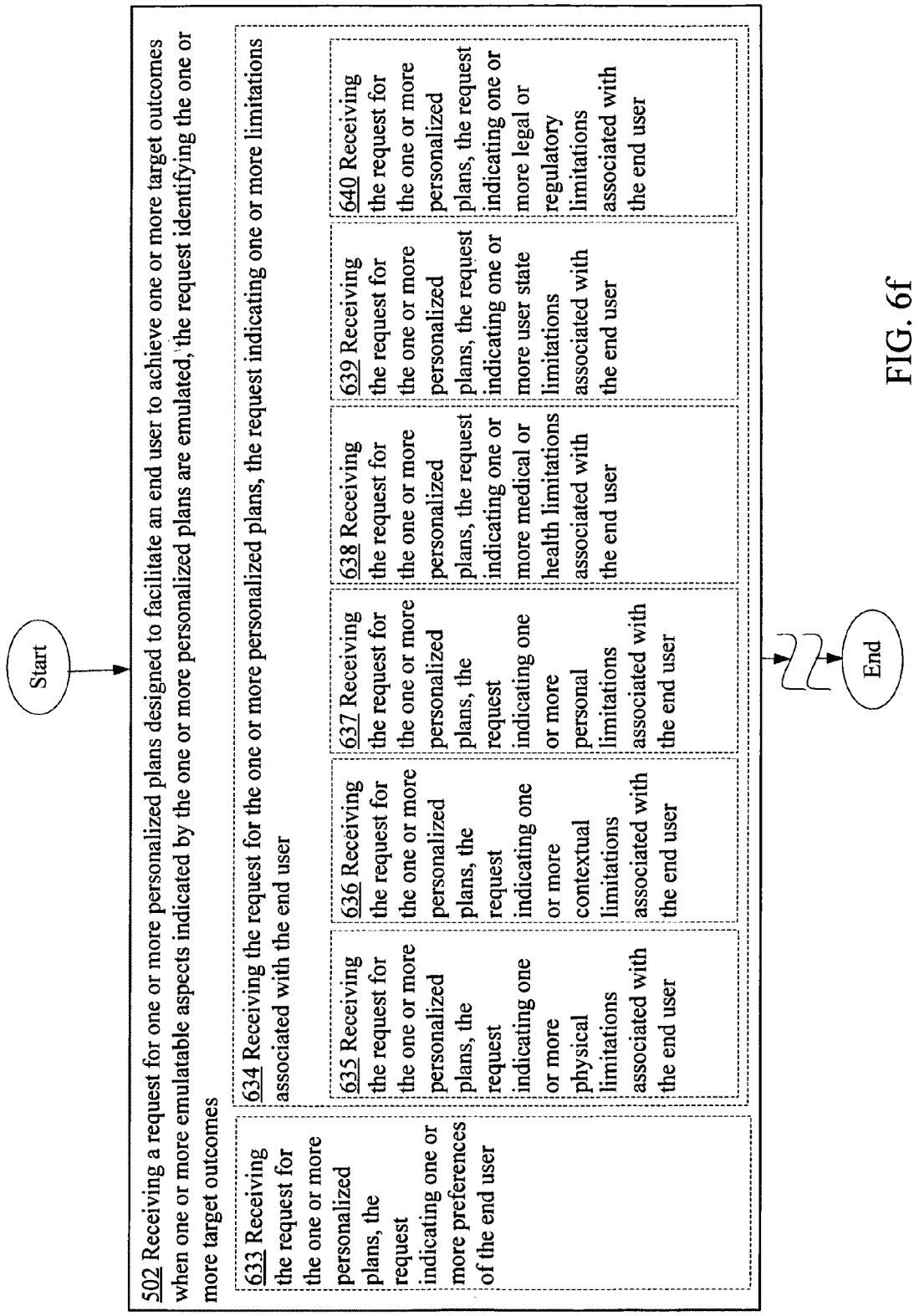
FIG. 6f is a high-level logic flowchart of a process depicting alternate implementations of the reception operation 502 of FIG. 5.

Various other types of information may be indicated by the request 12* received through the reception operation 502 of FIG. 5 in various alternative implementations. For example, in some implementations, the reception operation 502 may include an operation 633 for receiving the request for the one or more personalized plans, the request indicating one or more preferences of the end user as depicted in FIG. 6f. For instance, the request reception module 102* of the server 10 of FIG. 1b, the local source user device 20' of FIG. 2b, or the local end user device 30" of FIG. 3b receiving the request 12* for the one or more personalized plans 16*, the request 12* indicating one or more preferences (e.g., preference not to eat meats, preference not to exercise on Mondays, preference to sleep late on Fridays, and so forth) of the end user 4*.

In the same or different implementations, the reception operation 502 of FIG. 5 may include an operation 634 for receiving the request for the one or more personalized plans, the request indicating one or more limitations associated with the end user as depicted in FIG. 6f. For instance, the request reception module 102* of the server 10 of FIG. 1b, the local source user device 20' of FIG. 2b, or the local end user device 30" of FIG. 3b receiving the request 12* for the one or more personalized plans 16*, the request 12* indicating one or more limitations (e.g., physical limitations, logistical limitations, asset limitations, and so forth) associated with the end user 4*.

Operation 634 may, in turn, further include one or more additional operations in various alternative implementations. For example, in some implementations, operation 634 may include an operation 635 for receiving the request for the one or more personalized plans, the request indicating one or more physical limitations associated with the end user as depicted in FIG. 6f. For instance, the request reception module 102* of the server 10 of FIG. 1b, the local source user device 20' of FIG. 2b, or the local end user device 30" of FIG. 3b receiving the request 12* for the one or more personalized plans 16*, the request 12* indicating one or more physical limitations (e.g., visual or hearing limitations, physical movement limitations such as those related to a paraplegic, physical characteristic limitations such as height, weight, and so forth, related to the end user 4*, physiological limitations such as cholesterol levels, and so forth) associated with the end user 4*.

In the same or different implementations, operation 634 may include an operation 636 for receiving the request for the one or more personalized plans, the request indicating one or more contextual limitations associated with the end user as depicted in FIG. 6f. For instance, the request reception module 102* of the server 10 of FIG. 1b, the local source user device 20' of FIG. 2b, or the local end user device 30" of FIG. 3b receiving the request 12* for the one or more personalized plans 16*, the request 12* indicating one or more contextual limitations (e.g., scheduling limitations, geographical limitations, asset limitations such as lack of particular equipment or facilities, and so forth) associated with the end user 4*.

In the same or different implementations, operation 634 may include an operation 637 for receiving the request for the one or more personalized plans, the request indicating one or more personal limitations associated with the end user as depicted in FIG. 6f. For instance, the request reception module 102* of the server 10 of FIG. 1b, the local source user device 20' of FIG. 2b, or the local end user device 30" of FIG. 3b receiving the request 12* for the one or more personalized plans 16*, the request 12* indicating one or more personal limitations (e.g., religious beliefs, dietary beliefs, phobias, personal prejudices, limitations related to personal experiences, personal work schedule obligations, family dynamics or circumstances, and so forth) associated with the end user 4*.

In the same or different implementations, operation 634 may include an operation 638 for receiving the request for the one or more personalized plans, the request indicating one or more medical or health limitations associated with the end user as depicted in FIG. 6f. For instance, the request reception module 102* of the server 10 of FIG. 1b, the local source user device 20' of FIG. 2b, or the local end user device 30" of FIG. 3b receiving the request 12* for the one or more personalized plans 16*, the request 12* indicating one or more medical or health limitations (e.g., medical limitations such as limitations resulting from an illness or treatment of an illness including physical limitations due to cancer or treatment of cancer, health limitations related to the physical conditioning of the end user 4*, genetic limitations, and so forth) associated with the end user 4*.

In the same or different implementations, operation 634 may include an operation 639 for receiving the request for the one or more personalized plans, the request indicating one or more user state limitations associated with the end user as depicted in FIG. 6f. For instance, the request reception module 102* of the server 10 of FIG. 1b, the local source user device 20' of FIG. 2b, or the local end user device 30" of FIG. 3b receiving the request 12* for the one or more personalized plans 16*, the request 12* indicating one or more user state limitations associated with the end user 4*(e.g., end user 4* is married, end user 4* is in mourning, end user 4* is unemployed, end user 4* is a vegan, and so forth).

In the same or different implementations, operation 634 may include an operation 640 for receiving the request for the one or more personalized plans, the request indicating one or more legal or regulatory limitations associated with the end user as depicted in FIG. 6f. For instance, the request reception module 102* of the server 10 of FIG. 1b, the local source user device 20' of FIG. 2b, or the local end user device 30" of FIG. 3b receiving the request 12* for the one or more personalized plans 16*, the request 12* indicating one or more legal or regulatory limitations associated with the end user 4*(e.g., drug regulations or laws, laws related to conduct or behavior in the jurisdiction of the end user 4*, and so forth).

Figure 7A:
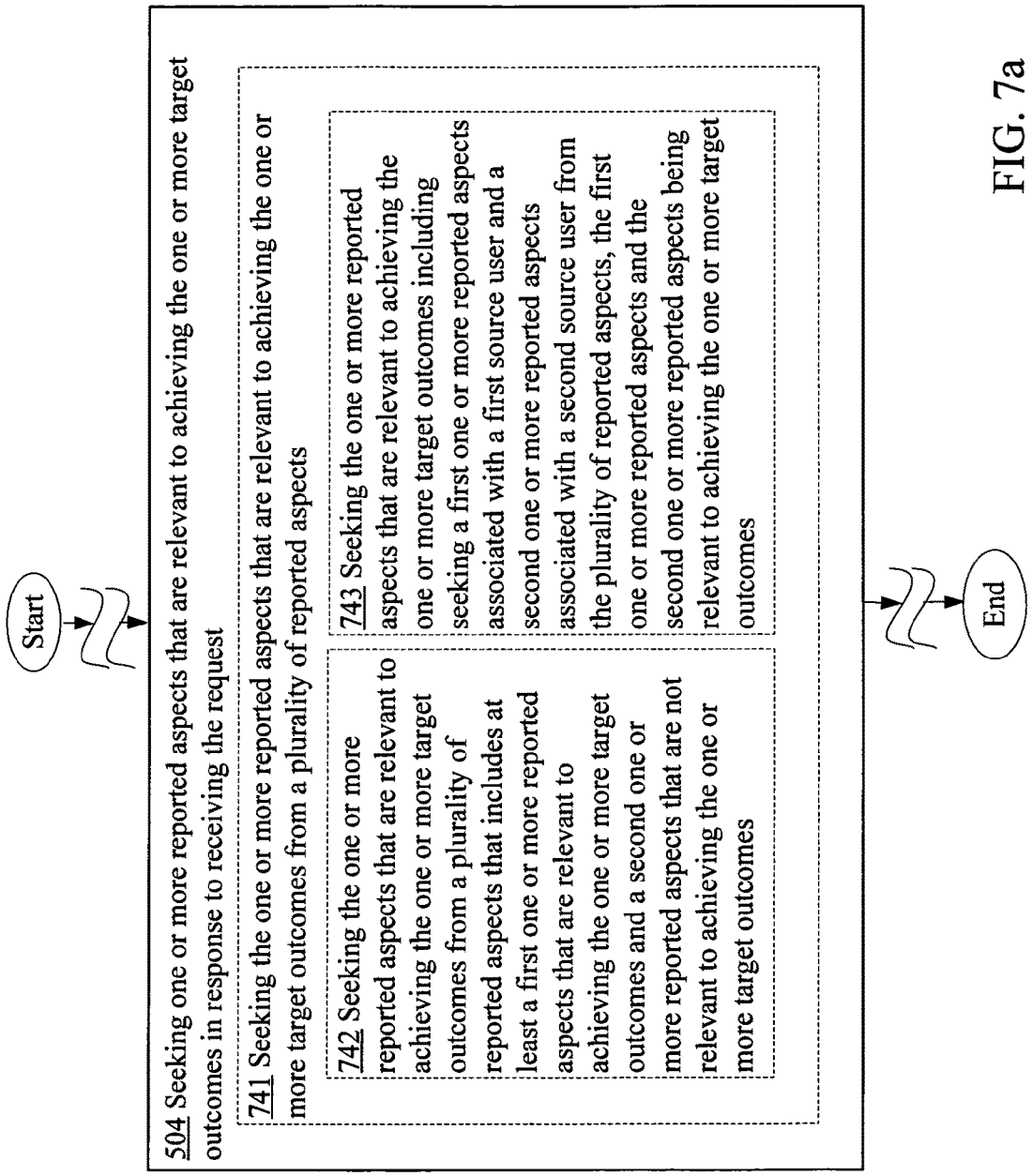
FIG. 7a is a high-level logic flowchart of a process depicting alternate implementations of the seeking operation 504 of FIG. 5.

Referring back to the seeking operation 504 of FIG. 5, the seeking operation 504 may be executed in a variety of different ways in various alternative implementations. For example, in some implementations, the seeking operation 504 may include an operation 741 for seeking the one or more reported aspects that are relevant to achieving the one or more target outcomes from a plurality of reported aspects as depicted in FIG. 7a. For instance, the reported aspect seeking module 104* of the server 10 of FIG. 1b, the local source user device 20' of FIG. 2b, or the local end user device 30" of FIG. 3b seeking the one or more reported aspects 14* that are relevant to achieving the one or more target outcomes from a plurality of reported aspects 15. For these implementations, the plurality of reported aspects 15 to be searched, which may include reported aspects associated with one or more source users 2* and which may include both reported aspects that may be relevant to achieving the one or more target outcomes and reported aspects that may not be relevant to achieving the one or more target outcomes, may be in memory 116* and/or at one or more remote network sites (e.g., in the case of the first exemplary environment of FIGS. 1a and 1b, one or more network servers 60 or one or more local source user devices 20).

In some implementations, operation 741 may include an operation 742 for seeking the one or more reported aspects that are relevant to achieving the one or more target outcomes from a plurality of reported aspects that includes at least a first one or more reported aspects that are relevant to achieving the one or more target outcomes and a second one or more reported aspects that are not relevant to achieving the one or more target outcomes as depicted in FIG. 7a. For instance, the reported aspect seeking module 104* of the server 10 of FIG. 1b, the local source user device 20' of FIG. 2b, or the local end user device 30" of FIG. 3b seeking the one or more reported aspects 14* that are relevant to achieving the one or more target outcomes from a plurality of reported aspects that includes at least a first one or more reported aspects that are relevant to achieving the one or more target outcomes and a second one or more reported aspects that are not relevant to achieving the one or more target outcomes.

In some implementations, operation 741 may include an operation 743 for seeking the one or more reported aspects that are relevant to achieving the one or more target outcomes including seeking a first one or more reported aspects associated with a first source user and a second one or more reported aspects associated with a second source user from the plurality of reported aspects, the first one or more reported aspects and the second one or more reported aspects being relevant to achieving the one or more target outcomes as depicted in FIG. 7a. For instance, the reported aspect seeking module 104* of the server 10 of FIG. 1b, the local source user device 20' of FIG. 2b, or the local end user device 30" of FIG. 3b seeking the one or more reported aspects 14* that are relevant to achieving the one or more target outcomes including seeking a first one or more reported aspects associated with a first source user 2a* and a second one or more reported aspects associated with a second source user 2b* from the plurality of reported aspects 15, the first one or more reported aspects and the second one or more reported aspects being relevant to achieving the one or more target outcomes. Thus, in operation 743 multiple reported aspects may be found that are associated with multiple source users.

Figure 7B:
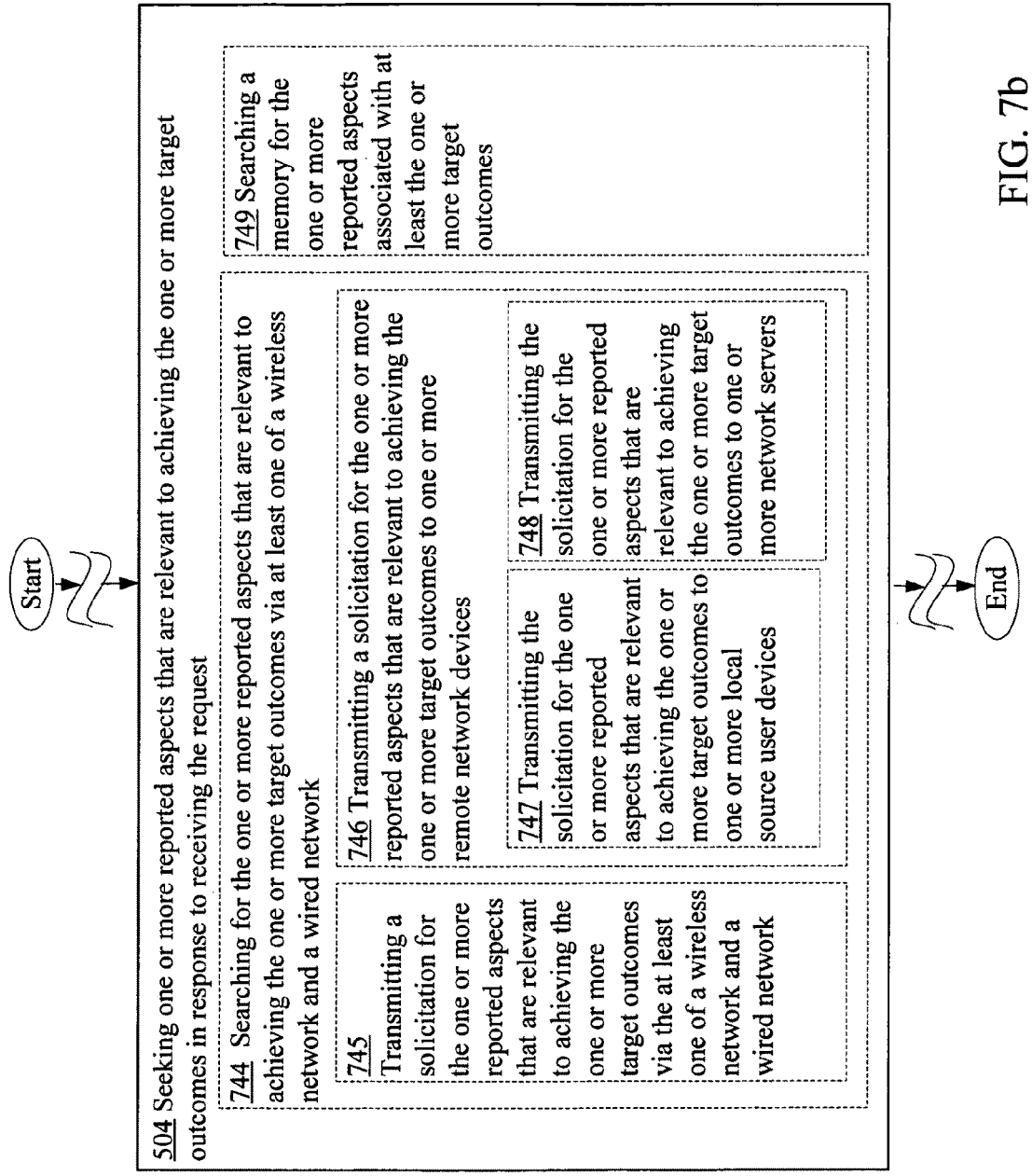
FIG. 7b is a high-level logic flowchart of a process depicting alternate implementations of the seeking operation 504 of FIG. 5.

In some implementations, the seeking operation 504 of FIG. 5 may include an operation 744 for searching for the one or more reported aspects that are relevant to achieving the one or more target outcomes via at least one of a wireless network and a wired network as depicted in FIG. 7b. For instance, the network searching module 204* of the server 10 of FIG. 1b, the local source user device 20' of FIG. 2b, or the local end user device 30" of FIG. 3b searching (e.g., transmitting an inquiry or a solicitation) for the one or more reported aspects 14* that are relevant to achieving the one or more target outcomes via at least one of a wireless network and a wired network 50*.

Operation 744 may in turn include one or more additional operations in various alternative implementations. For example, in some implementations, operation 744 may include an operation 745 for transmitting a solicitation for the one or more reported aspects that are relevant to achieving the one or more target outcomes via the at least one of a wireless network and a wired network as depicted in FIG. 7b. For instance, the solicitation transmission module 206*(see FIG. 4a) of the server 10 (of FIG. 1b), the local source user device 20' (of FIG. 2b), or the local end user device 30" (of FIG. 3b) transmitting a solicitation 13* for the one or more reported aspects 14* that are relevant to achieving the one or more target outcomes via the at least one of a wireless network and a wired network 50*.

In the same or different implementations, operation 744 may include an operation 746 for transmitting a solicitation for the one or more reported aspects that are relevant to achieving the one or more target outcomes to one or more remote network devices as depicted in FIG. 7b. For instance, the solicitation transmission module 206* of the server 10 (of FIG. 1b), the local source user device 20' (of FIG. 2b), or the local end user device 30" (of FIG. 3b) transmitting a solicitation 13* for the one or more reported aspects 14* that are relevant to achieving the one or more target outcomes to one or more remote network devices (e.g., in the embodiment depicted in FIGS. 1a and 1b, transmitting the solicitation 13 to one or more local source user devices 20, to one or more sensors 40, or to one or more network servers 60).

Operation 746 may, in turn, include an operation 747 for transmitting the solicitation for the one or more reported aspects that are relevant to achieving the one or more target outcomes to one or more local source user devices as depicted in FIG. 7b. For instance, the solicitation transmission module 206* of the server 10 (of FIG. 1b), the local source user device 20' (of FIG. 2b), or the local end user device 30" (of FIG. 3b) transmitting the solicitation 13* for the one or more reported aspects 14* that are relevant to achieving the one or more target outcomes to one or more local source user devices 20* (e.g., in the embodiment depicted in FIGS. 1a and 1b, the server 10 transmitting the solicitation 13 to one or more local source user devices 20).

In the same or different implementations, operation 746 may include an operation 748 for transmitting the solicitation for the one or more reported aspects that are relevant to achieving the one or more target outcomes to one or more network servers as depicted in FIG. 7b. For instance, the solicitation transmission module 206* of the server 10 (of FIG. 1b), the local source user device 20' (of FIG. 2b), or the local end user device 30" (of FIG. 3b) transmitting the solicitation 13* for the one or more reported aspects 14* that are relevant to achieving the one or more target outcomes to one or more network servers 60* (e.g., in the embodiment depicted in FIGS. 3a and 3b, the local end user device 30" transmitting the solicitation 13" to one or more network servers 60").

In various implementations, the seeking operation 504 of FIG. 5 may include an operation 749 for searching a memory for the one or more reported aspects associated with at least the one or more target outcomes as depicted in FIG. 7b. For instance, the memory searching module 208* of the server 10 of FIG. 1b, the local source user device 20' of FIG. 2b, or the local end user device 30" of FIG. 3b searching a memory 116* for the one or more reported aspects 14* associated with at least the one or more target outcomes.

One or more reported aspects 14* may be deemed to be relevant to the achievement of the one or more target outcomes based on a number of different factors including, for example, whether the one or more reported aspects 14* are associated with a specific source user 2* or a group of source users 2*. Such a source user 2* or group of source users 2* may have been identified by, for example, the end user 4* or by one or more third parties 6*, or may be further associated with, for example, one or more reported outcomes that corresponds to the one or more target outcomes (e.g., in other words, whether the reported aspects 14* are associated with a specific user or a group of source users who have reported (e.g., via reported outcomes) that they have achieved the one or more target outcomes).

Figure 7C:
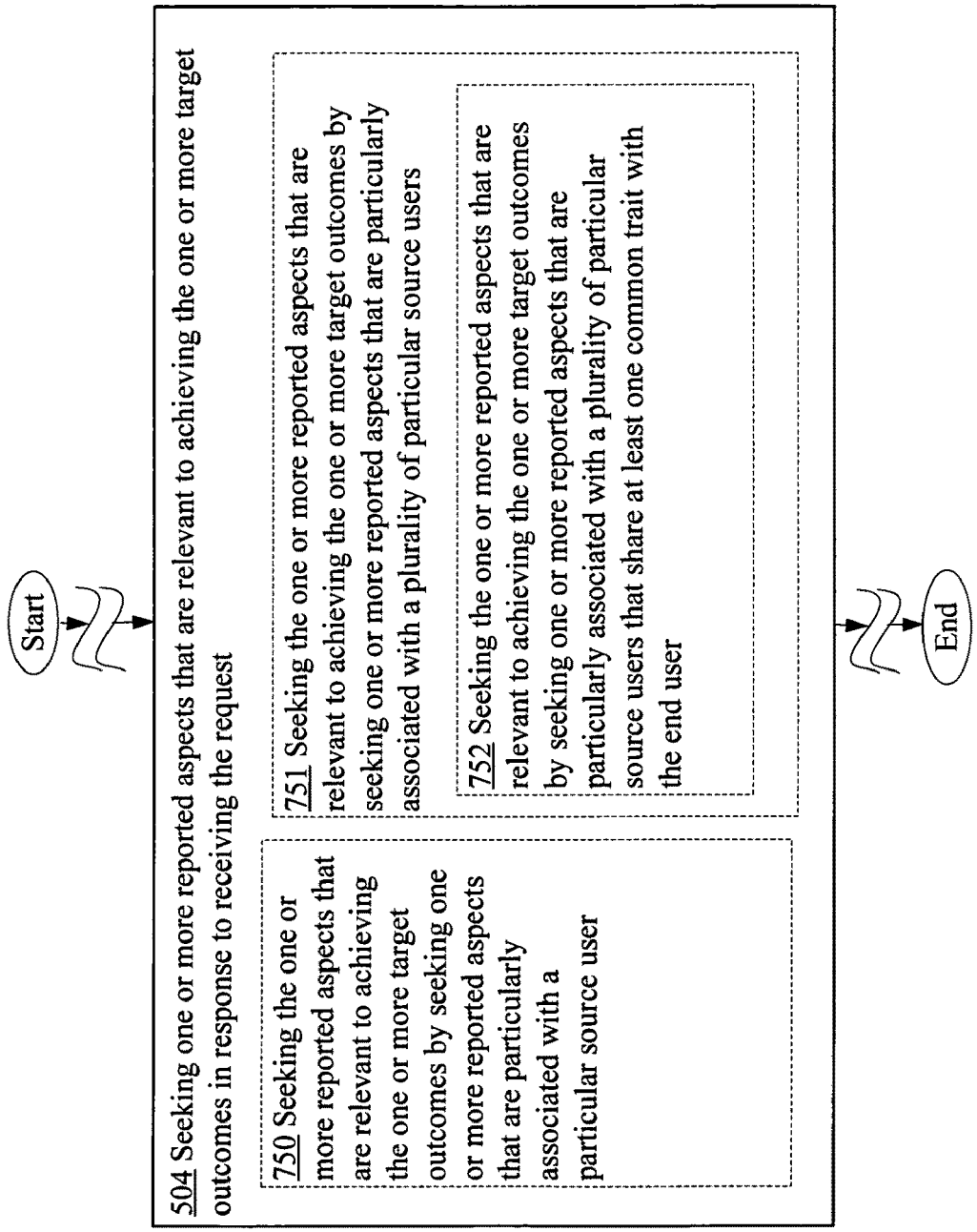
FIG. 7c is a high-level logic flowchart of a process depicting alternate implementations of the seeking operation 504 of FIG. 5.

For example, in some implementations, the seeking operation 504 of FIG. 5 may include an operation 750 for seeking the one or more reported aspects that are relevant to achieving the one or more target outcomes by seeking one or more reported aspects that are particularly associated with a particular source user as depicted in FIG. 7c. For instance, the reported aspect seeking module 104* of the server 10 of FIG. 1b, the local source user device 20' of FIG. 2b, or the local end user device 30" of FIG. 3b seeking the one or more reported aspects 14* that are relevant to achieving the one or more target outcomes by seeking one or more reported aspects 14* that are particularly associated with a particular source user (e.g., source user 2a* or source user 2b*).

In various implementations, the seeking operation 504 may include an operation 751 for seeking the one or more reported aspects that are relevant to achieving the one or more target outcomes by seeking one or more reported aspects that are particularly associated with a plurality of particular source users as depicted in FIG. 7c. For instance, the reported aspect seeking module 104* of the server 10 of FIG. 1b, the local source user device 20' of FIG. 2b, or the local end user device 30" of FIG. 3b seeking the one or more reported aspects 14* that are relevant to achieving the one or more target outcomes by seeking one or more reported aspects 14* that are particularly associated with a plurality of particular source users (e.g., source users 2*).

In some implementations, operation 751 may further include an operation 752 for seeking the one or more reported aspects that are relevant to achieving the one or more target outcomes by seeking one or more reported aspects that are particularly associated with a plurality of particular source users that share at least one common trait with the end user as depicted in FIG. 7c. For instance, the reported aspect seeking module 104* of the server 10 of FIG. 1b, the local source user device 20' of FIG. 2b, or the local end user device 30" of FIG. 3b seeking the one or more reported aspects that are relevant to achieving the one or more target outcomes by seeking one or more reported aspects 14* that are particularly associated with a plurality of particular source users (e.g., source users 2*) that share at least one common trait (e.g., physical characteristic, physical handicap, illness, ethnic, religious, or cultural belief, and so forth) with the end user 4*.

Figure 7D:
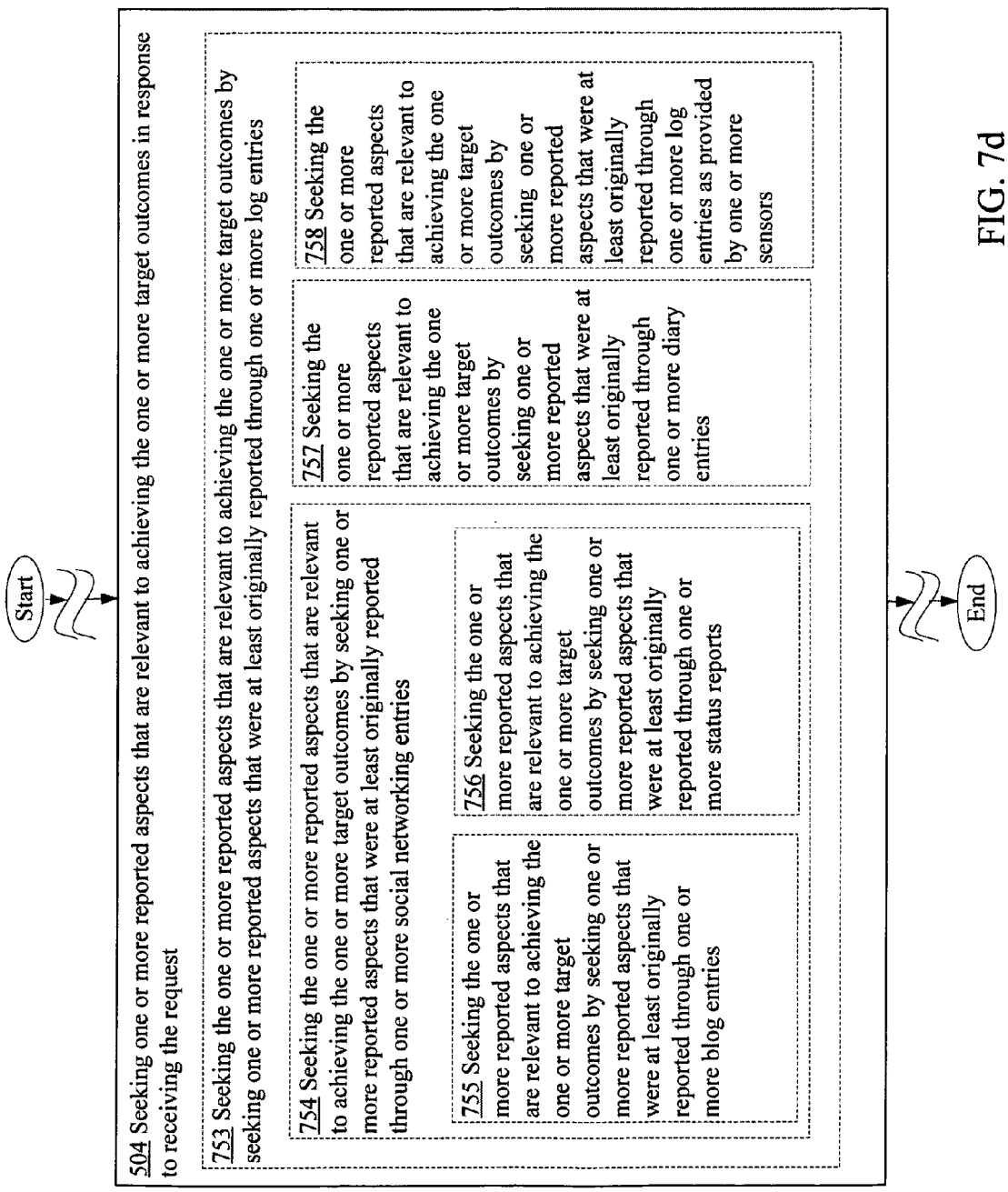
FIG. 7d is a high-level logic flowchart of a process depicting alternate implementations of the seeking operation 504 of FIG. 5.

The one or more reported aspects 14 to be found through the seeking operation 504 of FIG. 5 may have been at least originally reported via various means. For example, in some implementations, the seeking operation 504 of FIG. 5 may include an operation 753 for seeking the one or more reported aspects that are relevant to achieving the one or more target outcomes by seeking one or more reported aspects that were at least originally reported through one or more log entries as depicted in FIG. 7d. For instance, the reported aspect seeking module 104* of the server 10 of FIG. 1b, the local source user device 20' of FIG. 2b, or the local end user device 30" of FIG. 3b seeking the one or more reported aspects 14* that are relevant to achieving the one or more target outcomes by seeking one or more reported aspects 14* that were at least originally reported through one or more log entries (e.g., electronic log entries as entered by, for example, a source user 2* or a sensor 40*).

In various implementations, operation 753 may further include one or more additional operations. For example, in some implementations, operation 753 may include an operation 754 for seeking the one or more reported aspects that are relevant to achieving the one or more target outcomes by seeking one or more reported aspects that were at least originally reported through one or more social networking entries as depicted in FIG. 7d. For instance, the reported aspect seeking module 104* of the server 10 of FIG. 1b, the local source user device 20' of FIG. 2b, or the local end user device 30" of FIG. 3b seeking the one or more reported aspects 14* that are relevant to achieving the one or more target outcomes by seeking one or more reported aspects 14* that were at least originally reported through one or more social networking entries.

The one or more reported aspects 14* to be found through operation 754 may have been originally reported via various social networking means. For example, in some implementations, operation 754 may include an operation 755 for seeking the one or more reported aspects that are relevant to achieving the one or more target outcomes by seeking one or more reported aspects that were at least originally reported through one or more blog entries as depicted in FIG. 7d. For instance, the reported aspect seeking module 104* of the server 10 of FIG. 1b, the local source user device 20' of FIG. 2b, or the local end user device 30" of FIG. 3b seeking the one or more reported aspects 14* that are relevant to achieving the one or more target outcomes by seeking one or more reported aspects 14* that were at least originally reported through one or more blog entries (e.g., microblog entries).

In some implementations, operation 754 may include an operation 756 for seeking the one or more reported aspects that are relevant to achieving the one or more target outcomes by seeking one or more reported aspects that were at least originally reported through one or more status reports as depicted in FIG. 7d. For instance, the reported aspect seeking module 104* of the server 10 of FIG. 1b, the local source user device 20' of FIG. 2b, or the local end user device 30" of FIG. 3b seeking the one or more reported aspects 14* that are relevant to achieving the one or more target outcomes by seeking one or more reported aspects 14* that were at least originally reported through one or more status reports.

In various implementations, operation 753 may include an operation 757 for seeking the one or more reported aspects that are relevant to achieving the one or more target outcomes by seeking one or more reported aspects that were at least originally reported through one or more diary entries as depicted in FIG. 7d. For instance, the reported aspect seeking module 104* of the server 10 of FIG. 1b, the local source user device 20' of FIG. 2b, or the local end user device 30" of FIG. 3b seeking the one or more reported aspects 14* that are relevant to achieving the one or more target outcomes by seeking one or more reported aspects 14* that were at least originally reported through one or more diary entries, which in some cases may be stored in a memory 116*.

In some implementations, operation 753 may include an operation 758 for seeking the one or more reported aspects that are relevant to achieving the one or more target outcomes by seeking one or more reported aspects that were at least originally reported through one or more log entries as provided by one or more sensors as depicted in FIG. 7d. For instance, the reported aspect seeking module 104* of the server 10 of FIG. 1b, the local source user device 20' of FIG. 2b, or the local end user device 30" of FIG. 3b seeking the one or more reported aspects 14* that are relevant to achieving the one or more target outcomes by seeking one or more reported aspects 14* that were at least originally reported through one or more log entries as provided by one or more sensors 40* (e.g., physiological sensors such as heart rate monitors or blood glucose meter, user activity sensors such as those that detect a user's toilet use or sensors that detects exercise activities of a user such as a pedometer, and so forth).

Figure 7E:
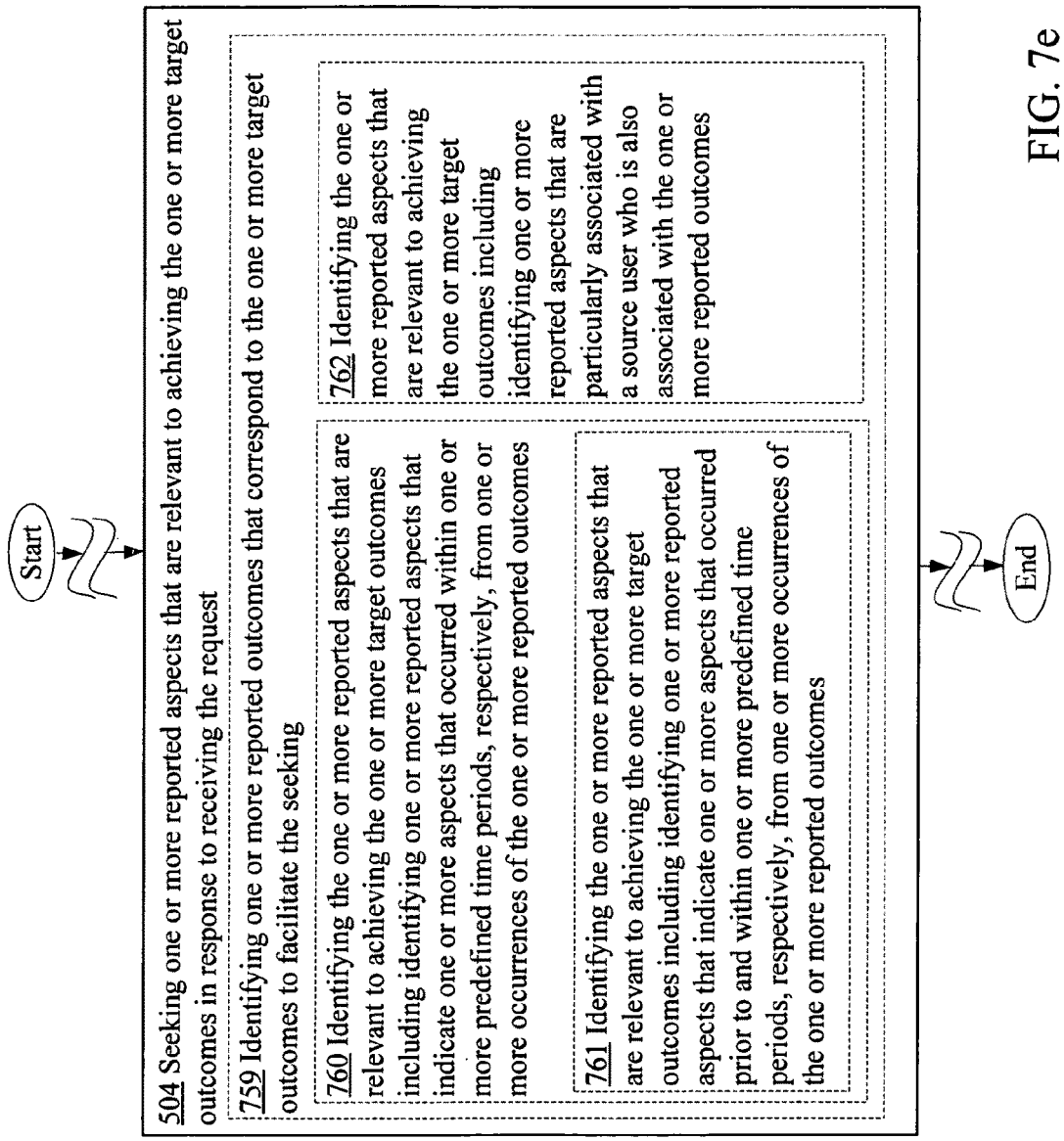
FIG. 7e is a high-level logic flowchart of a process depicting alternate implementations of the seeking operation 504 of FIG. 5.

In order to seek the one or more reported aspects 14* that are relevant to achieving the one or more target outcomes, one or more reported outcomes that corresponds to the one or more target outcomes may be initially identified. For example, in some implementations, the seeking operation 504 of FIG. 5 may include an operation 759 for identifying one or more reported outcomes that correspond to the one or more target outcomes to facilitate the seeking as depicted in FIG. 7e. For instance, the reported outcome identification module 210* (see FIG. 4a) of the server 10 of FIG. 1b, the local source user device 20' of FIG. 2b, or the local end user device 30" of FIG. 3b identifying one or more reported outcomes that correspond to the one or more target outcomes to facilitate the seeking.

In various implementations, once the one or more reported outcomes that correspond to the one or more target outcomes have been identified, other operations may be executed. For example, in some implementations, operation 759 may further include an operation 760 for identifying the one or more reported aspects that are relevant to achieving the one or more target outcomes including identifying the one or more reported aspects that indicates one or more aspects that occurred within one or more predefined time periods, respectively, from one or more occurrences of the one or more reported outcomes as depicted in FIG. 7e. For instance, the reported aspect identification module 212* (see FIG. 4a) of the server 10 of FIG. 1b, the local source user device 20' of FIG. 2b, or the local end user device 30" of FIG. 3b identifying the one or more reported aspects 14* (e.g., dietary behavior) that are relevant to achieving the one or more target outcomes (e.g., losing 20 pounds of weight) including identifying one or more reported aspects 14* that indicates one or more aspects that occurred within one or more predefined time periods (e.g., two months), respectively, from one or more occurrences of the one or more reported outcomes. As a further example, the reported aspect identification module 212* identifying one or more reported aspects 14* related to the dietary behavior (e.g., eating behavior) of one or more source users 2* and that occurred within two months of occurrences of 20 pounds of weight loss (e.g., reported outcomes or target outcomes) reported by the one or more source users 2*.

In some implementations, operation 760 may further include an operation 761 for identifying the one or more reported aspects that are relevant to achieving the one or more target outcomes including identifying the one or more reported aspects that indicates one or more aspects that occurred prior to and within one or more predefined time periods, respectively, from one or more occurrences of the one or more reported outcomes as depicted in FIG. 7e. For instance, the reported aspect identification module 212* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported aspects 14* that indicates one or more aspects that occurred prior to and within one or more predefined time periods, respectively, from one or more occurrences of the one or more reported outcomes. As a further example, suppose an end user 4* is interested in the dietary behaviors of those who have lost a total of 20 pounds of weight loss during the two months preceding the weight loss. The reported aspect identification module 212* may then identify one or more reported aspects 14* that are related to the dietary behavior (e.g., eating behavior) of one or more source users 2* that occurred prior to and within two months of occurrences of 20 pounds of weight loss (e.g., reported outcomes or target outcomes) reported by the one or more source users 2*.

In some implementations, operation 759 may include an operation 762 for identifying the one or more reported aspects that are relevant to achieving the one or more target outcomes including identifying one or more reported aspects that are particularly associated with a source user who is also associated with the one or more reported outcomes as depicted in FIG. 7e. For instance, the reported aspect identification module 212* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported aspects 14* that are particularly associated with a source user 2* who is also associated with the one or more reported outcomes. As a further example, the reported aspect identification module 212* identifying one or more reported aspects 14* that are particularly associated with a source user 2a* (e.g., reading one book per week by the source user 2a*) who is also associated with the one or more reported outcomes (e.g., improve SAT reading score).

Figure 7F:
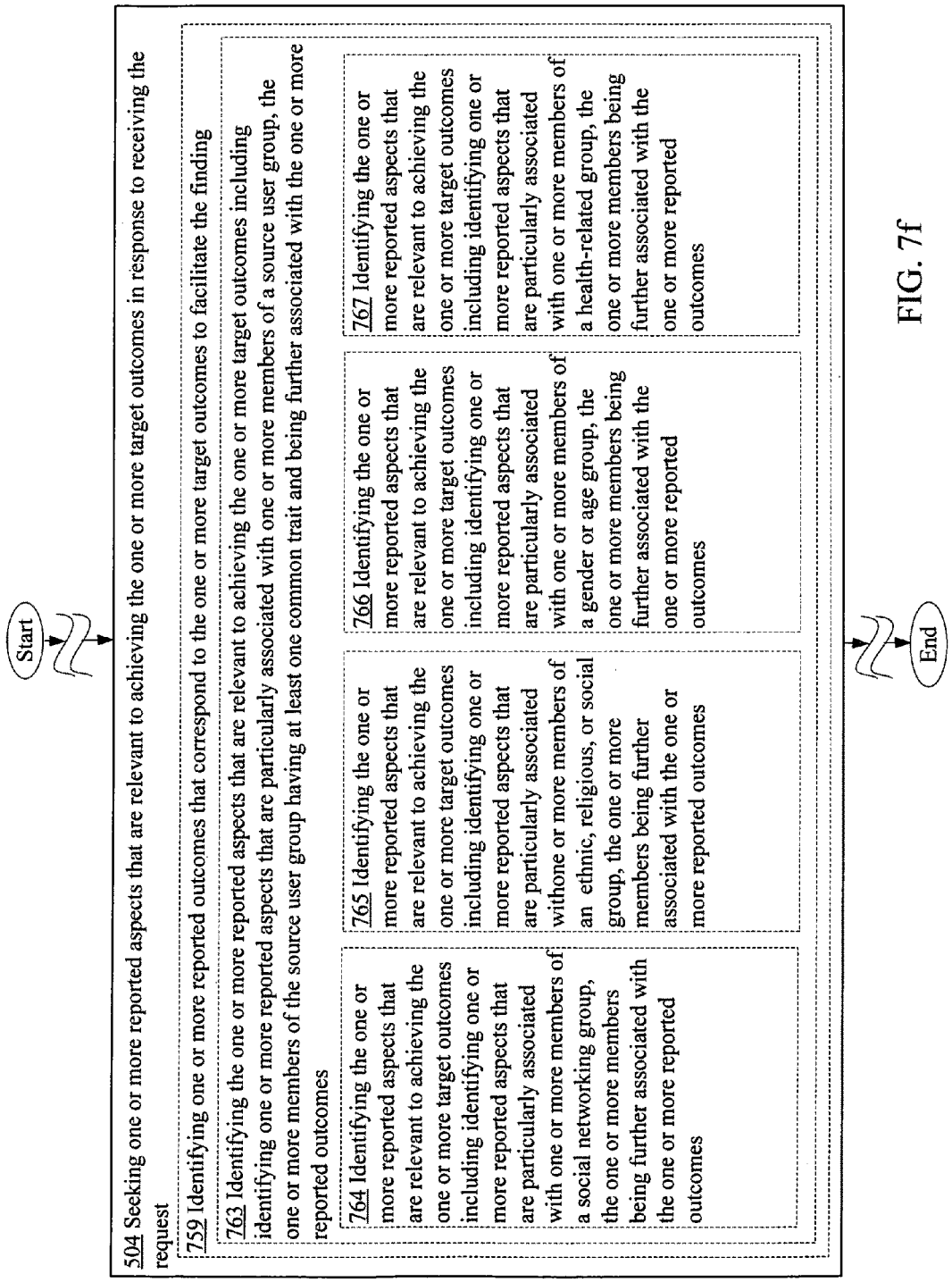
FIG. 7f is a high-level logic flowchart of a process depicting alternate implementations of the seeking operation 504 of FIG. 5.

In various alternative implementations, operation 759 for identifying one or more reported outcomes may further include one or more operations to identify one or more reported aspects 14 that are associated with one or more members of a source user group. For example, in various implementations, operation 759 may include an operation 763 for identifying the one or more reported aspects that are relevant to achieving the one or more target outcomes including identifying one or more reported aspects that are particularly associated with one or more members of a source user group, the one or more members of the source user group having at least one common trait and being further associated with the one or more reported outcomes as depicted in FIG. 7f. For instance, the reported aspect identification module 212* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported aspects 14* that are particularly associated with one or more members of a source user group (e.g., social networking group, ethnic, cultural, or religious groups, health group, belief groups, and so forth), the one or more members of the source user group having at least one common trait and being further associated with the one or more reported outcomes.

In some implementations, operation 763 may include an operation 764 for identifying the one or more reported aspects that are relevant to achieving the one or more target outcomes including identifying one or more reported aspects that are particularly associated with one or more members of a social networking group, the one or more members being further associated with the one or more reported outcomes as depicted in FIG. 7f. For instance, the reported aspect identification module 212* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported aspects 14* that are particularly associated with one or more members of a social networking group, the one or more members being further associated with the one or more reported outcomes. As a further illustration, the reported aspect identification module 212* identifying reported aspects (e.g., study habits) that are particularly associated with members of a social networking group (e.g., classmates), the members being further associated with the one or more reported outcomes (e.g., passing a calculus exam) that corresponds to the one or more target outcomes.

In some implementations, operation 763 may include an operation 765 for identifying the one or more reported aspects that are relevant to achieving the one or more target outcomes including identifying one or more reported aspects that are particularly associated with one or more members of an ethnic, religious, or social group, the one or more members being further associated with the one or more reported outcomes as depicted in FIG. 7f. For instance, the reported aspect identification module 212* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported aspects 14* (e.g., relatively low white rice consumption) that are particularly associated with one or more members of an ethnic, religious, or social group (e.g., Asian ancestry), the one or more members being further associated with the one or more reported outcomes (e.g., low blood glucose levels).

In some implementations, operation 763 may include an operation 766 for identifying the one or more reported aspects that are relevant to achieving the one or more target outcomes including identifying one or more reported aspects that are particularly associated with one or more members of a gender or age group, the one or more members being further associated with the one or more reported outcomes as depicted in FIG. 7f. For instance, the reported aspect identification module 212* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported aspects 14* (e.g., Omega-3 consumption) that are particularly associated with one or more members of a gender or age group (e.g., over 65 years of age), the one or more members being further associated with the one or more reported outcomes (e.g., reduced arthritic conditions).

In some implementations, operation 763 may include an operation 767 for identifying the one or more reported aspects that are relevant to achieving the one or more target outcomes including identifying one or more reported aspects that are particularly associated with one or more members of a health-related group, the one or more members being further associated with the one or more reported outcomes as depicted in FIG. 7f. For instance, the reported aspect identification module 212* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported aspects 14* (e.g., marijuana usage) that are particularly associated with one or more members of a health-related group (e.g., cancer patients being treated by chemotherapy), the one or more members being further associated with the one or more reported outcomes (e.g., reduction in nausea).

Figure 7G:
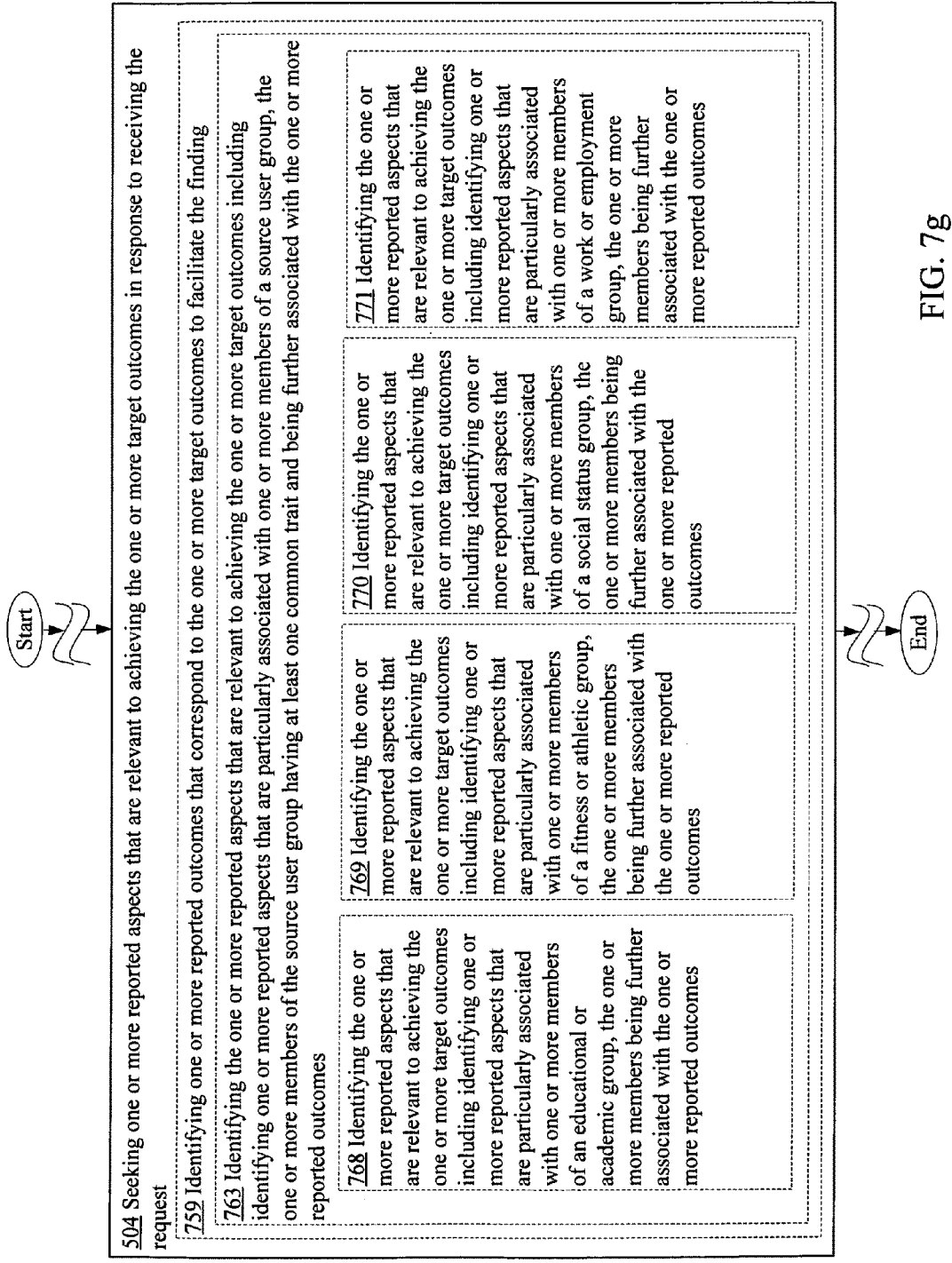
FIG. 7g is a high-level logic flowchart of a process depicting alternate implementations of the seeking operation 504 of FIG. 5.

In some implementations, operation 763 may include an operation 768 for identifying the one or more reported aspects that are relevant to achieving the one or more target outcomes including identifying one or more reported aspects that are particularly associated with one or more members of an educational or academic group, the one or more members being further associated with the one or more reported outcomes as depicted in FIG. 7g. For instance, the reported aspect identification module 212* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported aspects 14* (e.g., being tutored by a particular tutor) that are particularly associated with one or more members of an educational or academic group (e.g., students at a particular engineering school) the one or more members being further associated with the one or more reported outcomes (e.g., understanding thermodynamics).

In some implementations, operation 763 may include an operation 769 for identifying the one or more reported aspects that are relevant to achieving the one or more target outcomes including identifying one or more reported aspects that are particularly associated with one or more members of a fitness or athletic group, the one or more members being further associated with the one or more reported outcomes as depicted in FIG. 7g. For instance, the reported aspect identification module 212* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported aspects 14* (e.g., amount of sit-ups done daily) that are particularly associated with one or more members of a fitness or athletic group (e.g., members of a particular gym), the one or more members being further associated with the one or more reported outcomes (e.g., 28 inch waist).

In some implementations, operation 763 may include an operation 770 for identifying the one or more reported aspects that are relevant to achieving the one or more target outcomes including identifying one or more reported aspects that are particularly associated with one or more members of a social status group, the one or more members being further associated with the one or more reported outcomes as depicted in FIG. 7g. For instance, the reported aspect identification module 212* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported aspects 14* (e.g., behavior towards a boyfriend) that are particularly associated with one or more members of a social status group (e.g., single women), the one or more members being further associated with the one or more reported outcomes (e.g., diamond ring).

In some implementations, operation 763 may include an operation 771 for identifying the one or more reported aspects that are relevant to achieving the one or more target outcomes including identifying one or more reported aspects that are particularly associated with one or more members of a work or employment group, the one or more members being further associated with the one or more reported outcomes as depicted in FIG. 7g. For instance, the reported aspect identification module 212* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported aspects 14* (e.g., attendance at company functions) that are particularly associated with one or more members of a work or employment group (e.g., employees at the same company), the one or more members being further associated with the one or more reported outcomes (e.g., promotion to managerial position).

Figure 7H:
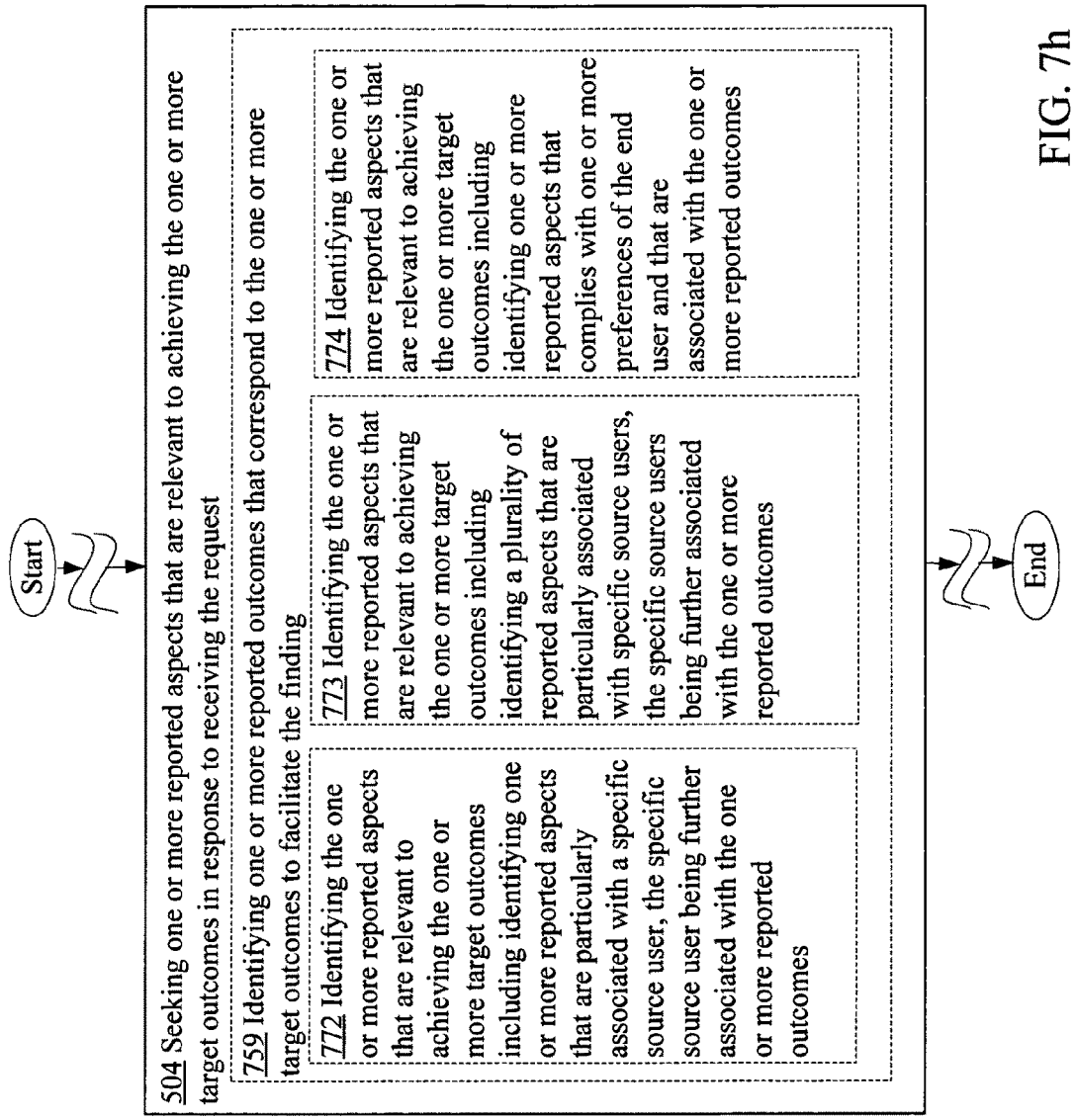
FIG. 7h is a high-level logic flowchart of a process depicting alternate implementations of the seeking operation 504 of FIG. 5.

In various implementations, operation 759 of FIGS. 7e, 7f, and 7g may include an operation 772 for identifying the one or more reported aspects that are relevant to achieving the one or more target outcomes including identifying one or more reported aspects that are particularly associated with a specific source user, the specific source user being further associated with the one or more reported outcomes as depicted in FIG. 7h. For instance, the reported aspect identification module 212* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported aspects 14* (e.g., sleep behavior) that are particularly associated with a specific source user 2a*, the specific source user 2a* being further associated with the one or more reported outcomes (e.g., feeling alert and energetic).

In some implementations, operation 759 may include an operation 773 for identifying the one or more reported aspects that are relevant to achieving the one or more target outcomes including identifying a plurality of reported aspects that are particularly associated with specific source users, the specific source users being further associated with the one or more reported outcomes as depicted in FIG. 7h. For instance, the reported aspect identification module 212* of the server 10 of FIG. 1b, the local source user device 20' of FIG. 2b, or the local end user device 30" of FIG. 3b identifying the one or more reported aspects 14* that are relevant to achieving the one or more target outcomes including identifying a plurality of reported aspects 14* (e.g., positive outlook) that are particularly associated with specific source users 2* (e.g., formerly unemployed workers), the specific source users 2* being further associated with the one or more reported outcomes (e.g., getting a job or having a successful job interview).

In various implementations, the one or more reported aspects 14* to be found through the seeking operation 504 of FIG. 5 may include one or more reported aspects 14* that may comply with one or more preferences and/or limitations of the end user 4*. For example, in some implementations, operation 759 may include an operation 774 for identifying the one or more reported aspects that are relevant to achieving the one or more target outcomes including identifying one or more reported aspects that complies with one or more preferences of the end user and that are associated with the one or more reported outcomes as depicted in FIG. 7h. For instance, the preference compliant reported aspect identification module 213* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported aspects 14* that complies with one or more preferences (e.g., types of reported aspects that are of interest) of the end user 4* and that are associated with the one or more reported outcomes. For example, the end user 4* may only be interested in the sleep patterns of source users 2* who have lost 30 pounds of weight (e.g., target outcome). Under such circumstances, the preference compliant reported aspect identification module 213* may only be configured to identify those reported aspects 14* that relate to sleep activities. Thus, for these implementations, the preference compliant reported aspect identification module 213* may be designed to only identify the types of reported aspects that the end user 4* may have an interest in with respect to the achievement of the one or more target outcomes.

Figure 7I:
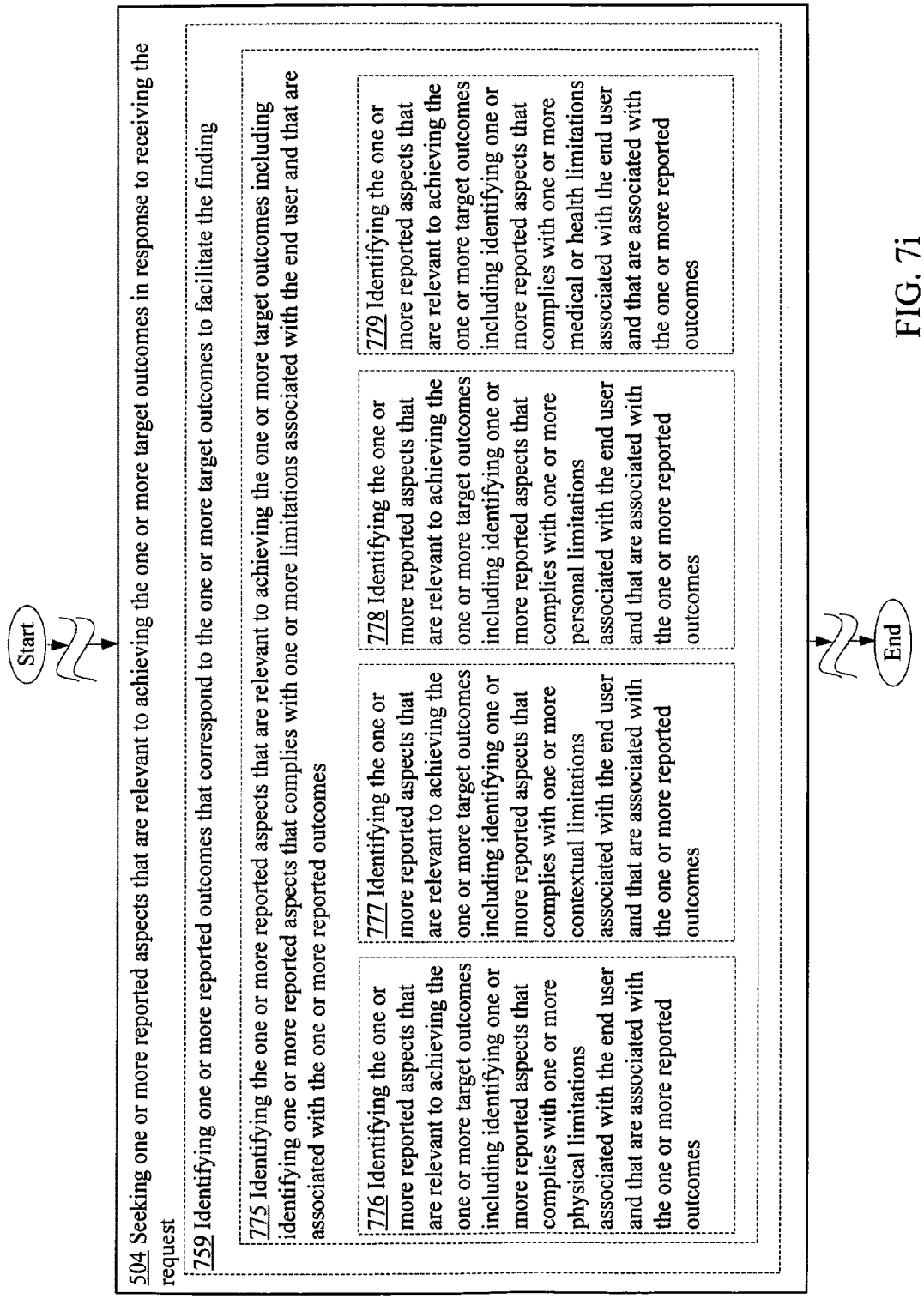
FIG. 7i is a high-level logic flowchart of a process depicting alternate implementations of the seeking operation 504 of FIG. 5.

Alternatively or in the same implementations, operation 759 may include an operation 775 for identifying the one or more reported aspects that are relevant to achieving the one or more target outcomes including identifying one or more reported aspects that complies with one or more limitations associated with the end user and that are associated with the one or more reported outcomes as depicted in FIG. 7i. For instance, the limitation compliant reported aspect identification module 214* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported aspects 14* that complies with (e.g., does not violate) one or more limitations associated with the end user 4* (e.g., end user 4* is a vegan, end user 4* has a physical handicap that prevents her from participating in certain activities, end user 4* lives in Singapore so does not have access to chewing gum, and so forth) and that are associated with the one or more reported outcomes.

Operation 775 may, in turn, include one or more additional operations in various alternative implementations. For example, in some implementations, operation 775 may include an operation 776 for identifying the one or more reported aspects that are relevant to achieving the one or more target outcomes including identifying one or more reported aspects that complies with one or more physical limitations associated with the end user and that are associated with the one or more reported outcomes as depicted in FIG. 7i. For instance, the limitation compliant reported aspect identification module 214* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported aspects 14* that complies with one or more physical limitations (e.g., visual handicap, hearing handicap, missing limbs or paralysis, and so forth) associated with the end user 4* and that are associated with the one or more reported outcomes.

In some implementations, operation 775 may include an operation 777 for identifying the one or more reported aspects that are relevant to achieving the one or more target outcomes including identifying one or more reported aspects that complies with one or more contextual limitations associated with the end user and that are associated with the one or more reported outcomes as depicted in FIG. 7i. For instance, the limitation compliant reported aspect identification module 214* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported aspects 14* that complies with one or more contextual limitations (e.g., logistical limitations such as the geographical location of the end user 4* that prevents the end user 4* from participating in certain activities or work or family situations that prevents the end user 4* from participating in certain activities) associated with the end user 4* and that are associated with the one or more reported outcomes.

In some implementations, operation 775 may include an operation 778 for identifying the one or more reported aspects that are relevant to achieving the one or more target outcomes including identifying one or more reported aspects that complies with one or more personal limitations associated with the end user and that are associated with the one or more reported outcomes as depicted in FIG. 7i. For instance, the limitation compliant reported aspect identification module 214* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported aspects 14* that complies with one or more personal limitations (e.g., limitations related to religious beliefs, spiritual beliefs, phobias, personal beliefs such as avoidance of fluoride, and so forth) associated with the end user 4* and that are associated with the one or more reported outcomes.

In some implementations, operation 775 may include an operation 779 for identifying the one or more reported aspects that are relevant to achieving the one or more target outcomes including identifying one or more reported aspects that complies with one or more medical or health limitations associated with the end user and that are associated with the one or more reported outcomes as depicted in FIG. 7i. For instance, the limitation compliant reported aspect identification module 214* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported aspects 14* that complies with one or more medical or health limitations (e.g., limitations related to arthritis, diabetes, cardiovascular conditions, and so forth) associated with the end user 4* and that are associated with the one or more reported outcomes.

Figure 7J:
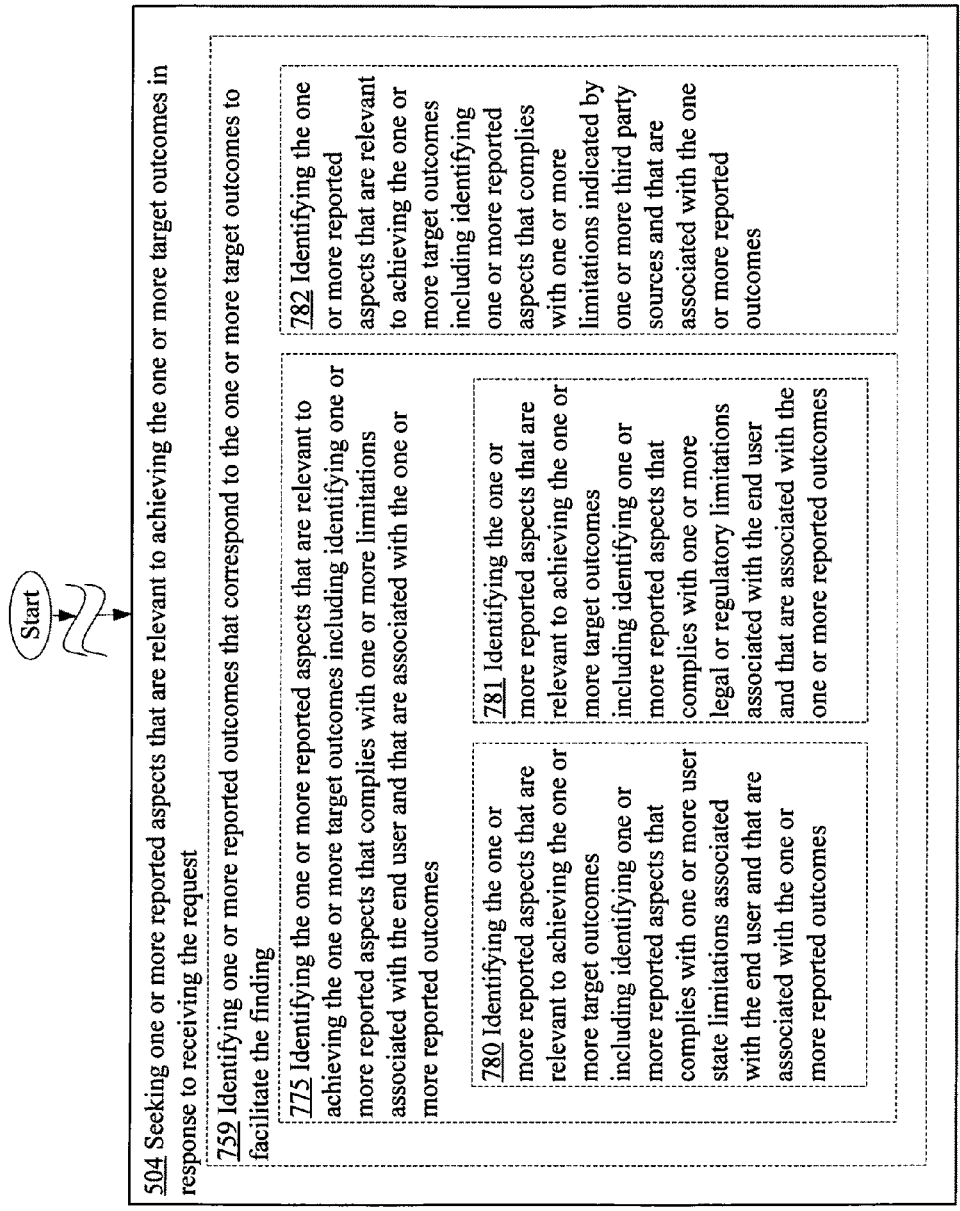
FIG. 7j is a high-level logic flowchart of a process depicting alternate implementations of the seeking operation 504 of FIG. 5.

In some implementations, operation 775 may further include an operation 780 for identifying the one or more reported aspects that are relevant to achieving the one or more target outcomes including identifying one or more reported aspects that complies with one or more user state limitations associated with the end user and that are associated with the one or more reported outcomes as depicted in FIG. 7j. For instance, the limitation compliant reported aspect identification module 214* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported aspects 14* that complies with one or more user state limitations (e.g., marital status, employment status, mental state, and so forth) associated with the end user 4* and that are associated with the one or more reported outcomes.

In some implementations, operation 775 may further include an operation 781 for identifying the one or more reported aspects that are relevant to achieving the one or more target outcomes including identifying one or more reported aspects that complies with one or more legal or regulatory limitations associated with the end user and that are associated with the one or more reported outcomes as depicted in FIG. 7j. For instance, the limitation compliant reported aspect identification module 214* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported aspects 14* that complies with one or more legal or regulatory limitations associated with the end user 4* (e.g., drug or food regulations related to the place of domicile of the end user 4*) and that are associated with the one or more reported outcomes.

In some instances, the one or more reported aspects 14* to be found through the seeking operation 504 may be identified as being compliant with one or more limitations as set forth by one or more third parties 6*. For example, in various implementations, operation 759 may include an operation 782 for identifying the one or more reported aspects that are relevant to achieving the one or more target outcomes including identifying one or more reported aspects that complies with one or more limitations indicated by one or more third party sources and that are associated with the one or more reported outcomes as depicted in FIG. 7j. For instance, the limitation compliant reported aspect identification module 214* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported aspects 14* that complies with one or more limitations indicated by one or more third party sources (e.g., publications, research results, medical advisories, and so forth) and that are associated with the one or more reported outcomes.

Figure 7K:
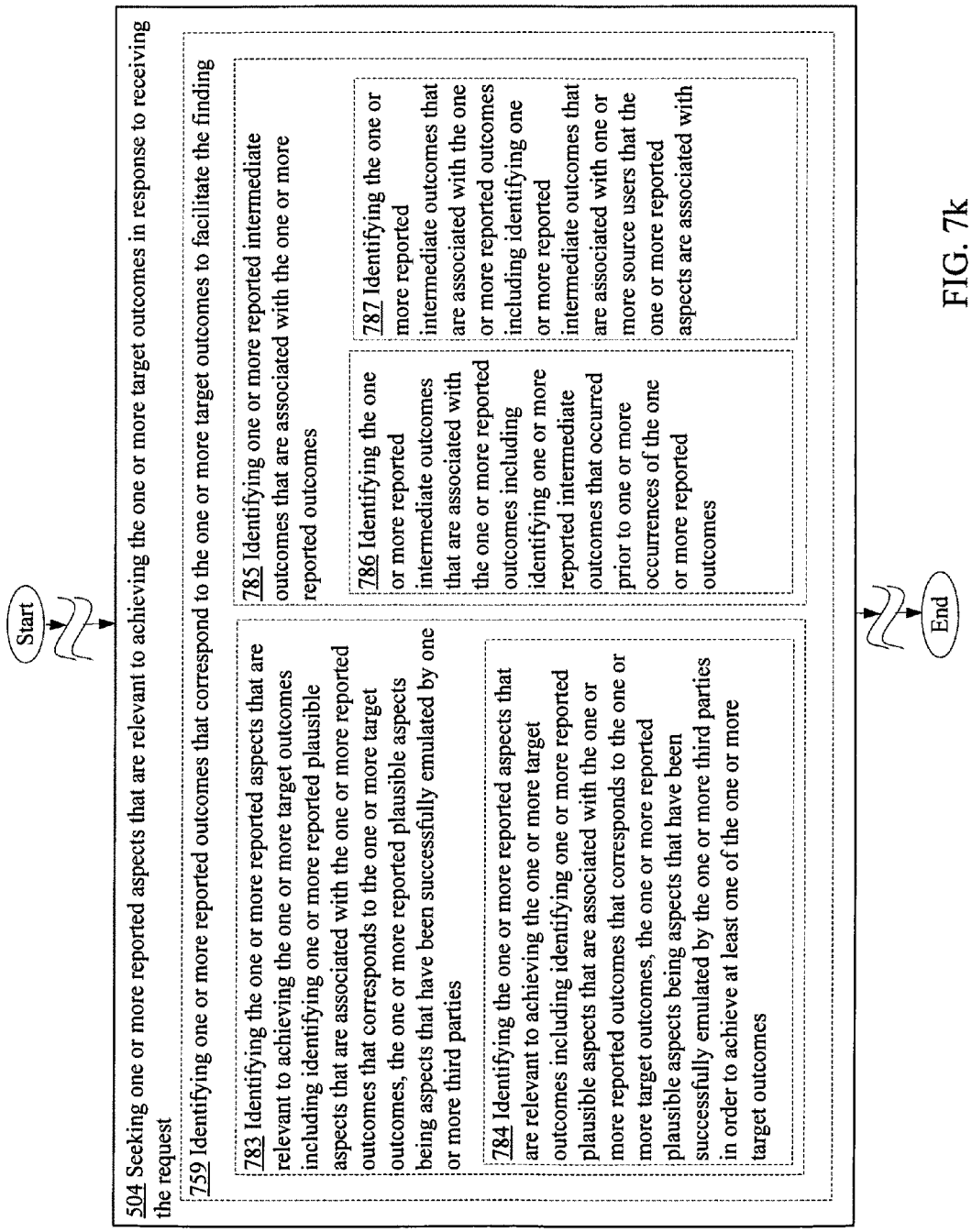
FIG. 7k is a high-level logic flowchart of a process depicting alternate implementations of the seeking operation 504 of FIG. 5.
Figure 71:
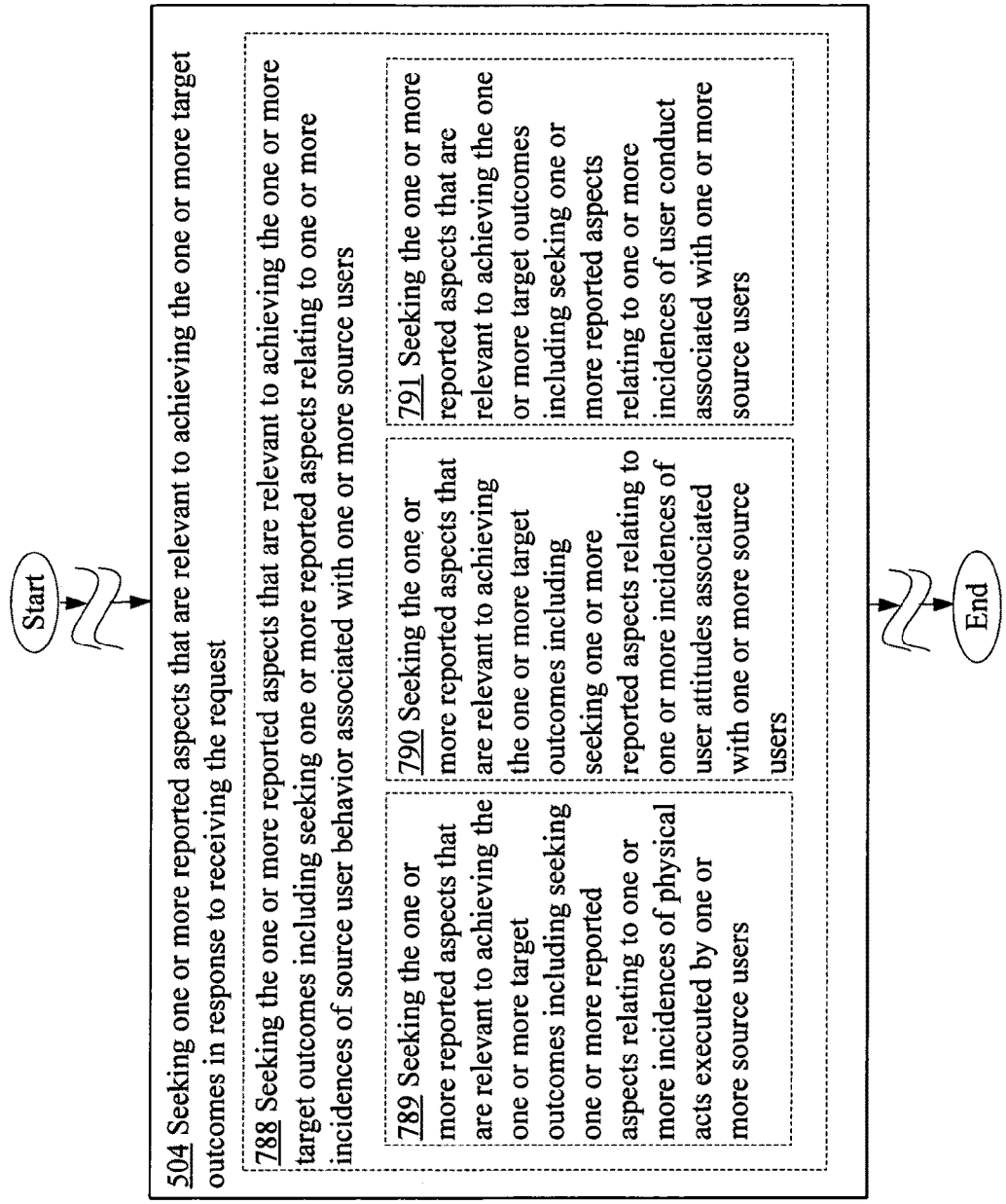

In some cases, the one or more reported aspects 14* to be sought may be identified as being one or more reported plausible aspects. For example, in some embodiments, operation 759 may include an operation 783 for identifying the one or more reported aspects that are relevant to achieving the one or more target outcomes including identifying one or more reported plausible aspects that are associated with the one or more reported outcomes that corresponds to the one or more target outcomes, the one or more reported plausible aspects being aspects that have been successfully emulated by one or more third parties as depicted in FIG. 7k. For instance, the reported plausible aspect identification module 216* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported plausible aspects (e.g., walking 1 mile per day) that are associated with the one or more reported outcomes (e.g., reduce blood pressure) that corresponds to the one or more target outcomes, the one or more reported plausible aspects (e.g., walking 1 mile per day) being aspects that have been successfully emulated by one or more third parties 6*.

In turn, operation 783 may further include an operation 784 for identifying the one or more reported aspects that are relevant to achieving the one or more target outcomes including identifying one or more reported plausible aspects that are associated with the one or more reported outcomes that corresponds to the one or more target outcomes, the one or more reported plausible aspects being aspects that have been successfully emulated by the one or more third parties in order to achieve at least one of the one or more target outcomes as depicted in FIG. 7k. For instance, the reported plausible aspect identification module 216* of the server 10 of FIG. 1b, the local source user device 20' of FIG. 2b, or the local end user device 30" of FIG. 3b identifying the one or more reported aspects 14* that are relevant to achieving the one or more target outcomes including identifying one or more reported plausible aspects that are associated with the one or more reported outcomes and that corresponds to the one or more target outcomes, the one or more reported plausible aspects (e.g., reduced daily meat consumption) being aspects that have been successfully emulated by one or more third parties (e.g., third parties 6* such as other end users who may or may not have same traits as the end user 4*) in order to achieve at least one of the one or more target outcomes (e.g., lower cholesterol level).

In various implementations, the seeking operation 504 of FIG. 5 may include one or more operations for identifying one or more reported intermediate outcomes. For example, in some implementations, operation 759 may include an operation 785 for identifying one or more reported intermediate outcomes that are associated with the one or more reported outcomes as depicted in FIG. 7k. For instance, the reported outcome identification module 210* of the server 10 of FIG. 1b, the local source user device 20' of FIG. 2b, or the local end user device 30" of FIG. 3b identifying one or more reported intermediate outcomes (e.g., a weight loss of 5 pounds, 8 pounds, 15 pounds, and so forth) that are associated with the one or more reported outcomes (e.g., a target outcome such as a total weight loss of 30 pounds).

In turn, operation 785 may further include, in some implementations, an operation 786 for identifying the one or more reported intermediate outcomes that are associated with the one or more reported outcomes including identifying one or more reported intermediate outcomes that occurred prior to one or more occurrences of the one or more reported outcomes as depicted in FIG. 7k. For instance, the reported outcome identification module 210* of the server 10 of FIG. 1b, the local source user device 20' of FIG. 2b, or the local end user device 30" of FIG. 3b identifying the one or more reported intermediate outcomes that are associated with the one or more reported outcomes including identifying one or more reported intermediate outcomes (e.g., increased reading skills score by 10 points) that occurred prior to one or more occurrences of the one or more reported outcomes (e.g., target outcome such as increased reading skills score by 50 points).

In some implementations, operation 785 may include an operation 787 for identifying the one or more reported intermediate outcomes that are associated with the one or more reported outcomes including identifying one or more reported intermediate outcomes that are associated with one or more source users that the one or more reported aspects are associated with as depicted in FIG. 7k. For instance, the reported outcome identification module 210* of the server 10 of FIG. 1b, the local source user device 20' of FIG. 2b, or the local end user device 30" of FIG. 3b identifying the one or more reported intermediate outcomes that are associated with the one or more reported outcomes (e.g., lower blood pressure level by 30 mmHg) including identifying one or more reported intermediate outcomes (e.g., lower blood pressure level by 10 mmHg) that are associated with one or more source users 2* that the one or more reported aspects 14* (e.g., sleep 8 hours per day) are associated with.

Various types of reported aspects 14* may be sought through the seeking operation 504 of FIG. 5 in various alternative implementations. For example, in some implementations, the seeking operation 504 of FIG. 5 may include an operation 788 for seeking the one or more reported aspects that are relevant to achieving the one or more target outcomes including seeking one or more reported aspects relating to one or more incidences of source user behavior associated with one or more source users as depicted in FIG. 7l. For instance, the reported aspect seeking module 104* of the server 10 of FIG. 1b, the local source user device 20' of FIG. 2b, or the local end user device 30" of FIG. 3b seeking the one or more reported aspects 14* that are relevant to achieving the one or more target outcomes including seeking one or more reported aspects 14* relating to one or more incidences of source user behavior (e.g., dietary behavior, physical activity behavior, behavior towards others, mental or physical acts, and so forth) associated with one or more source users 2*.

In various implementations, operation 788 may include one or more additional operations. For example, in some implementations, operation 788 may further include an operation 789 for seeking the one or more reported aspects that are relevant to achieving the one or more target outcomes including seeking one or more reported aspects relating to one or more incidences of physical acts executed by one or more source users as depicted in FIG. 7l. For instance, the reported aspect seeking module 104* of the server 10 of FIG. 1b, the local source user device 20' of FIG. 2b, or the local end user device 30" of FIG. 3b seeking the one or more reported aspects 14* that are relevant to achieving the one or more target outcomes including seeking one or more reported aspects 14* relating to one or more incidences of physical acts (e.g., consume a food item or a medicine, attend class, read, exercise, and so forth) executed by one or more source users 2*.

In the same or different implementations, operation 788 may include an operation 790 for seeking the one or more reported aspects that are relevant to achieving the one or more target outcomes including seeking one or more reported aspects relating to one or more incidences of user attitudes associated with one or more source users as depicted in FIG. 7l. For instance, the reported aspect seeking module 104* of the server 10 of FIG. 1b, the local source user device 20' of FIG. 2b, or the local end user device 30" of FIG. 3b seeking the one or more reported aspects 14* that are relevant to achieving the one or more target outcomes including seeking one or more reported aspects 14* relating to one or more incidences of user attitudes (e.g., being indifferent, feeling critical, feeling skeptical, feeling optimistic, and so forth) associated with one or more source users 2*.

In the same or different implementations, operation 788 may include an operation 791 for seeking the one or more reported aspects that are relevant to achieving the one or more target outcomes including seeking one or more reported aspects relating to one or more incidences of user conduct associated with one or more source users as depicted in FIG. 7l. For instance, the reported aspect seeking module 104* of the server 10 of FIG. 1b, the local source user device 20' of FIG. 2b, or the local end user device 30" of FIG. 3b seeking the one or more reported aspects 14* that are relevant to achieving the one or more target outcomes including seeking one or more reported aspects 14* relating to one or more incidences of user conduct (e.g., behavior towards others, treatment of others, manner in which acts are executed, and so forth) associated with one or more source users 2.

Figure 7M:
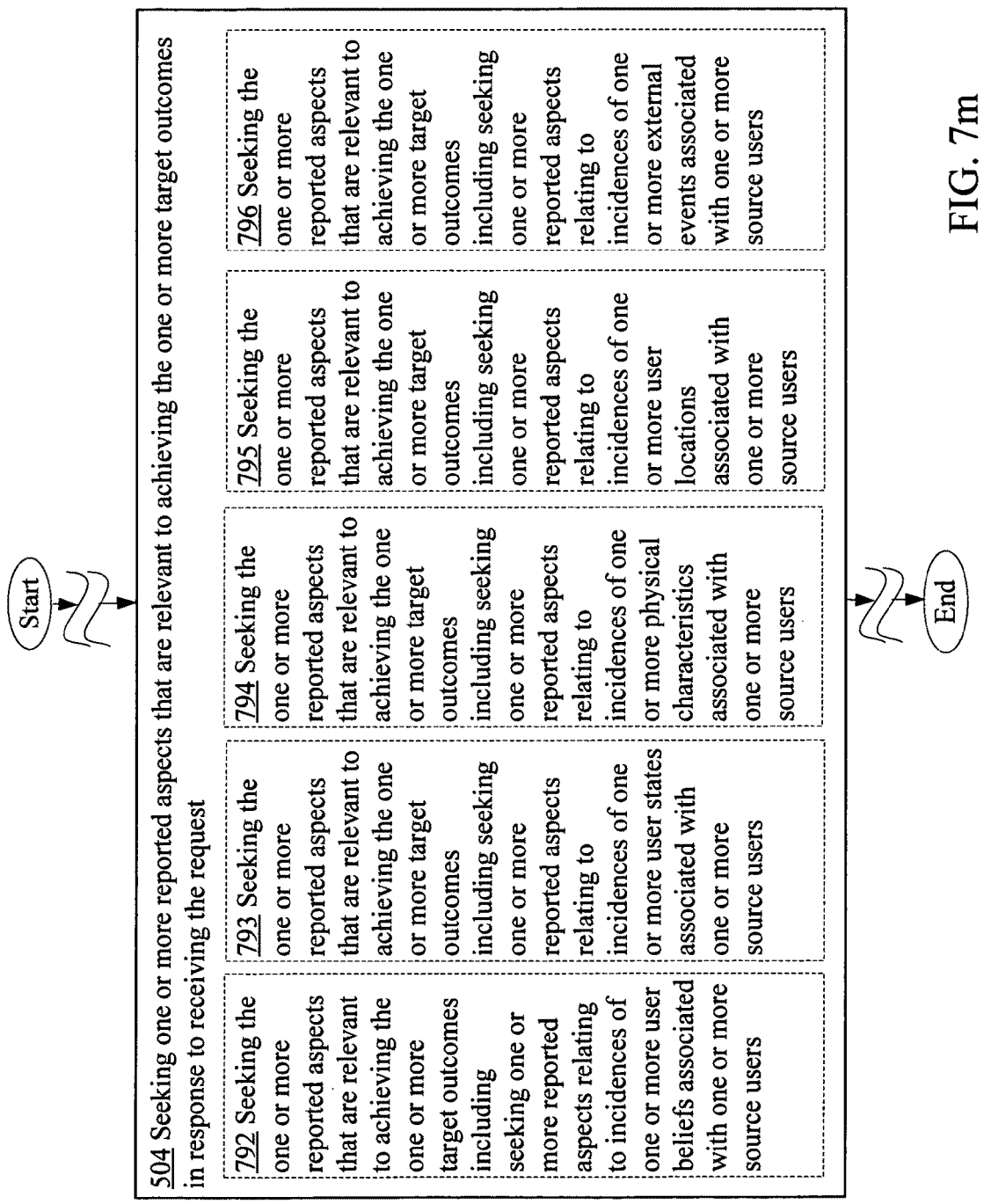
FIG. 7m is a high-level logic flowchart of a process depicting alternate implementations of the seeking operation 504 of FIG. 5.

In some implementations, the seeking operation 504 of FIG. 5 may include an operation 792 for seeking the one or more reported aspects that are relevant to achieving the one or more target outcomes including seeking one or more reported aspects relating to incidences of one or more user beliefs associated with one or more source users as depicted in FIG. 7m. For instance, the reported aspect seeking module 104* of the server 10 of FIG. 1b, the local source user device 20' of FIG. 2b, or the local end user device 30" of FIG. 3b seeking the one or more reported aspects 14* that are relevant to achieving the one or more target outcomes including seeking one or more reported aspects 14* relating to incidences of one or more user beliefs (e.g., religious beliefs, spiritual beliefs, prejudicial beliefs, and so forth) associated with one or more source users 2*.

In some implementations, the seeking operation 504 of FIG. 5 may include an operation 793 for seeking the one or more reported aspects that are relevant to achieving the one or more target outcomes including seeking one or more reported aspects relating to incidences of one or more user states associated with one or more source users as depicted in FIG. 7m. For instance, the reported aspect seeking module 104* of the server 10 of FIG. 1b, the local source user device 20' of FIG. 2b, or the local end user device 30" of FIG. 3b seeking the one or more reported aspects 14* that are relevant to achieving the one or more target outcomes including seeking one or more reported aspects 14* relating to incidences of one or more user states (e.g., mental states, marital states, employment state, physical state, availability state, and so forth) associated with one or more source users 2*.

In some implementations, the seeking operation 504 of FIG. 5 may include an operation 794 for seeking the one or more reported aspects that are relevant to achieving the one or more target outcomes including seeking one or more reported aspects relating to incidences of one or more physical characteristics associated with one or more source users as depicted in FIG. 7m. For instance, the reported aspect seeking module 104* of the server 10 of FIG. 1b, the local source user device 20' of FIG. 2b, or the local end user device 30" of FIG. 3b seeking the one or more reported aspects 14* that are relevant to achieving the one or more target outcomes including seeking one or more reported aspects 14* relating to incidences of one or more physical characteristics (e.g., hair or eye color, hair length, hair style, facial hair characteristics, overall body figure, body weight, and so forth) associated with one or more source users 2*.

In some implementations, the seeking operation 504 of FIG. 5 may include an operation 795 for seeking the one or more reported aspects that are relevant to achieving the one or more target outcomes including seeking one or more reported aspects relating to incidences of one or more user locations associated with one or more source users as depicted in FIG. 7m. For instance, the reported aspect seeking module 104* of the server 10 of FIG. 1b, the local source user device 20' of FIG. 2b, or the local end user device 30" of FIG. 3b seeking the one or more reported aspects 14* that are relevant to achieving the one or more target outcomes including seeking one or more reported aspects 14* relating to incidences of one or more user locations (e.g., home, workplace, New York City, beach, and so forth) associated with one or more source users 2*.

In some implementations, the seeking operation 504 of FIG. 5 may include an operation 796 for seeking the one or more reported aspects that are relevant to achieving the one or more target outcomes including seeking one or more reported aspects relating to incidences of one or more external events associated with one or more source users as depicted in FIG. 7m. For instance, the reported aspect seeking module 104* of the server 10 of FIG. 1b, the local source user device 20' of FIG. 2b, or the local end user device 30" of FIG. 3b seeking the one or more reported aspects 14* that are relevant to achieving the one or more target outcomes including seeking one or more reported aspects 14* relating to incidences of one or more external events (e.g., hot or cold weather, heavy or no auto traffic, and so forth) associated with one or more source users 2*.

Figure 8A:
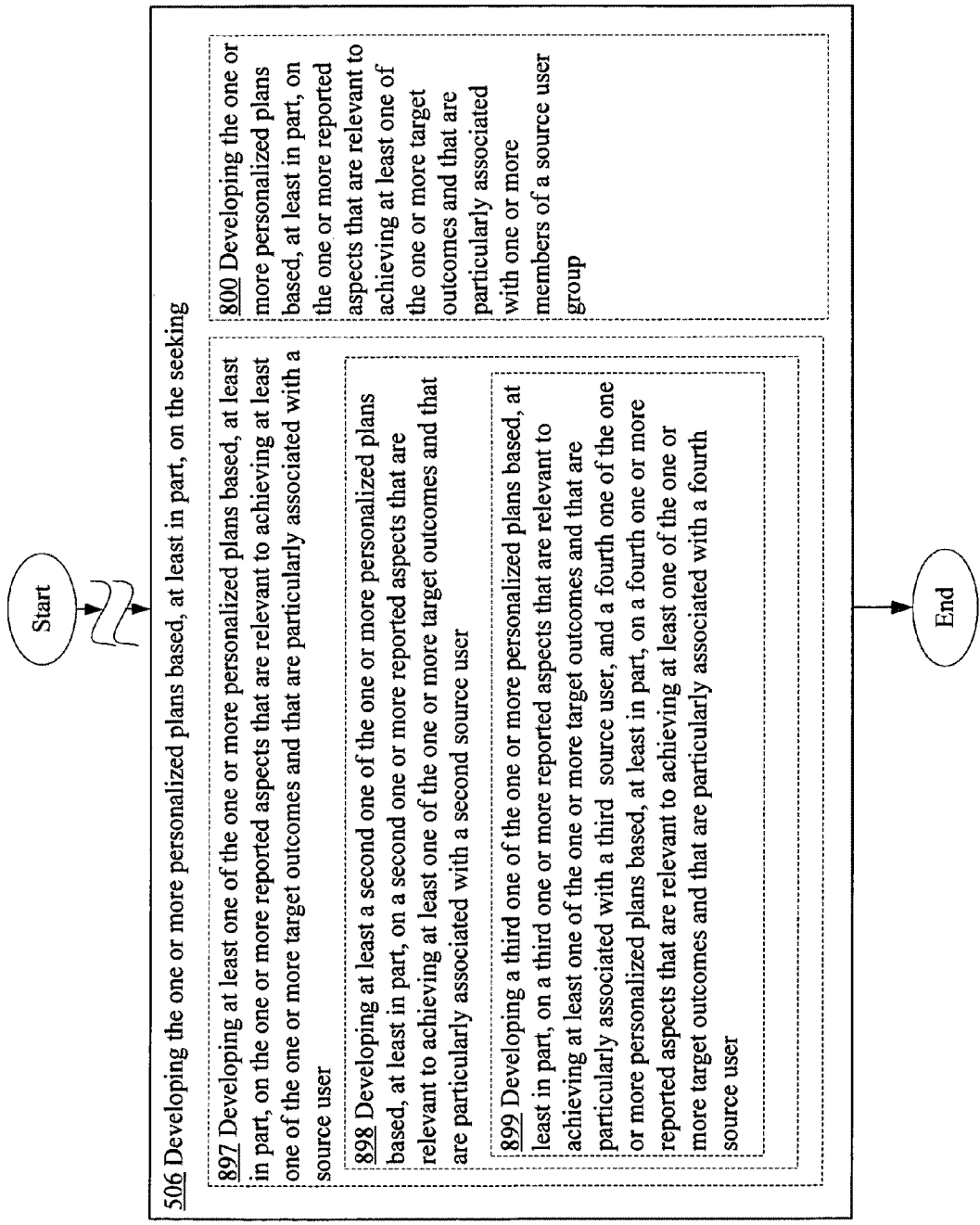
FIG. 8a is a high-level logic flowchart of a process depicting alternate implementations of the development operation 506 of FIG. 5.

The development operation 506 of FIG. 5 may be executed in a variety of different ways in various alternative implementations. For example, in various implementations, the development operation 506 may include an operation 897 for developing at least one of the one or more personalized plans based, at least in part, on the one or more reported aspects that are relevant to achieving at least one of the one or more target outcomes and that are particularly associated with a source user as depicted in FIG. 8*a*. For instance, the personalized plan development module 106* of the server 10 of FIG. 1*b*, the local source user device 20' of FIG. 2*b*, or the local end user device 30" of FIG. 3*b* developing at least one of the one or more personalized plans 16* based, at least in part, on the one or more reported aspects 14 that are relevant to achieving at least one of the one or more target outcomes and that are particularly associated with a source user 2*a**. Thus, in these implementations, the execution of operation 897 may result in the development of at least one personalized plan 16* based on one or more reported aspects 14* that are related to a particular source user (e.g., source user 2*a**).

Other personalized plans 16* may also be developed based on reported aspects associated with other source users (e.g., source user 2*b**) in various alternative implementations. For example, in some implementations, operation 897 may include an operation 898 for developing at least a second one of the one or more personalized plans based, at least in part, on a second one or more reported aspects that are relevant to achieving at least one of the one or more target outcomes and that are particularly associated with a second source user as depicted in FIG. 8*a*. For instance, the personalized plan development module 106* of the server 10 of FIG. 1*b*, the local source user device 20' of FIG. 2*b*, or the local end user device 30" of FIG. 3*b* developing at least a second one of the one or more personalized plans 16* based, at least in part, on a second one or more reported aspects that are relevant to achieving at least one of the one or more target outcomes and that are particularly associated with a second source user 2*b**. Thus, the execution of operation 898 may result in the development of a second personalized plan 16* based on a second one or more reported aspects that are related to a second source user (e.g., source user 2*b**).

Operation 898 may in turn further include, in various implementations, an operation 899 for developing a third one of the one or more personalized plans based, at least in part, on a third one or more reported aspects that are relevant to achieving at least one of the one or more target outcomes and that are particularly associated with a third source user, and a fourth one of the one or more personalized plans based, at least in part, on a fourth one or more reported aspects that are relevant to achieving at least one of the one or more target outcomes and that are particularly associated with a fourth source user as depicted in FIG. 8*a*. For instance, the personalized plan development module 106* of the server 10 of FIG. 1*b*, the local source user device 20' of FIG. 2*b*, or the local end user device 30" of FIG. 3*b* developing a third one of the one or more personalized plans 16* based, at least in part, on a third one or more reported aspects that are relevant to achieving at least one of the one or more target outcomes and that are particularly associated with a third source user (e.g., source user 2*c**), and a fourth one of the one or more personalized plans 16* based, at least in part, on a fourth one or more reported aspects that are relevant to achieving at least one of the one or more target outcomes and that are particularly associated with a fourth source user (e.g., source user 2*d**).

In various implementations, the development operation 506 may include an operation 800 for developing the one or more personalized plans based, at least in part, on the one or more reported aspects that are relevant to achieving at least one of the one or more target outcomes and that are particularly associated with one or more members of a source user group as depicted in FIG. 8*a*. For instance, the personalized plan development module 106* of the server 10 of FIG. 1*b*, the local source user device 20' of FIG. 2*b*, or the local end user device 30" of FIG. 3*b* developing the one or more personalized plans 16* based, at least in part, on the one or more reported aspects 14* that are relevant to achieving at least one of the one or more target outcomes (e.g., one or more reported outcomes that corresponds to the one or more target outcomes) and that are particularly associated with one or more members of a source user group (e.g., a social group such as a social networking group, a medical patient group, an employee group, a religious group, and so forth).

Figure 8B:
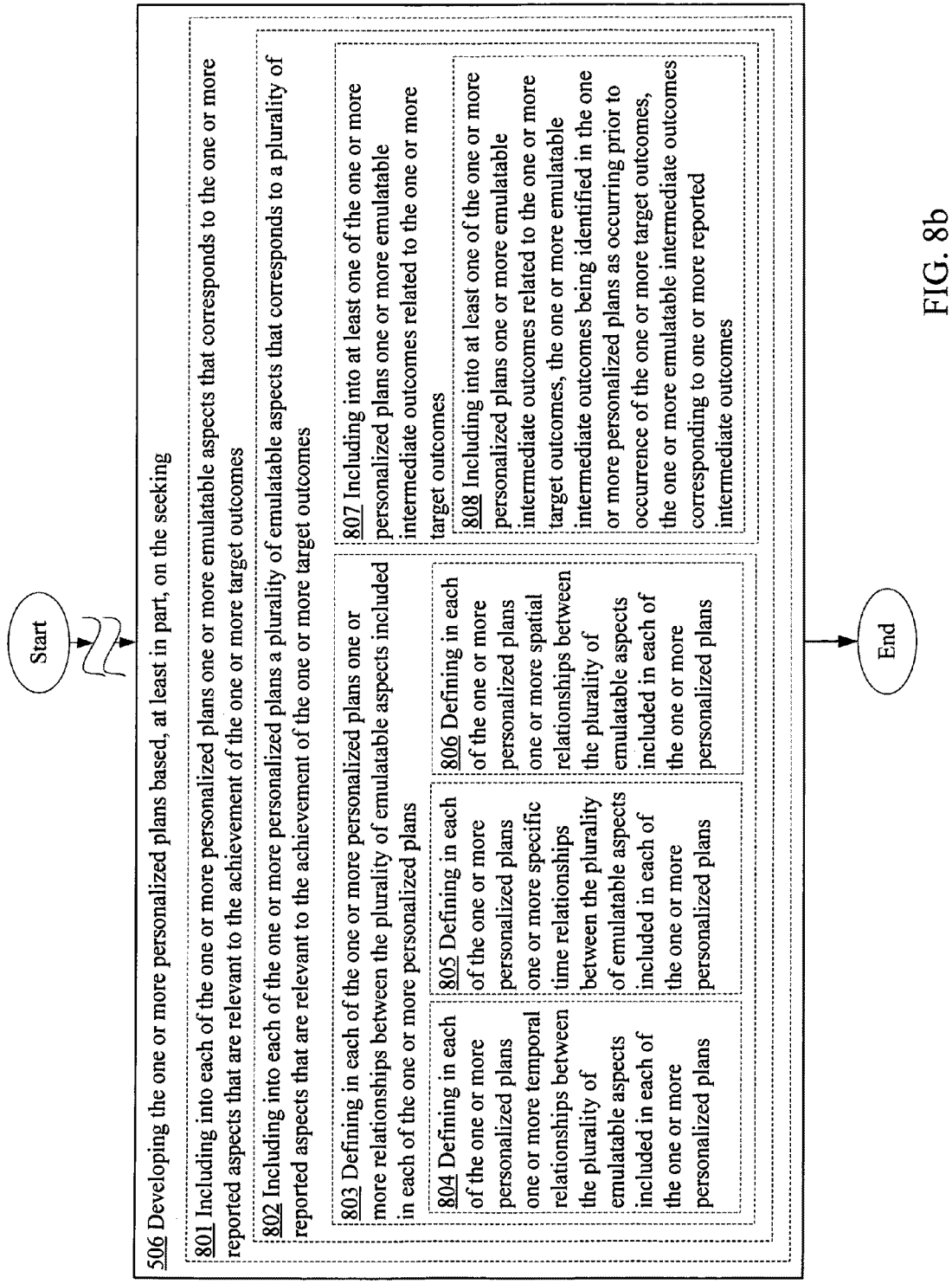
FIG. 8b is a high-level logic flowchart of a process depicting alternate implementations of the development operation 506 of FIG. 5.

The one or more personalized plans 16* developed through the development operation 506 of FIG. 5 may be developed, at least in part, by including into the one or more personalized plans 16* emulatable aspects. For example, in various implementations, the development operation 506 may include an operation 801 for including into each of the one or more personalized plans one or more emulatable aspects that corresponds to the one or more reported aspects that are relevant to the achievement of the one or more target outcomes as depicted in FIG. 8*b*. For instance, the emulatable aspect inclusion module 218* of the server 10 of FIG. 1*b*, the local source user device 20' of FIG. 2*b*, or the local end user device 30" of FIG. 3*b* including into each of the one or more personalized plans 16* one or more emulatable aspects (e.g., indications of one or more aspects that may be emulated) that corresponds to the one or more reported aspects that are relevant to the achievement of the one or more target outcomes associated with the one or more personalized plans 16*. Note that in some situations a personalized plan 16* may include only a single emulatable aspect such as "being a vegan."

In other cases, however, multiple emulatable aspects may be included in a personalized plan 16* to be developed. For example, in some implementations, operation 801 may include an operation 802 for including into each of the one or more personalized plans a plurality of emulatable aspects that corresponds to a plurality of reported aspects that are relevant to the achievement of the one or more target outcomes as depicted in FIG. 8*b*. For instance, the emulatable aspect inclusion module 218* of the server 10 of FIG. 1*b*, the local source user device 20' of FIG. 2*b*, or the local end user device 30" of FIG. 3*b* including into each of the one or more personalized plans 16* a plurality of emulatable aspects (e.g., eat only fruits on day one, eat only vegetables on day two, and so forth) that corresponds to a plurality of reported aspects 14* that are relevant to the achievement of the one or more target outcomes (e.g., lose 20 pounds in a month).

When multiple emulatable aspects are to be included in a personalized plan 16* other types of information may also be included in the personalized plan 16* to be developed. For example, in some implementations, operation 802 may include an operation 803 for defining in each of the one or more personalized plans one or more relationships between the plurality of emulatable aspects included in each of the one or more personalized plans as depicted in FIG. 8*b*. For instance, the relationship defining module 220* of the server 10 of FIG. 1*b*, the local source user device 20' of FIG. 2*b*, or the local end user device 30" of FIG. 3*b* defining (e.g., indicating) in each of the one or more personalized plans 16* one or more relationships between the plurality of emulatable aspects included in each of the one or more personalized plans 16*. Various types of relationships may be defined in various alternative implementations.

For example, in some implementations, operation 803 may include an operation 804 for defining in each of the one or more personalized plans one or more temporal relationships between the plurality of emulatable aspects included in each of the one or more personalized plans as depicted in FIG. 8*b*. For instance, the relationship defining module 220* of the server 10 of FIG. 1b, the local source user device 20' of FIG. 2b, or the local end user device 30" of FIG. 3b defining in each of the one or more personalized plans 16* one or more temporal relationships between the plurality of emulatable aspects included in each of the one or more personalized plans 16*. For example, in the above example indicating that only fruits should be eaten on the day before the day that only vegetables are consumed.

In some implementations, operation 803 may include an operation 805 for defining in each of the one or more personalized plans one or more specific time relationships between the plurality of emulatable aspects included in each of the one or more personalized plans as depicted in FIG. 8b. For instance, the relationship defining module 220* of the server 10 of FIG. 1b, the local source user device 20' of FIG. 2b, or the local end user device 30" of FIG. 3b defining in each of the one or more personalized plans 16* one or more specific time relationships between the plurality of emulatable aspects included in each of the one or more personalized plans 16*. As a illustration, suppose a personalized plan 16* to be developed is for reducing migraine headaches (e.g., target outcome), and the personalized plan 16* indicates that the end user 4* should consume three specific types of vegetables (e.g., veg1, veg2, and veg3) a day. The personalized plan 16* may then be developed to indicate at what times should veg1 be consumed, what time should veg2 be consumed with respect to the time that veg1 was consumed, and what time should veg3 be consumed with respect to the times that veg1 and veg2 were consumed.

In some implementations, operation 803 may include an operation 806 for defining in each of the one or more personalized plans one or more spatial relationships between the plurality of emulatable aspects included in each of the one or more personalized plans as depicted in FIG. 8b. For instance, the relationship defining module 220* of the server 10 of FIG. 1b, the local source user device 20' of FIG. 2b, or the local end user device 30" of FIG. 3b defining in each of the one or more personalized plans 16 one or more spatial relationships between the plurality of emulatable aspects included in each of the one or more personalized plans 16*. As an illustration, suppose a personalized plan 16* to be developed is for reducing stress, and that the personalized plan 16* indicates that the end user 4* in order to reduce stress should break his daily work routine into two portions, a first work portion and a second work portion. The personalized plan 16* may be developed by indicating that the first work portion should be done at the end user's work place, while the second portion should be done at home.

Other types of information may also be included into a personalized plan 16* when, for example, multiple emulatable aspects are included into a personalized plan 16*. For example, in various implementations, operation 802 may include an operation 807 for including into at least one of the one or more personalized plans one or more emulatable intermediate outcomes related to the one or more target outcomes as depicted in FIG. 8b. For instance, the emulatable intermediate outcome inclusion module 222* of the server 10 of FIG. 1b, the local source user device 20' of FIG. 2b, or the local end user device 30" of FIG. 3b including into at least one of the one or more personalized plans 16* one or more emulatable intermediate outcomes related to the one or more target outcomes. As an illustration, suppose a personalized plan 16* is to be developed for losing a body weight of 20 pounds (e.g., target outcome). The personalized plan 16* may be developed to include intermediate outcomes (e.g., 5 pound weight loss after two weeks, 8 pound of weight loss after four weeks, and so forth) to facilitate in determining whether the end user 4* in following the personalized plan 16* is on track to achieve the target outcome (e.g., 20 pound weight loss).

In some implementations, operation 807 may include an operation 808 for including into at least one of the one or more personalized plans one or more emulatable intermediate outcomes related to the one or more target outcomes, the one or more emulatable intermediate outcomes being identified in the one or more personalized plans as occurring prior to occurrence of the one or more target outcomes, the one or more emulatable intermediate outcomes corresponding to one or more reported intermediate outcomes as depicted in FIG. 8b. For instance, the emulatable intermediate outcome inclusion module 222* of the server 10 of FIG. 1b, the local source user device 20' of FIG. 2b, or the local end user device 30" of FIG. 3b including into at least one of the one or more personalized plans 16* one or more emulatable intermediate outcomes related to the one or more target outcomes, the one or more emulatable intermediate outcomes being identified in the one or more personalized plans 16* as occurring prior to occurrence of the one or more target outcomes (e.g., final reported outcomes), the one or more emulatable intermediate outcomes corresponding to one or more reported intermediate outcomes.

Figure 8C:
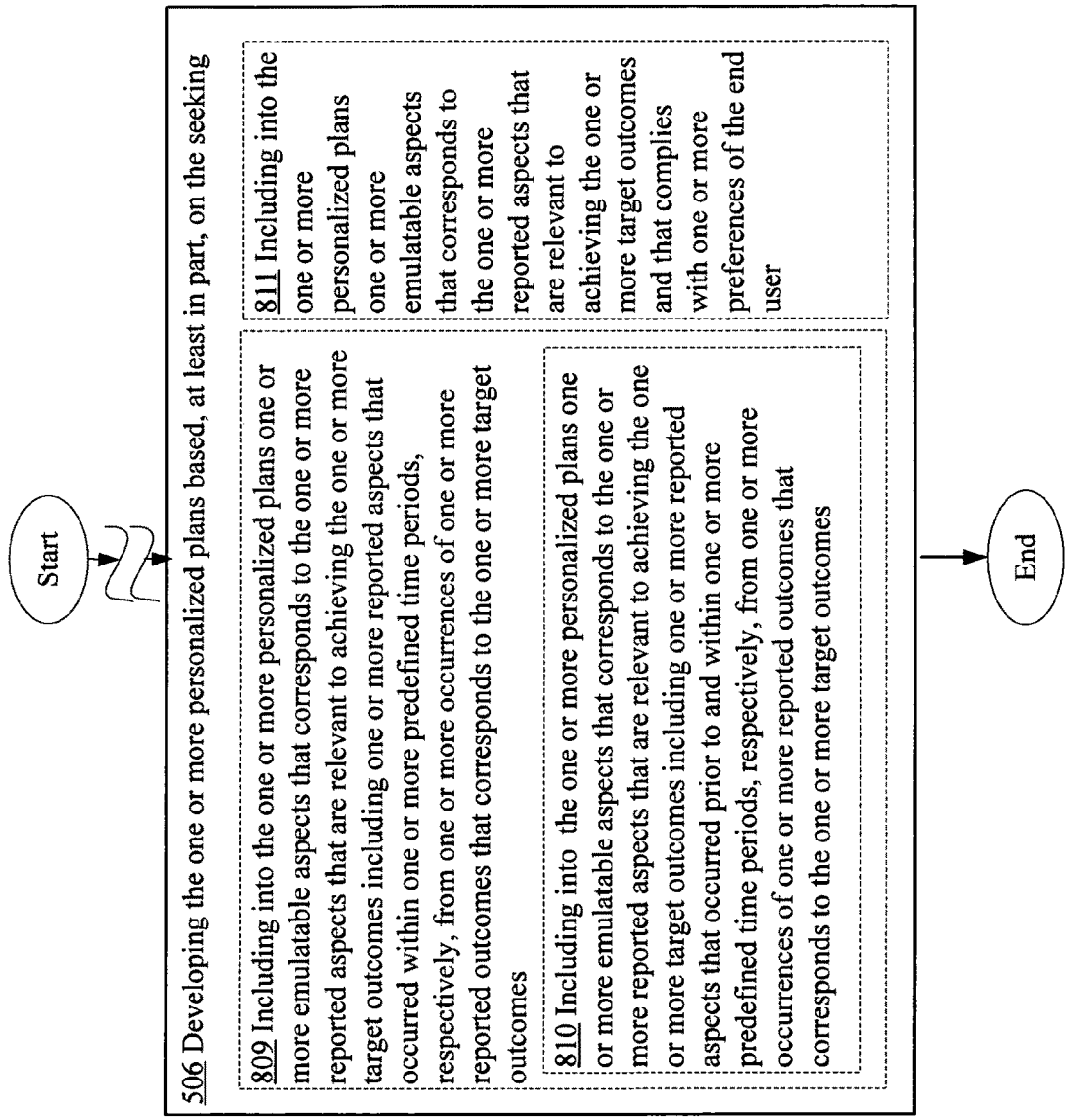
FIG. 8c is a high-level logic flowchart of a process depicting alternate implementations of the development operation 506 of FIG. 5.

The one or more emulatable aspects that may be included into a personalized plan 16* developed through the development operation 506 of FIG. 5 may correspond to one or more reported aspects 14* that have been determined to be relevant to the achievement of one or more reported outcomes, which may further correspond to the one or more target outcomes. For example, in some implementations, the development operation 506 may include an operation 809 for including into the one or more personalized plans one or more emulatable aspects that corresponds to the one or more reported aspects that are relevant to achieving the one or more target outcomes including one or more reported aspects that occurred within one or more predefined time periods, respectively, from one or more occurrences of one or more reported outcomes that corresponds to the one or more target outcomes as depicted in FIG. 8c. For instance, the emulatable aspect inclusion module 218* of the server 10 of FIG. 1b, the local source user device 20' of FIG. 2b, or the local end user device 30" of FIG. 3b including into the one or more personalized plans 16* one or more emulatable aspects that corresponds to the one or more reported aspects 14* that are relevant to achieving the one or more target outcomes including one or more reported aspects 14* that occurred within one or more predefined time periods (e.g., one day, 48 hours, one month, one year, or other time periods), respectively, from one or more occurrences of one or more reported outcomes that corresponds to the one or more target outcomes.

As a further illustration, suppose a first personalized plan 16* is to be developed that may be based on initially seeking or identifying at least a first reported outcome that corresponds to at least a first target outcome. A first one or more reported aspects may then be identified that occurred within a predefined time period from the occurrence of the first reported outcome. By doing so, reported aspects that occurred well before or well after (e.g., outside the predefined time period) the occurrence of the first reported outcome (e.g. target outcome) may be ignored since they are not likely to be relevant to the occurrence of the first reported outcome. Note that in this example, the first one or more reported aspects and the first reported outcome that are identified may all be associated with a first source user (e.g., source user 2a*). Similarly, a second personalized plan 16*** may be developed by identifying a second one or more reported aspects that occurred within a predefined time period from occurrence of a second reported outcome that corresponds to the first target outcome or a second target outcome. In some cases, the second one or more reported aspects and the second reported outcome may all be associated with a second source user (e.g., source user 2b*). In this illustration, the predefined time period described above may depend upon the type of personalized plan 16* being developed or may be set by a source user (e.g., a source user 2a*), an end user 4*, or by a third party 6*.

In some implementations, the 809 may further include an operation 810 for including into the one or more personalized plans one or more emulatable aspects that corresponds to the one or more reported aspects that are relevant to achieving the one or more target outcomes including one or more reported aspects that occurred prior to and within one or more predefined time periods, respectively, from one or more occurrences of one or more reported outcomes that corresponds to the one or more target outcomes as depicted in FIG. 8c. For instance, the emulatable aspect inclusion module 218* of the server 10 of FIG. 1b, the local source user device 20' of FIG. 2b, or the local end user device 30" of FIG. 3b including into the one or more personalized plans 16* one or more emulatable aspects that corresponds to the one or more reported aspects 14* that are relevant to achieving the one or more target outcomes including one or more reported aspects 14* that occurred prior to and within one or more predefined time periods, respectively, from one or more occurrences of one or more reported outcomes that corresponds to the one or more target outcomes. Note that the difference between operation 809 and operation 810 is the inclusion of the phase "prior to" in operation 810.

In various implementations, one or more emulatable aspects may be included into a personalized plan 16* that complies with one or more preferences and/or one or more limitations. For example, in some implementations, the development operation 506 of FIG. 5 may include an operation 811 for including into the one or more personalized plans one or more emulatable aspects that corresponds to the one or more reported aspects that are relevant to achieving the one or more target outcomes and that complies with one or more preferences of the end user as depicted in FIG. 8c. For instance, the emulatable aspect inclusion module 218* of the server 10 of FIG. 1b, the local source user device 20' of FIG. 2b, or the local end user device 30" of FIG. 3b including into the one or more personalized plans 16* one or more emulatable aspects that corresponds to the one or more reported aspects 14*(e.g., as found through the seeking operation 504 of FIG. 5) that are relevant to achieving the one or more target outcomes and that complies with one or more preferences (e.g., interests) of the end user 4*. For example, the end user 4* may only be interested in reported aspects that relate to dietary activities or sleep activities.

Figure 8D:
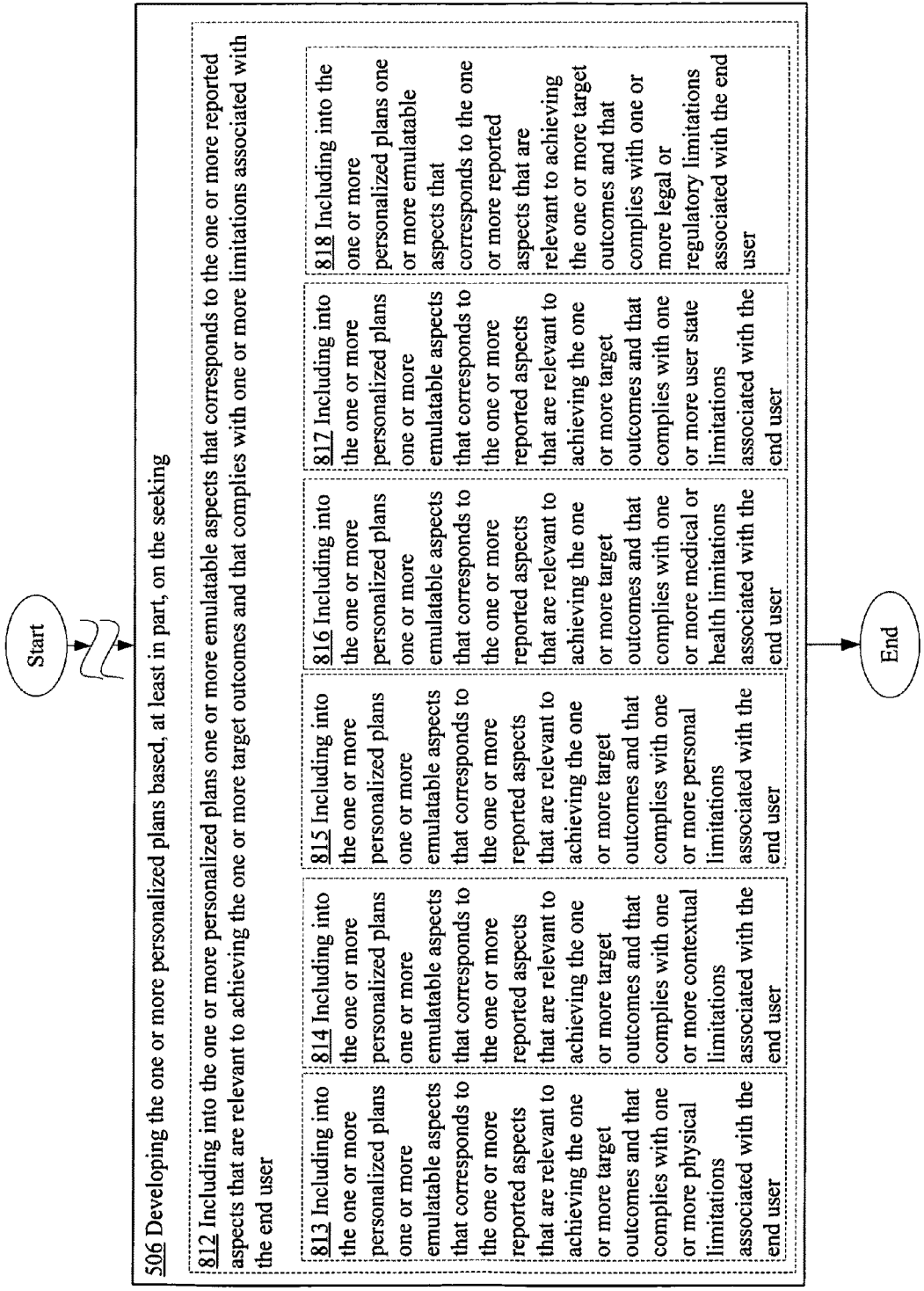
FIG. 8d is a high-level logic flowchart of a process depicting alternate implementations of the development operation 506 of FIG. 5.

In the same or different implementations, the development operation 506 may include an operation 812 for including into the one or more personalized plans one or more emulatable aspects that corresponds to the one or more reported aspects that are relevant to achieving the one or more target outcomes and that complies with one or more limitations associated with the end user as depicted in FIG. 8d. For instance, the emulatable aspect inclusion module 218* of the server 10 of FIG. 1b, the local source user device 20' of FIG. 2b, or the local end user device 30" of FIG. 3b including into the one or more personalized plans 16* one or more emulatable aspects that corresponds to the one or more reported aspects 14* that are relevant to achieving the one or more target outcomes and that complies with (e.g., does not violate) one or more limitations (e.g., personal or physical limitations) associated with the end user 4*. The one or more reported aspects 14* that corresponds to the one or more emulatable aspects that may be included into the one or more personalized plans 16* may comply with a variety of different limitations in various alternative implementations.

For example, in some implementations, operation 812 may include an operation 813 for including into the one or more personalized plans one or more emulatable aspects that corresponds to the one or more reported aspects that are relevant to achieving the one or more target outcomes and that complies with one or more physical limitations associated with the end user as depicted in FIG. 8d. For instance, the emulatable aspect inclusion module 218* of the server 10 of FIG. 1b, the local source user device 20' of FIG. 2b, or the local end user device 30" of FIG. 3b including into the one or more personalized plans 16* one or more emulatable aspects that corresponds to the one or more reported aspects 14* that are relevant to achieving the one or more target outcomes and that complies with one or more physical limitations (e.g., missing limb, paralysis, visual or hearing impediment, and so forth) associated with the end user 4*.

In the same or different implementations, operation 812 may include an operation 814 for including into the one or more personalized plans one or more emulatable aspects that corresponds to the one or more reported aspects that are relevant to achieving the one or more target outcomes and that complies with one or more contextual limitations associated with the end user as depicted in FIG. 8d. For instance, the emulatable aspect inclusion module 218* of the server 10 of FIG. 1b, the local source user device 20' of FIG. 2b, or the local end user device 30" of FIG. 3b including into the one or more personalized plans one or more emulatable aspects that corresponds to the one or more reported aspects 14* that are relevant to achieving the one or more target outcomes and that complies with one or more contextual limitations (e.g., logistical limitations such as scheduling limitations, geographical limitations, asset limitations, and so forth) associated with the end user 4*.

In the same or different implementations, operation 812 may include an operation 815 for including into the one or more personalized plans one or more emulatable aspects that corresponds to the one or more reported aspects that are relevant to achieving the one or more target outcomes and that complies with one or more personal limitations associated with the end user as depicted in FIG. 8d. For instance, the emulatable aspect inclusion module 218* of the server 10 of FIG. 1b, the local source user device 20' of FIG. 2b, or the local end user device 30" of FIG. 3b including into the one or more personalized plans 16* one or more emulatable aspects that corresponds to the one or more reported aspects 14* that are relevant to achieving the one or more target outcomes and that complies with one or more personal limitations (e.g., religious beliefs, dietary beliefs, phobias, personal prejudices, limitations related to personal experiences, personal work schedule obligations, family dynamics or circumstances, and so forth) associated with the end user 4*.

In the same or different implementations, operation 812 may include an operation 816 for including into the one or more personalized plans one or more emulatable aspects that corresponds to the one or more reported aspects that are relevant to achieving the one or more target outcomes and that complies with one or more medical or health limitations associated with the end user as depicted in FIG. 8d. For instance, the emulatable aspect inclusion module 218* of the server 10 of FIG. 1b, the local source user device 20' of FIG. 2b, or the local end user device 30" of FIG. 3b including into the one or more personalized plans 16* one or more emulatable aspects that corresponds to the one or more reported aspects 14* that are relevant to achieving the one or more target outcomes and that complies with one or more medical or health limitations (e.g., medical limitations such as limitations resulting from an illness or treatment of an illness including physical limitations due to cancer or treatment of cancer, health limitations related to the physical conditioning of the end user 4*, genetic limitations, and so forth) associated with the end user 4*.

In the same or different implementations, operation 812 may include an operation 817 for including into the one or more personalized plans one or more emulatable aspects that corresponds to the one or more reported aspects that are relevant to achieving the one or more target outcomes and that complies with one or more user state limitations associated with the end user as depicted in FIG. 8*d*. For instance, the emulatable aspect inclusion module 218* of the server 10 of FIG. 1*b*, the local source user device 20' of FIG. 2*b*, or the local end user device 30" of FIG. 3*b* including into the one or more personalized plans 16* one or more emulatable aspects that corresponds to the one or more reported aspects 14* that are relevant to achieving the one or more target outcomes and that complies with one or more user state limitations (e.g., end user 4* is married, end user 4* is in mourning, end user 4* is unemployed, end user 4* is a vegan, and so forth) associated with the end user 4*.

In the same or different implementations, operation 812 may include an operation 818 for including into the one or more personalized plans one or more emulatable aspects that corresponds to the one or more reported aspects that are relevant to achieving the one or more target outcomes and that complies with one or more legal or regulatory limitations associated with the end user as depicted in FIG. 8*d*. For instance, the emulatable aspect inclusion module 218* of the server 10 of FIG. 1*b*, the local source user device 20' of FIG. 2*b*, or the local end user device 30" of FIG. 3*b* including into the one or more personalized plans 16* one or more emulatable aspects that corresponds to the one or more reported aspects 14* that are relevant to achieving the one or more target outcomes and that complies with one or more legal or regulatory limitations (e.g., drug regulations, laws related to conduct or behavior in the jurisdiction of the end user 4*, and so forth) associated with the end user 4*.

Figure 8E:
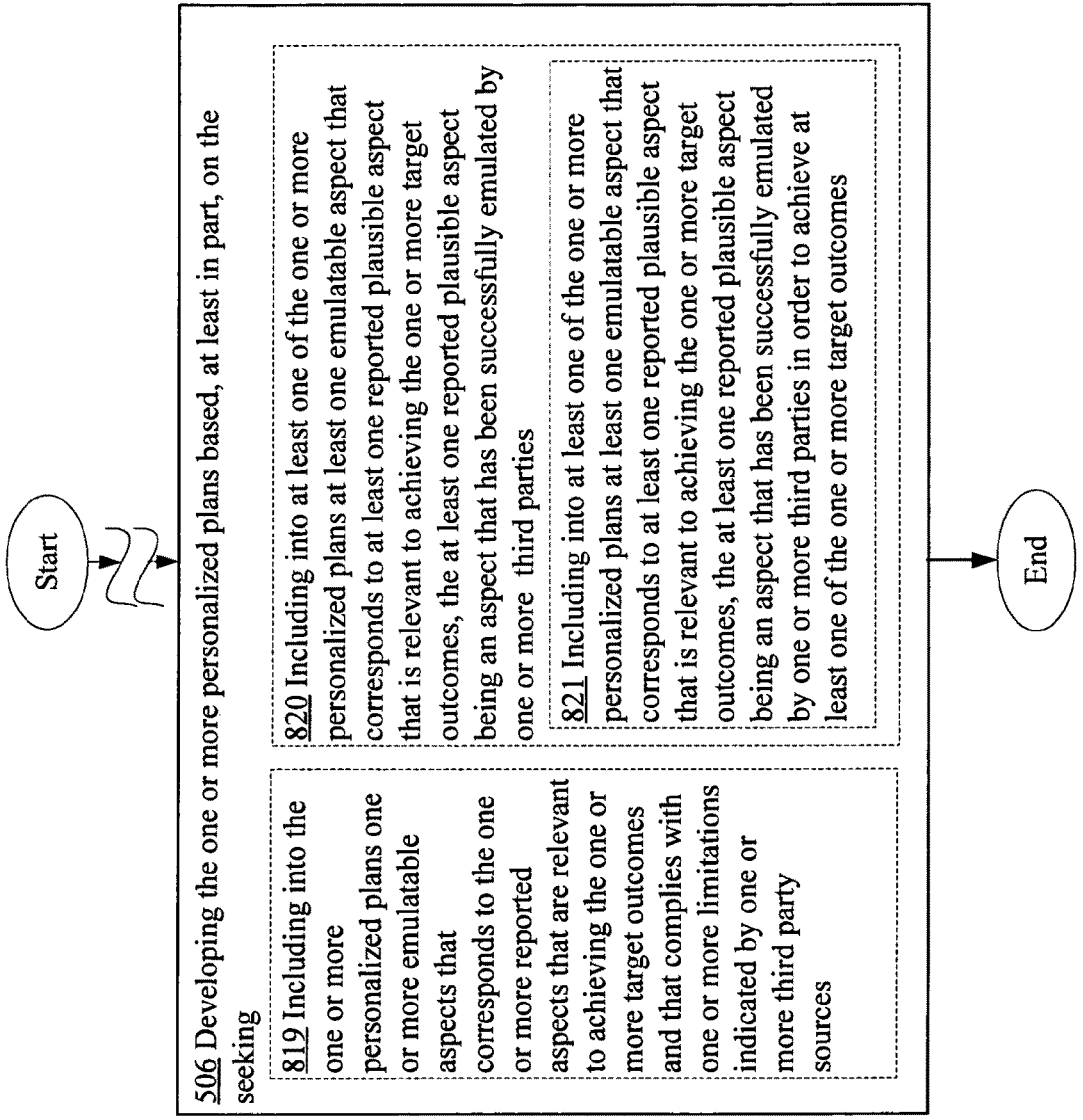
FIG. 8e is a high-level logic flowchart of a process depicting alternate implementations of the development operation 506 of FIG. 5.

In some implementations, the development operation 506 of FIG. 5 may include an operation 819 for including into the one or more personalized plans one or more emulatable aspects that corresponds to the one or more reported aspects that are relevant to achieving the one or more target outcomes and that complies with one or more limitations indicated by one or more third party sources as depicted in FIG. 8*e*. For instance, the emulatable aspect inclusion module 218* of the server 10 of FIG. 1*b*, the local source user device 20' of FIG. 2*b*, or the local end user device 30" of FIG. 3*b* including into the one or more personalized plans 16* one or more emulatable aspects that corresponds to the one or more reported aspects 14* that are relevant to achieving the one or more target outcomes and that complies with one or more limitations indicated by one or more third party sources (e.g., publications, research results, medical advisories, and so forth).

In various implementations, the one or more emulatable aspects that may be included into a personalized plan 16* may be based on one or more reported plausible aspects that have been successfully emulated by one or more third parties 6*. For example, in some implementations, the development operation 506 of FIG. 5 may include an operation 820 for including into at least one of the one or more personalized plans at least one emulatable aspect that corresponds to at least one reported plausible aspect that is relevant to achieving the one or more target outcomes, the at least one reported plausible aspect being an aspect that has been successfully emulated by one or more third parties as depicted in FIG. 8*e*. For instance, the emulatable aspect inclusion module 218* of the server 10 of FIG. 1*b*, the local source user device 20' of FIG. 2*b*, or the local end user device 30" of FIG. 3*b* including into at least one of the one or more personalized plans 16* at least one emulatable aspect that corresponds to at least one reported plausible aspect that is relevant to achieving the one or more target outcomes, the at least one reported plausible aspect being an aspect that has been determined to have been successfully emulated by one or more third parties 6* (e.g., other end users).

Operation 820, in turn, may further include an operation 821 for including into at least one of the one or more personalized plans at least one emulatable aspect that corresponds to at least one reported plausible aspect that is relevant to achieving the one or more target outcomes, the at least one reported plausible aspect being an aspect that has been successfully emulated by one or more third parties in order to achieve at least one of the one or more target outcomes as depicted in FIG. 8*e*. For instance, the emulatable aspect inclusion module 218* of the server 10 of FIG. 1*b*, the local source user device 20' of FIG. 2*b*, or the local end user device 30" of FIG. 3*b* including into at least one of the one or more personalized plans 16* at least one emulatable aspect that corresponds to at least one reported plausible aspect that is relevant to achieving the one or more target outcomes, the at least one reported plausible aspect being an aspect that has been successfully emulated by one or more third parties 6* (e.g., other end users) in order to achieve at least one of the one or more target outcomes.

Figure 8F:
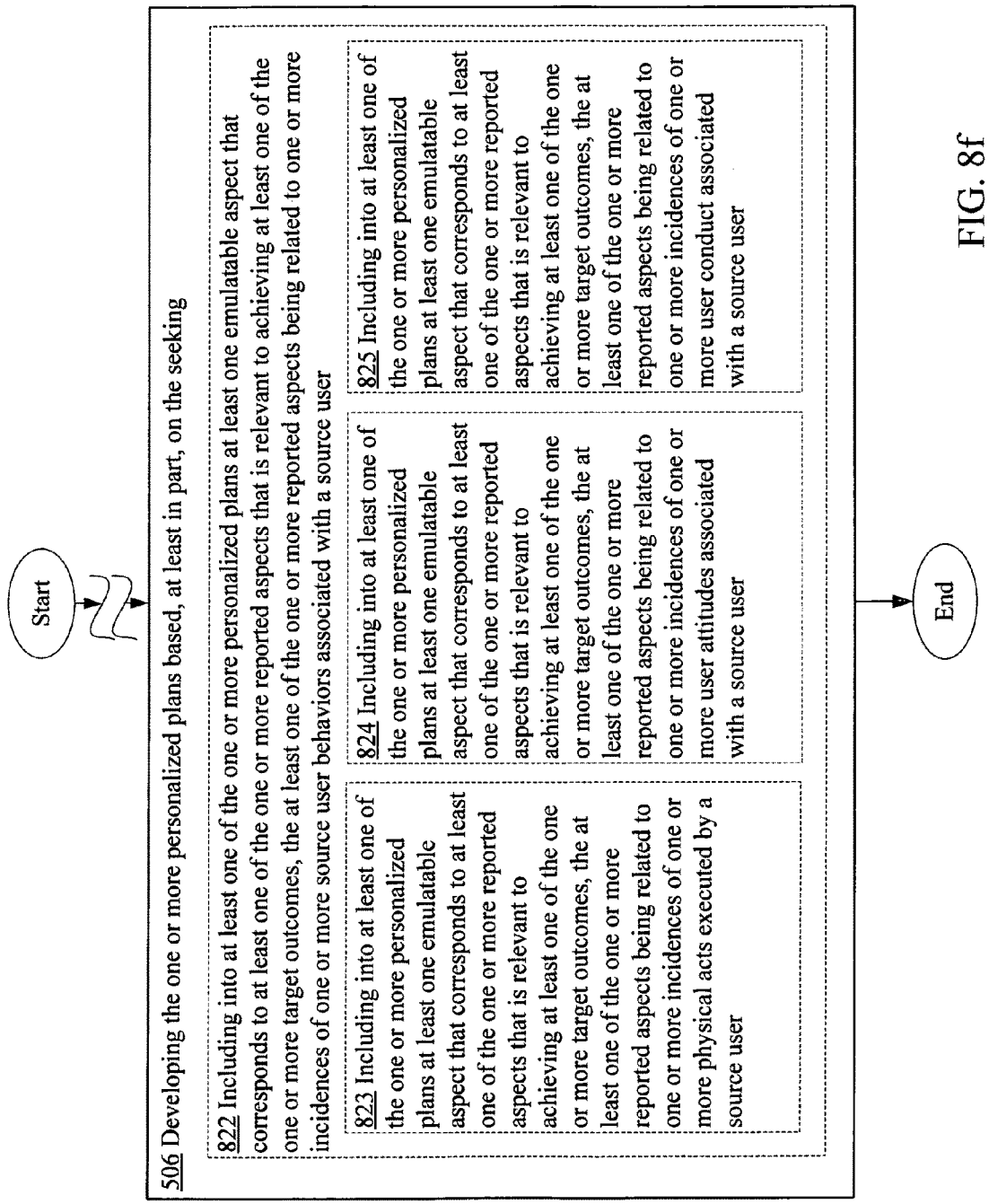
FIG. 8f is a high-level logic flowchart of a process depicting alternate implementations of the development operation 506 of FIG. 5.

In various alternative implementations, the one or more emulatable aspects that may be included into a personalized plan 16* may correspond to any one or more of a variety of different reported aspect types. For example, in various implementations, the development operation 506 of FIG. 5 may include an operation 822 for including into at least one of the one or more personalized plans at least one emulatable aspect that corresponds to at least one of the one or more reported aspects that is relevant to achieving at least one of the one or more target outcomes, the at least one of the one or more reported aspects being related to one or more incidences of one or more source user behaviors associated with a source user as depicted in FIG. 8*f*. For instance, the emulatable aspect inclusion module 218* of the server 10 of FIG. 1*b*, the local source user device 20' of FIG. 2*b*, or the local end user device 30" of FIG. 3*b* including into at least one of the one or more personalized plans 16* at least one emulatable aspect that corresponds to at least one of the one or more reported aspects 14* that is relevant to achieving at least one of the one or more target outcomes, the at least one of the one or more reported aspects 14* being related to one or more incidences of one or more source user behaviors (e.g., dietary behavior, physical activity behavior, behavior towards others, mental or physical acts, and so forth) associated with a source user (e.g., source user 2*a*\*).

Operation 822 in turn may further include one or more additional operations in various alternative implementations. For example, in some implementations, operation 822 may include an operation 823 for including into at least one of the one or more personalized plans at least one emulatable aspect that corresponds to at least one of the one or more reported aspects that is relevant to achieving at least one of the one or more target outcomes, the at least one of the one or more reported aspects being related to one or more incidences of one or more physical acts executed by a source user as depicted in FIG. 8f. For instance, the emulatable aspect inclusion module 218* of the server 10 of FIG. 1b, the local source user device 20' of FIG. 2b, or the local end user device 30" of FIG. 3b including into at least one of the one or more personalized plans 16* at least one emulatable aspect that corresponds to at least one of the one or more reported aspects 14* that is relevant to achieving at least one of the one or more target outcomes, the at least one of the one or more reported aspects 14* being related to one or more incidences of one or more physical acts (e.g., consume a food item or a medicine, attend class, read, exercise, and so forth) executed by a source user (e.g., source user 2a*).

In the same or different implementations, operation 822 may include an operation 824 for including into at least one of the one or more personalized plans at least one emulatable aspect that corresponds to at least one of the one or more reported aspects that is relevant to achieving at least one of the one or more target outcomes, the at least one of the one or more reported aspects being related to one or more incidences of one or more user attitudes associated with a source user as depicted in FIG. 8f. For instance, the emulatable aspect inclusion module 218* of the server 10 of FIG. 1b, the local source user device 20' of FIG. 2b, or the local end user device 30" of FIG. 3b including into at least one of the one or more personalized plans 16* at least one emulatable aspect that corresponds to at least one of the one or more reported aspects 14* that is relevant to achieving at least one of the one or more target outcomes, the at least one of the one or more reported aspects 14* being related to one or more incidences of one or more user attitudes (e.g., being indifferent, feeling critical, feeling skeptical, feeling optimistic, and so forth) associated with a source user (e.g., source user 2a*).

In the same or different implementations, operation 822 may include an operation 825 for including into at least one of the one or more personalized plans at least one emulatable aspect that corresponds to at least one of the one or more reported aspects that is relevant to achieving at least one of the one or more target outcomes, the at least one of the one or more reported aspects being related to one or more incidences of one or more user conduct associated with a source user as depicted in FIG. 8f. For instance, the emulatable aspect inclusion module 218* of the server 10 of FIG. 1b, the local source user device 20' of FIG. 2b, or the local end user device 30" of FIG. 3b including into at least one of the one or more personalized plans 16* at least one emulatable aspect that corresponds to at least one of the one or more reported aspects 14* that is relevant to achieving at least one of the one or more target outcomes, the at least one of the one or more reported aspects 14* being related to one or more incidences of one or more user conduct (e.g., behavior towards others, treatment of others, manner in which acts are executed, and so forth) associated with a source user (e.g., source user 2a*).

Figure 8G:
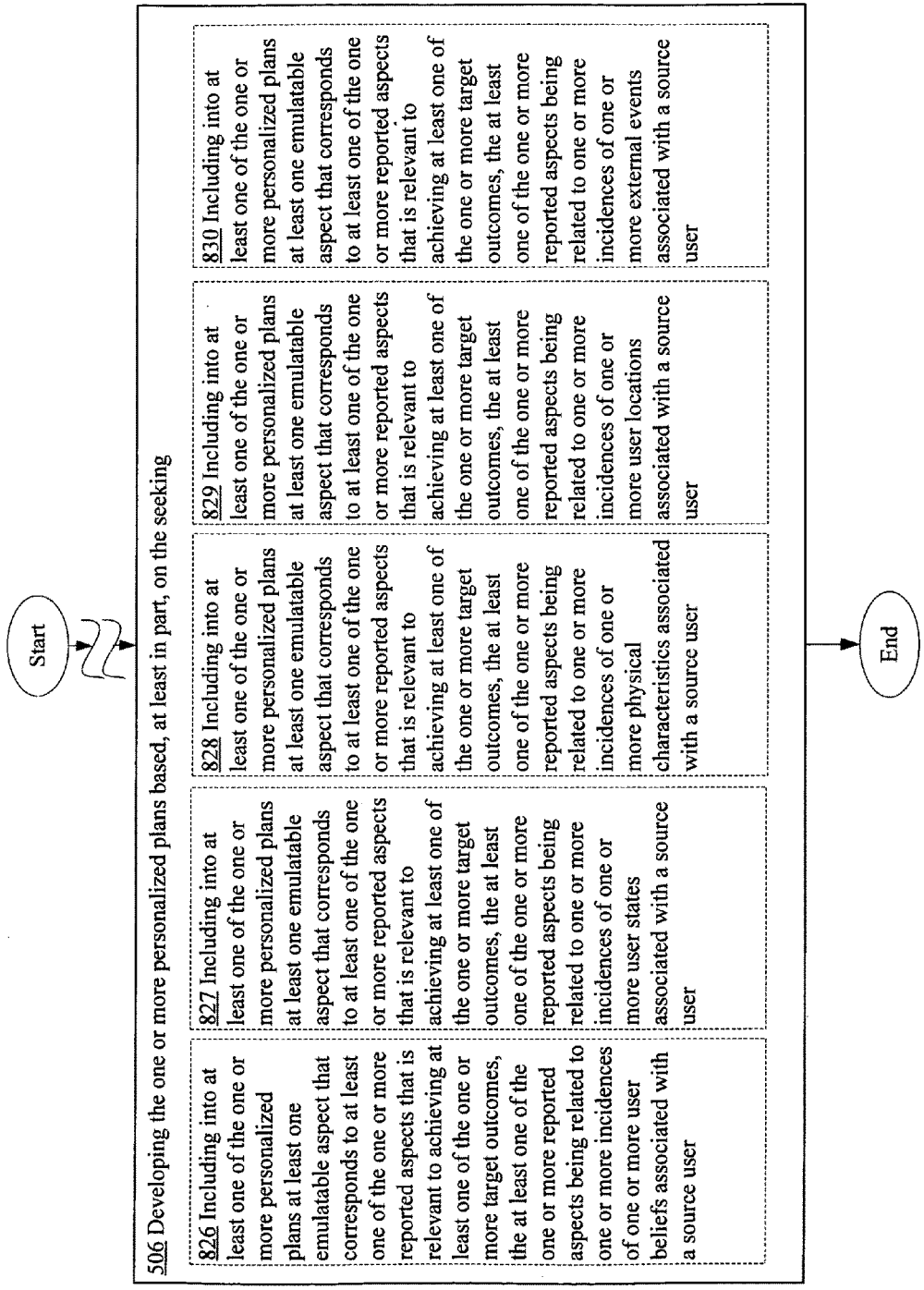
FIG. 8g is a high-level logic flowchart of a process depicting alternate implementations of the development operation 506 of FIG. 5.

In some implementations, the development operation 506 of FIG. 5 may include an operation 826 for including into at least one of the one or more personalized plans at least one emulatable aspect that corresponds to at least one of the one or more reported aspects that is relevant to achieving at least one of the one or more target outcomes, the at least one of the one or more reported aspects being related to one or more incidences of one or more user beliefs associated with a source user as depicted in FIG. 8g. For instance, the emulatable aspect inclusion module 218* of the server 10 of FIG. 1b, the local source user device 20' of FIG. 2b, or the local end user device 30" of FIG. 3b including into at least one of the one or more personalized plans 16* at least one emulatable aspect that corresponds to at least one of the one or more reported aspects 14* that is relevant to achieving at least one of the one or more target outcomes, the at least one of the one or more reported aspects 14* being related to one or more incidences of one or more user beliefs (e.g., religious beliefs, spiritual beliefs, prejudicial beliefs, and so forth) associated with a source user (e.g., source user 2a*).

In some implementations, the development operation 506 may include an operation 827 for including into at least one of the one or more personalized plans at least one emulatable aspect that corresponds to at least one of the one or more reported aspects that is relevant to achieving at least one of the one or more target outcomes, the at least one of the one or more reported aspects being related to one or more incidences of one or more user states associated with a source user as depicted in FIG. 8g. For instance, the emulatable aspect inclusion module 218* of the server 10 of FIG. 1b, the local source user device 20' of FIG. 2b, or the local end user device 30" of FIG. 3b including into at least one of the one or more personalized plans 16* at least one emulatable aspect that corresponds to at least one of the one or more reported aspects 14* that is relevant to achieving at least one of the one or more target outcomes, the at least one of the one or more reported aspects 14* being related to one or more incidences of one or more user states (e.g., mental states, marital states, employment state, physical state, availability state, and so forth) associated with a source user (e.g., source user 2a*).

In some implementations, the development operation 506 may include an operation 828 for including into at least one of the one or more personalized plans at least one emulatable aspect that corresponds to at least one of the one or more reported aspects that is relevant to achieving at least one of the one or more target outcomes, the at least one of the one or more reported aspects being related to one or more incidences of one or more physical characteristics associated with a source user as depicted in FIG. 8g. For instance, the emulatable aspect inclusion module 218* of the server 10 of FIG. 1b, the local source user device 20' of FIG. 2b, or the local end user device 30" of FIG. 3b including into at least one of the one or more personalized plans 16* at least one emulatable aspect that corresponds to at least one of the one or more reported aspects 14* that is relevant to achieving at least one of the one or more target outcomes, the at least one of the one or more reported aspects 14* being related to one or more incidences of one or more physical characteristics (e.g., hair or eye color, hair length, hair style, facial hair characteristics, overall body figure, body weight, and so forth) associated with a source user (e.g., source user 2a*).

In some implementations, the development operation 506 may include an operation 829 for including into at least one of the one or more personalized plans at least one emulatable aspect that corresponds to at least one of the one or more reported aspects that is relevant to achieving at least one of the one or more target outcomes, the at least one of the one or more reported aspects being related to one or more incidences of one or more user locations associated with a source user as depicted in FIG. 8g. For instance, the emulatable aspect inclusion module 218* of the server 10 of FIG. 1b, the local source user device 20' of FIG. 2b, or the local end user device 30" of FIG. 3b including into at least one of the one or more personalized plans 16* at least one emulatable aspect that corresponds to at least one of the one or more reported aspects 14* that is relevant to achieving at least one of the one or more target outcomes, the at least one of the one or more reported aspects 14* being related to one or more incidences of one or more user locations (e.g., home, workplace, New York City, beach, and so forth) associated with a source user (e.g., source user 2a*).

In some implementations, the development operation 506 may include an operation 830 for including into at least one of the one or more personalized plans at least one emulatable aspect that corresponds to at least one of the one or more reported aspects that is relevant to achieving at least one of the one or more target outcomes, the at least one of the one or more reported aspects being related to one or more incidences of one or more external events associated with a source user as depicted in FIG. 8g. For instance, the emulatable aspect inclusion module 218* of the server 10 of FIG. 1b, the local source user device 20' of FIG. 2b, or the local end user device 30" of FIG. 3b including into at least one of the one or more personalized plans 16* at least one emulatable aspect that corresponds to at least one of the one or more reported aspects 14* that is relevant to achieving at least one of the one or more target outcomes, the at least one of the one or more reported aspects 14* being related to one or more incidences of one or more external events (e.g., hot or cold weather, heavy or no auto traffic, and so forth) associated with a source user (e.g., source user 2a*).

Figure 8H:
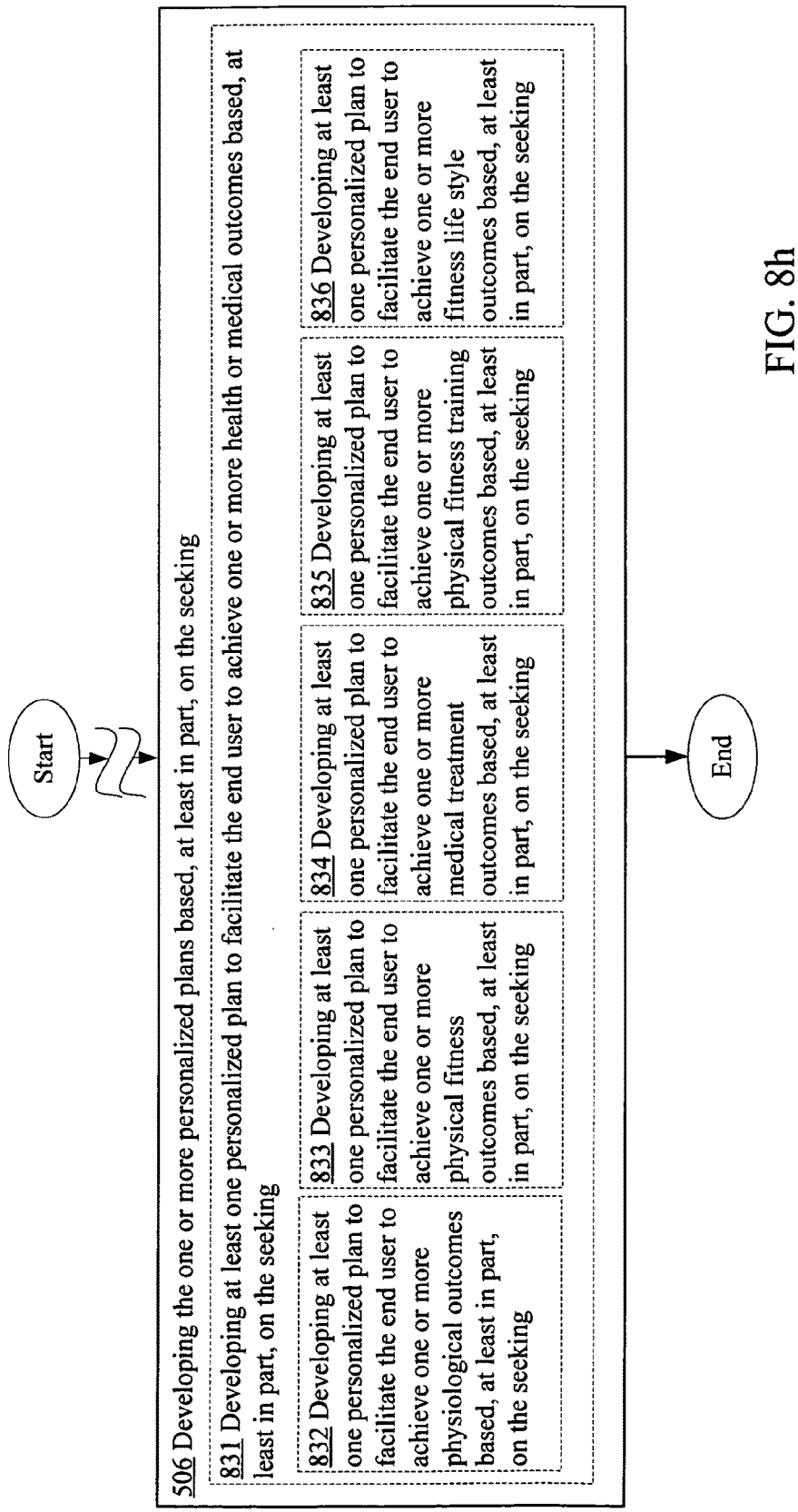
FIG. 8h is a high-level logic flowchart of a process depicting alternate implementations of the development operation 506 of FIG. 5.

The one or more personalized plans 16* to be developed through the development operation 506 of FIG. 5 may be designed to facilitate an end user 4* to achieve any one or more of a variety of different outcomes. For example, in some implementations, the development operation 506 may include an operation 831 for developing at least one personalized plan to facilitate the end user to achieve one or more health or medical outcomes based, at least in part, on the seeking as depicted in FIG. 8h. For instance, the personalized plan development module 106* of the server 10 of FIG. 1b, the local source user device 20' of FIG. 2b, or the local end user device 30" of FIG. 3b developing (e.g., creating) at least one personalized plan 16* to facilitate the end user 4* to achieve one or more health or medical outcomes (e.g., recovery time or recovery success related to an illness, weight loss, blood pressure reduction, blood glucose level reduction, lifespan, and so forth) based, at least in part, on the seeking (e.g., seeking operation 504 of FIG. 5).

The at least one personalized plan 16* to be developed through operation 831 may be to facilitate the end user 4* in achieving a variety of specific health or medical outcomes. For example, in some implementations, operation 831 may include an operation 832 for developing at least one personalized plan to facilitate the end user to achieve one or more physiological outcomes based, at least in part, on the seeking as depicted in FIG. 8h. For instance, the personalized plan development module 106* of the server 10 of FIG. 1b, the local source user device 20' of FIG. 2b, or the local end user device 30" of FIG. 3b developing at least one personalized plan 16* to facilitate the end user 4* to achieve one or more physiological outcomes (e.g., reducing blood pressure or blood glucose levels, increase red blood cell count, improve and so forth) based, at least in part, on the seeking (e.g., seeking operation 504 of FIG. 5).

In the same or different implementations, operation 831 may include an operation 833 for developing at least one personalized plan to facilitate the end user to achieve one or more physical fitness outcomes based, at least in part, on the seeking as depicted in FIG. 8h. For instance, the personalized plan development module 106* of the server 10 of FIG. 1b, the local source user device 20' of FIG. 2b, or the local end user device 30" of FIG. 3b developing at least one personalized plan 16* to facilitate the end user 4* to achieve one or more physical fitness outcomes (e.g., reduced body fat level, increased lung air capacity, reduce time it takes to run a mile, increase amount of sit-ups or push-ups, and so forth) based, at least in part, on the seeking (e.g., seeking operation 504 of FIG. 5).

In the same or different implementations, operation 831 may include an operation 834 for developing at least one personalized plan to facilitate the end user to achieve one or more medical treatment outcomes based, at least in part, on the seeking as depicted in FIG. 8h. For instance, the personalized plan development module 106* of the server 10 of FIG. 1b, the local source user device 20' of FIG. 2b, or the local end user device 30" of FIG. 3b developing at least one personalized plan 16* to facilitate the end user 4* to achieve one or more medical treatment outcomes (e.g., improved recovery from stroke or other types of disease, reduction of side-effects from a medical treatment such as chemotherapy, and so forth) based, at least in part, on the seeking (e.g., seeking operation 504 of FIG. 5).

In the same or different implementations, operation 831 may include an operation 835 for developing at least one personalized plan to facilitate the end user to achieve one or more physical fitness training outcomes based, at least in part, on the seeking as depicted in FIG. 8h. For instance, the personalized plan development module 106* of the server 10 of FIG. 1b, the local source user device 20' of FIG. 2b, or the local end user device 30" of FIG. 3b developing at least one personalized plan 16* to facilitate the end user 4* to achieve one or more physical fitness training outcomes (e.g., reduce soreness from exercising, improve results of a training program, and so forth) based, at least in part, on the seeking (e.g., seeking operation 504 of FIG. 5).

In the same or different implementations, operation 831 may include an operation 836 for developing at least one personalized plan to facilitate the end user to achieve one or more fitness life style outcomes based, at least in part, on the seeking as depicted in FIG. 8h. For instance, the personalized plan development module 106* of the server 10 of FIG. 1b, the local source user device 20' of FIG. 2b, or the local end user device 30" of FIG. 3b developing at least one personalized plan 16* to facilitate the end user 4* to achieve one or more fitness life style outcomes (e.g., quit smoking, getting regular eight hours of nightly sleep, sticking with a vegan or low carbohydrate diet, and so forth) based, at least in part, on the seeking (e.g., seeking operation 504 of FIG. 5).

Figure 8I:
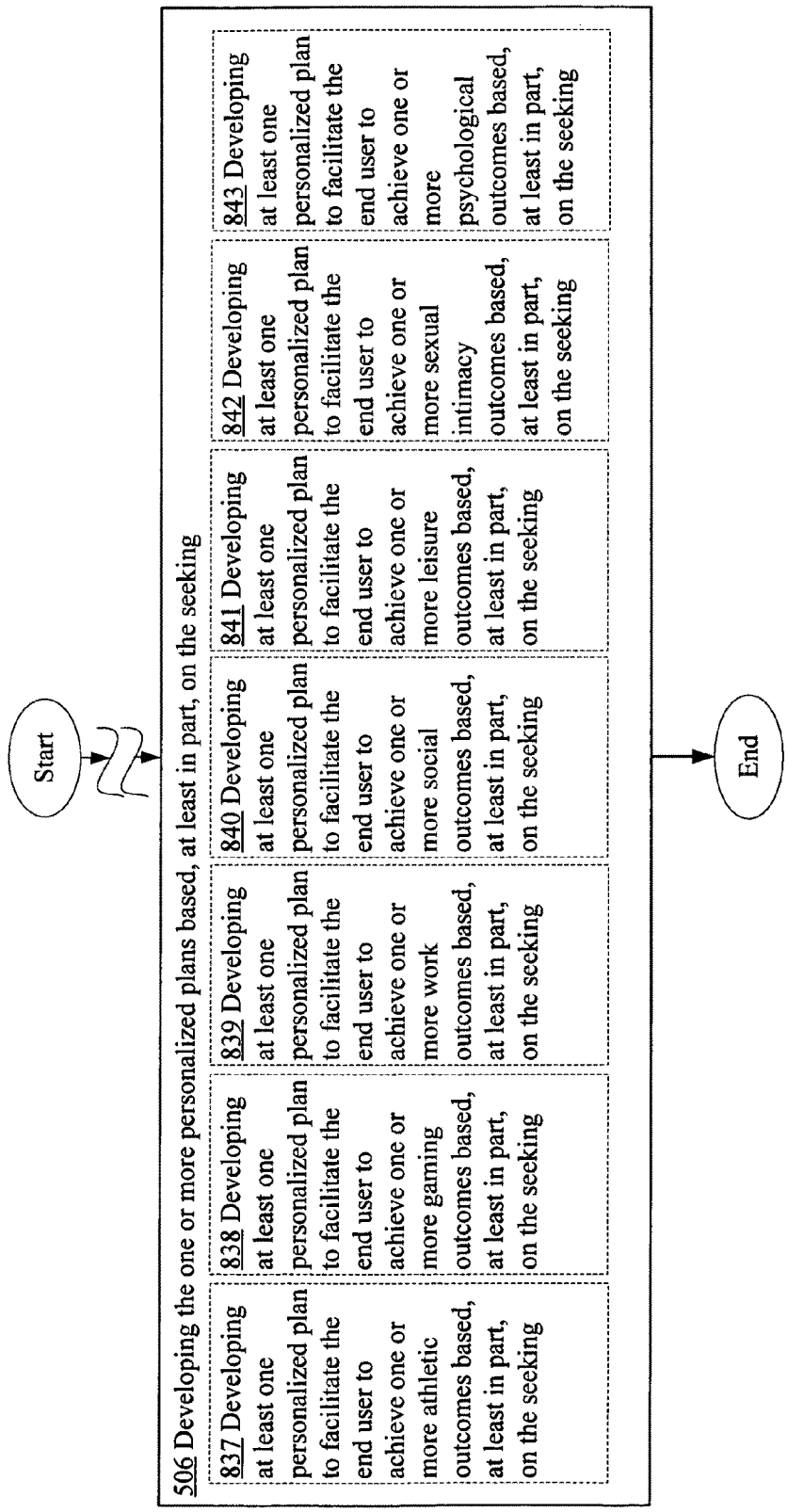
FIG. 8i is a high-level logic flowchart of a process depicting alternate implementations of the development operation 506 of FIG. 5.

In some implementations, the development operation 506 of FIG. 5 may include an operation 837 for developing at least one personalized plan to facilitate the end user to achieve one or more athletic outcomes based, at least in part, on the seeking as depicted in FIG. 8i. For instance, the personalized plan development module 106* of the server 10 of FIG. 1b, the local source user device 20' of FIG. 2b, or the local end user device 30" of FIG. 3b developing at least one personalized plan 16* to facilitate the end user 4* to achieve one or more athletic outcomes (e.g., improve golf scores, win a bicycle or swimming race, develop a curve ball pitch, and so forth) based, at least in part, on the seeking (e.g., seeking operation 504 of FIG. 5).

In some implementations, the development operation 506 of FIG. 5 may include an operation 838 for developing at least one personalized plan to facilitate the end user to achieve one or more gaming outcomes based, at least in part, on the seeking as depicted in FIG. 8i. For instance, the personalized plan development module 106* of the server 10 of FIG. 1b, the local source user device 20' of FIG. 2b, or the local end user device 30" of FIG. 3b developing at least one personalized plan 16* to facilitate the end user 4* to achieve one or more gaming outcomes (e.g., winning a chest tournament or improve video gaming skills) based, at least in part, on the seeking (e.g., seeking operation 504 of FIG. 5).

In some implementations, the development operation 506 of FIG. 5 may include an operation 839 for developing at least one personalized plan to facilitate the end user to achieve one or more work outcomes based, at least in part, on the seeking as depicted in FIG. 8i. For instance, the personalized plan development module 106* of the server 10 of FIG. 1b, the local source user device 20' of FIG. 2b, or the local end user device 30" of FIG. 3b developing at least one personalized plan 16* to facilitate the end user 4* to achieve one or more work outcomes (e.g., a job promotion, finish a project on time, and so forth) based, at least in part, on the seeking (e.g., seeking operation 504 of FIG. 5).

In some implementations, the development operation 506 of FIG. 5 may include an operation 840 for developing at least one personalized plan to facilitate the end user to achieve one or more social outcomes based, at least in part, on the seeking as depicted in FIG. 8i. For instance, the personalized plan development module 106* of the server 10 of FIG. 1b, the local source user device 20' of FIG. 2b, or the local end user device 30" of FIG. 3b developing at least one personalized plan 16* to facilitate the end user 4* to achieve one or more social outcomes (e.g., attaining a certain social class, having a dinner date with a particular person, developing a particular reputation, and so forth) based, at least in part, on the seeking (e.g., seeking operation 504 of FIG. 5).

In some implementations, the development operation 506 of FIG. 5 may include an operation 841 for developing at least one personalized plan to facilitate the end user to achieve one or more leisure outcomes based, at least in part, on the seeking as depicted in FIG. 8i. For instance, the personalized plan development module 106* of the server 10 of FIG. 1b, the local source user device 20' of FIG. 2b, or the local end user device 30" of FIG. 3b developing at least one personalized plan 16* to facilitate the end user 4* to achieve one or more leisure outcomes (e.g., learn how to knit, seeking time to go on vacation, finish reading a book, and so forth) based, at least in part, on the seeking (e.g., seeking operation 504 of FIG. 5).

In some implementations, the development operation 506 of FIG. 5 may include an operation 842 for developing at least one personalized plan to facilitate the end user to achieve one or more sexual intimacy outcomes based, at least in part, on the seeking as depicted in FIG. 8i. For instance, the personalized plan development module 106* of the server 10 of FIG. 1b, the local source user device 20' of FIG. 2b, or the local end user device 30" of FIG. 3b developing at least one personalized plan 16* to facilitate the end user 4* to achieve one or more sexual intimacy outcomes (e.g., increased sexual activities, increased sexual performance, and so forth) based, at least in part, on the seeking (e.g., seeking operation 504 of FIG. 5).

In some implementations, the development operation 506 of FIG. 5 may include an operation 843 for developing at least one personalized plan to facilitate the end user to achieve one or more psychological outcomes based, at least in part, on the seeking as depicted in FIG. 8i. For instance, the personalized plan development module 106* of the server 10 of FIG. 1b, the local source user device 20' of FIG. 2b, or the local end user device 30" of FIG. 3b developing at least one personalized plan 16* to facilitate the end user 4* to achieve one or more psychological outcomes (e.g., overcoming a phobia, overcoming certain addictive behavior such as compulsion to be clean, and so forth) based, at least in part, on the seeking (e.g., seeking operation 504 of FIG. 5).

Figure 8J:
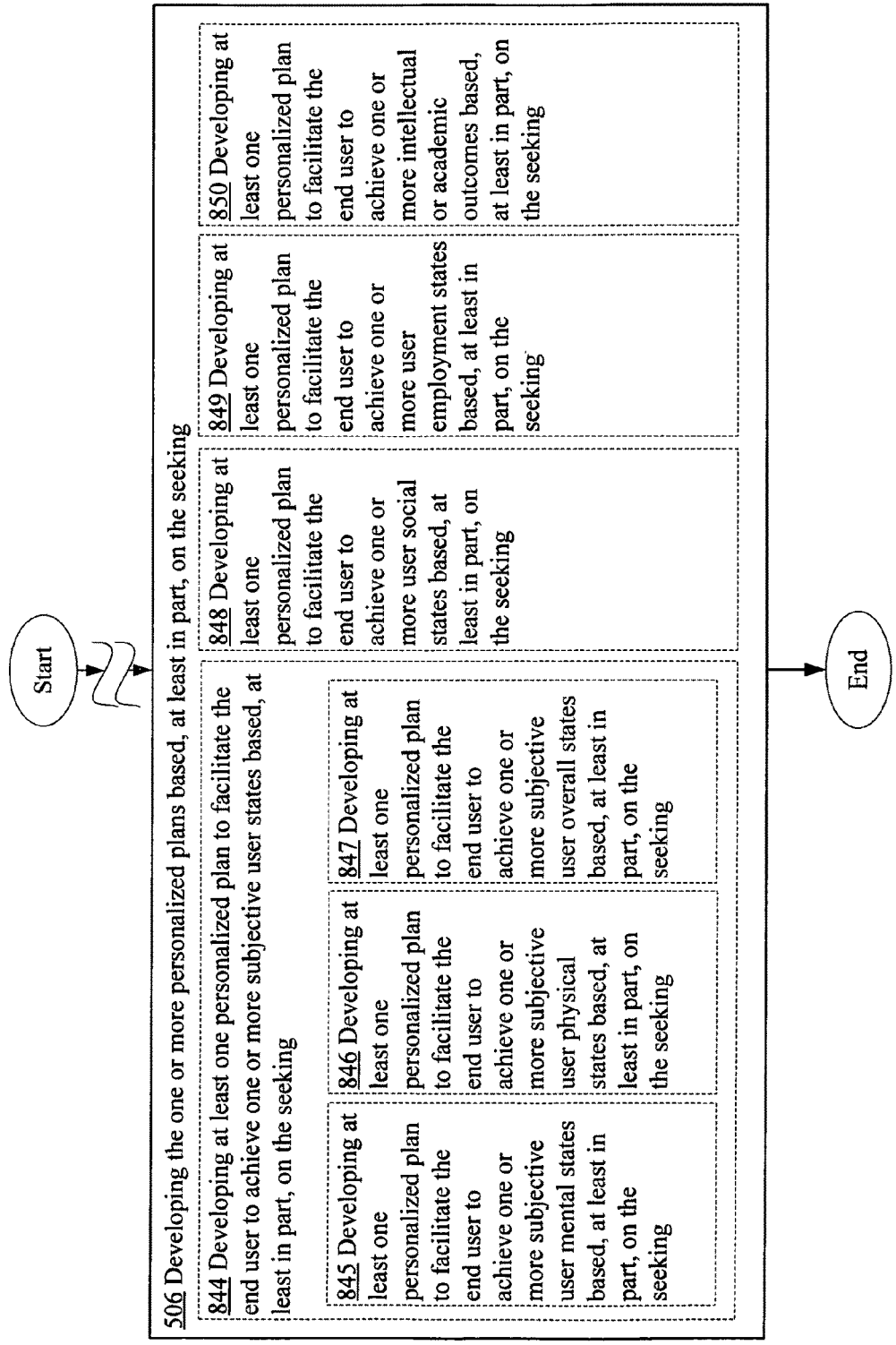
FIG. 8j is a high-level logic flowchart of a process depicting alternate implementations of the development operation 506 of FIG. 5.

In some implementations, the development operation 506 of FIG. 5 may include an operation 844 for developing at least one personalized plan to facilitate the end user to achieve one or more subjective user states based, at least in part, on the seeking as depicted in FIG. 8j. For instance, the personalized plan development module 106* of the server 10 of FIG. 1b, the local source user device 20' of FIG. 2b, or the local end user device 30" of FIG. 3b developing at least one personalized plan 16* to facilitate the end user 4* to achieve one or more subjective user states (e.g., overcoming a phobia, overcoming certain addictive behavior such as compulsion to be clean, and so forth) based, at least in part, on the seeking (e.g., seeking operation 504 of FIG. 5).

Operation 844 may further include one or more additional operations in various alternative implementations. For example, in some implementations, operation 844 may include an operation 845 for developing at least one personalized plan to facilitate the end user to achieve one or more subjective user mental states based, at least in part, on the seeking depicted in FIG. 8j. For instance, the personalized plan development module 106* of the server 10 of FIG. 1b, the local source user device 20' of FIG. 2b, or the local end user device 30" of FIG. 3b developing at least one personalized plan 16* to facilitate the end user 4* to achieve one or more subjective user mental states (e.g., happiness, alertness, clarity of thinking, calmness, and so forth) based, at least in part, on the seeking (e.g., seeking operation 504 of FIG. 5).

In some implementations, operation 844 may include an operation 846 for developing at least one personalized plan to facilitate the end user to achieve one or more subjective user physical states based, at least in part, on the seeking depicted in FIG. 8j. For instance, the personalized plan development module 106* of the server 10 of FIG. 1b, the local source user device 20' of FIG. 2b, or the local end user device 30" of FIG. 3b developing at least one personalized plan 16* to facilitate the end user 4* to achieve one or more subjective user physical states (e.g., physical fatigue, pain, blurry vision, and so forth) based, at least in part, on the seeking (e.g., seeking operation 504 of FIG. 5).

In some implementations, operation 844 may include an operation 847 for developing at least one personalized plan to facilitate the end user to achieve one or more subjective user overall states based, at least in part, on the seeking depicted in FIG. 8j. For instance, the personalized plan development module 106* of the server 10 of FIG. 1b, the local source user device 20' of FIG. 2b, or the local end user device 30" of FIG. 3b developing at least one personalized plan 16* to facilitate the end user 4* to achieve one or more subjective user overall states (e.g., "good," "bad." "well," "tired," "available," "busy," and so forth) based, at least in part, on the seeking (e.g., seeking operation 504 of FIG. 5).

In various implementations, the development operation 506 of FIG. 5 may include an operation 848 for developing at least one personalized plan to facilitate the end user to achieve one or more user social states based, at least in part, on the seeking as depicted in FIG. 8j. For instance, the personalized plan development module 106* of the server 10 of FIG. 1b, the local source user device 20' of FIG. 2b, or the local end user device 30" of FIG. 3b developing at least one personalized plan 16* to facilitate the end user 4* to achieve one or more user social states (e.g., membership to a social group, being married, being single and so forth) based, at least in part, on the seeking (e.g., seeking operation 504 of FIG. 5).

In various implementations, the development operation 506 of FIG. 5 may include an operation 849 for developing at least one personalized plan to facilitate the end user to achieve one or more user employment states based, at least in part, on the seeking as depicted in FIG. 8j. For instance, the personalized plan development module 106* of the server 10 of FIG.

1b, the local source user device 20' of FIG. 2b, or the local end user device 30" of FIG. 3b developing at least one personalized plan 16* to facilitate the end user 4* to achieve one or more user employment states (e.g., being employed, attaining a particular employment position, attaining managerial authority, and so forth) based, at least in part, on the seeking (e.g., seeking operation 504 of FIG. 5).

In various implementations, the development operation 506 of FIG. 5 may include an operation 850 for developing at least one personalized plan to facilitate the end user to achieve one or more intellectual or academic outcomes based, at least in part, on the seeking as depicted in FIG. 8j. For instance, the personalized plan development module 106* of the server 10 of FIG. 1b, the local source user device 20' of FIG. 2b, or the local end user device 30" of FIG. 3b developing at least one personalized plan 16* to facilitate the end user 4* to achieve one or more intellectual or academic outcomes (e.g., passing a particular exam or class, obtaining a certain degree or academic award, being accepted into a particular program or school, attaining a particular scholarship, understanding a complex concept, acquiring particular knowledge, and so forth) based, at least in part, on the seeking (e.g., seeking operation 504 of FIG. 5).

Figure 9:
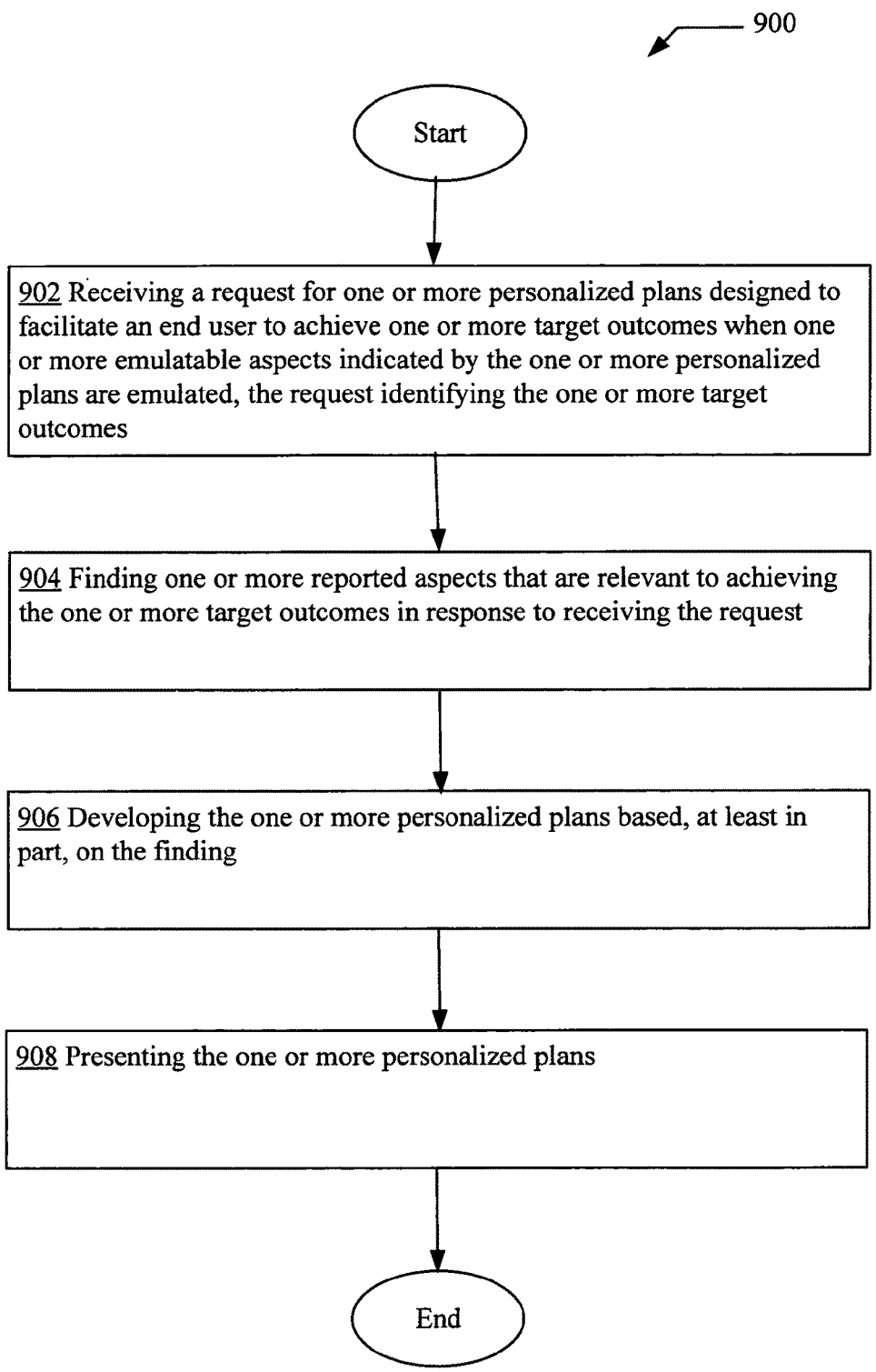
FIG. 9 is a high-level logic flowchart of another process.

Referring to FIG. 9 illustrating another operational flow 900 in accordance with various embodiments. Operational flow 900 includes certain operations that mirror the operations included in the operational flow 500 of FIG. 5. These operations include a reception operation 902, a seeking operation 904 and a development operation 906 that corresponds to and mirror the reception operation 502, the seeking operation 504 and the development operation 506, respectively, of FIG. 5.

In addition, operational flow 900 includes a presentation operation 908 for presenting the one or more personalized plans as depicted in FIG. 9. For instance, the presentation module 108* of the server 10 of FIG. 1b, the local source user device 20' of FIG. 2b, or the local end user device 30" of FIG. 3b presenting (e.g., transmitting via the wireless network and/or wired network 50* or indicating via a user interface 120*) the one or more personalized plans 16*.

Figure 10:
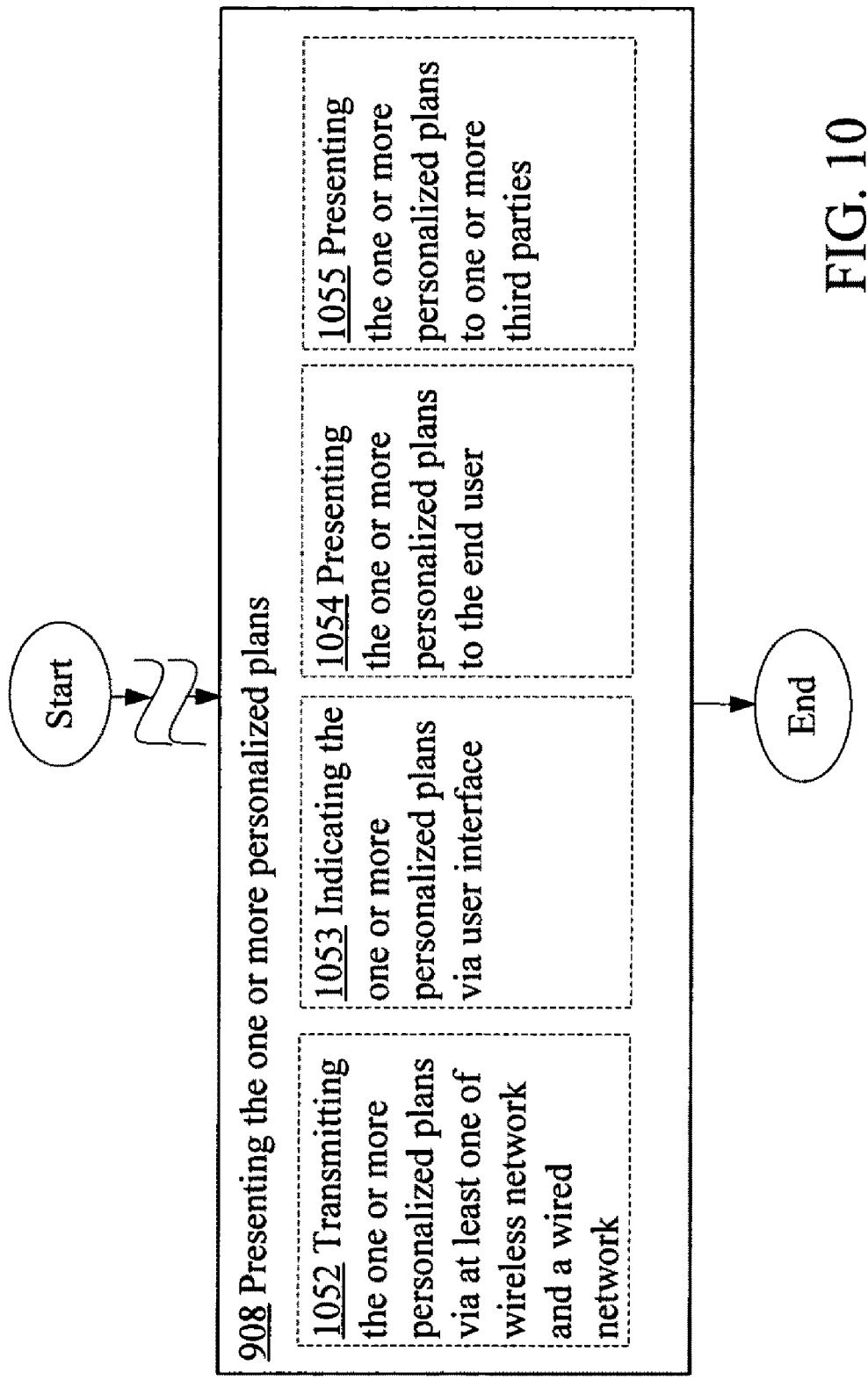
FIG. 10 is a high-level logic flowchart of a process depicting alternate implementations of the presentation operation 908 of FIG. 9.

In various alternative implementations, the presentation operation 908 may include one or more additional operations. For example, in some implementations, the presentation operation 908 may include an operation 1052 for transmitting the one or more personalized plans via at least one of wireless network and a wired network as depicted in FIG. 10. For instance, the transmission module 224* of the server 10 of FIG. 1b, the local source user device 20' of FIG. 2b, or the local end user device 30" of FIG. 3b transmitting the one or more personalized plans 16* via at least one of wireless network and a wired network 50*.

In the same or different implementations, the presentation operation 908 may include an operation 1053 for indicating the one or more personalized plans via user interface as depicted in FIG. 10. For instance, the user interface indication module 226* of the local source user device 20' of FIG. 2b or the local end user device 30" of FIG. 3b audioally or visually indicating the one or more personalized plans 16* via a user interface 120* (e.g., a display monitor, a touchscreen, an audio system including one or more speakers, and so forth).

In the same or different implementations, the presentation operation 908 may include an operation 1054 for presenting the one or more personalized plans to the end user as depicted in FIG. 10. For instance, the presentation module 108* of the server 10 of FIG. 1b, the local source user device 20' of FIG. 2b, or the local end user device 30" of FIG. 3b presenting the one or more personalized plans 16* to the end user 4*.

In the same or different implementations, the presentation operation 908 may include an operation 1055 for presenting the one or more personalized plans to one or more third parties as depicted in FIG. 10. For instance, the presentation module 108* of the server 10 of FIG. 1b, the local source user device 20' of FIG. 2b, or the local end user device 30" of FIG. 3b presenting the one or more personalized plans 16* to one or more third parties 6*.

Figure 11:
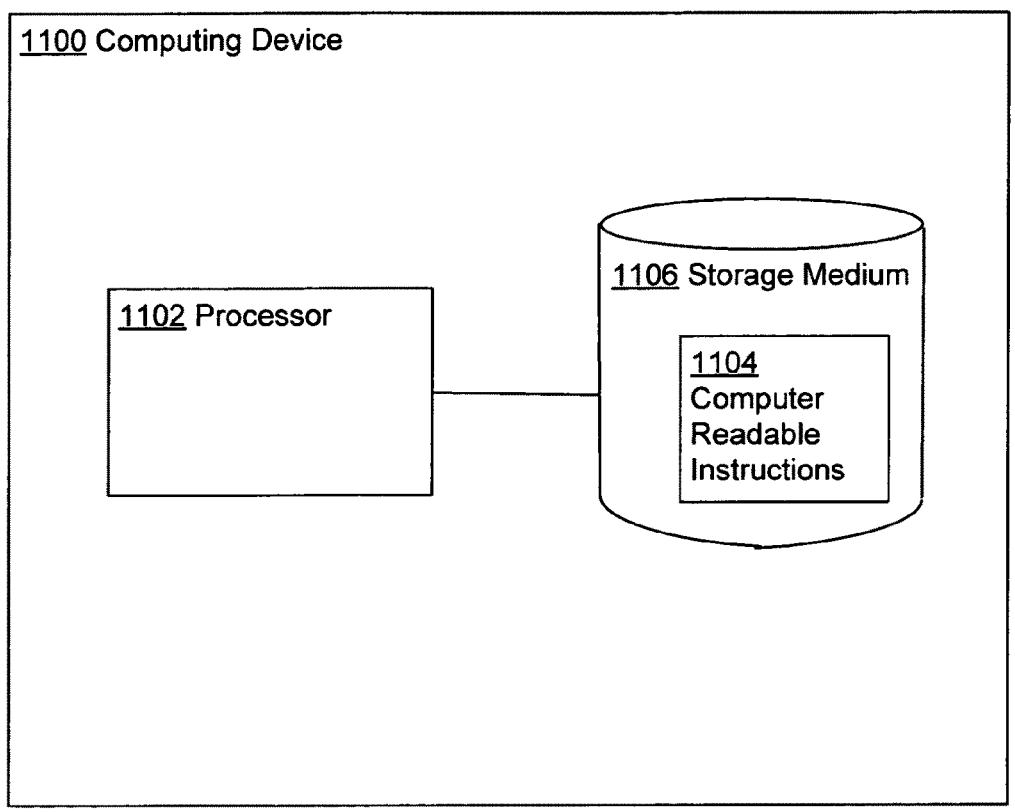
FIG. 11 is a high-level block diagram of a computing device.

Turning now to FIG. 11 illustrating a computing device 1100 designed to implement one or more of the operations of the operational flows described above (e.g., as illustrated in FIGS. 5, 6a, 6b, 6c, 6d, 6e, 6f, 7a, 7b, 7c, 7d, 7e, 7f, 7g, 7h, 7i, 7j, 7k, 7l, 7m, 8a, 8b, 8c, 8d, 8e, 8f, 8g, 8h, 8i, 8j, 9, and 10). In various implementations, the computing device 1100 may be a server such as the server 10 of FIG. 1b or a local client device such as the local source user device 20a' of FIG. 2b or the local end user device 30" of FIG. 3b.

As illustrated, the computing device 1100 may include a processor 1102 (e.g., microprocessor, controller, and so forth) coupled to storage medium 1106 (e.g., volatile or non-volatile memory). The storage medium 1106 may store computer readable instructions 1104 (e.g., computer program product). The processor 1102, in various implementations, may execute the computer readable instructions 1104 in order to execute one or more operations described above and as illustrated in FIGS. 5, 6a, 6b, 6c, 6d, 6e, 6f, 7a, 7b, 7c, 7d, 7e, 7f, 7g, 7h, 7i, 7j, 7k, 7l, 7m, 8a, 8b, 8c, 8d, 8e, 8f, 8g, 8h, 8i, 8j, 9, and 10.

For example, the processor 1102 may execute the computer readable instructions 1104 in order to receive a request for one or more personalized plans designed to facilitate an end user to achieve one or more target outcomes when one or more emulatable aspects indicated by the one or more personalized plans are emulated, the request identifying the one or more target outcomes; seek one or more reported aspects that are relevant to achieving the one or more target outcomes in response to receiving the request; and/or develop the one or more personalized plans based, at least in part, on the seeking as depicted in the operational flow 500 of FIG. 5.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuitry (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuitry, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A computationally-implemented system, comprising:
    means for receiving a request for one or more personalized plans designed to facilitate an end user to achieve one or more target outcomes when one or more emulatable aspects indicated by the one or more personalized plans are emulated, the request identifying the one or more target outcomes;
    means for seeking one or more reported aspects that are relevant to achieving the one or more target outcomes in response to receiving the request, wherein said means for seeking one or more reported aspects that are relevant to achieving the one or more target outcomes in response to receiving the request, comprises:
        means for identifying one or more reported outcomes that correspond to the one or more target outcomes to facilitate the seeking, wherein said means for identifying one or more reported outcomes that correspond to the one or more target outcomes to facilitate the seeking, comprises:
            means for identifying the one or more reported aspects that are relevant to achieving the one or more target outcomes including identifying one or more reported aspects that complies with one or more limitations associated with the end user and that are associated with the one or more reported outcomes; and
    means for developing the one or more personalized plans based, at least in part, on the seeking.

2. The computationally-implemented system of claim 1, wherein said means for receiving a request for one or more personalized plans designed to facilitate an end user to achieve one or more target outcomes when one or more emulatable aspects indicated by the one or more personalized plans are emulated, the request identifying the one or more target outcomes, comprises:
    means for receiving the request for the one or more personalized plans, the request including one or more identifiers associated with the one or more target outcomes.

3. The computationally-implemented system of claim 1, wherein said means for receiving a request for one or more personalized plans designed to facilitate an end user to achieve one or more target outcomes when one or more emulatable aspects indicated by the one or more personalized plans are emulated, the request identifying the one or more target outcomes, comprises:
    means for receiving the request for the one or more personalized plans, the request not identifying any source user.

4. The computationally-implemented system of claim 1, wherein said means for receiving a request for one or more personalized plans designed to facilitate an end user to achieve one or more target outcomes when one or more emulatable aspects indicated by the one or more personalized plans are emulated, the request identifying the one or more target outcomes, comprises:
    means for receiving the request for the one or more personalized plans, the request identifying one or more source user groups.

5. The computationally-implemented system of claim 4, wherein said means for receiving the request for the one or more personalized plans, the request identifying one or more source user groups, comprises:
    means for receiving the request for the one or more personalized plans, the request identifying one or more source user groups that share at least one common trait with the end user.

6. The computationally-implemented system of claim 1, wherein said means for receiving a request for one or more personalized plans designed to facilitate an end user to achieve one or more target outcomes when one or more emulatable aspects indicated by the one or more personalized plans are emulated, the request identifying the one or more target outcomes, comprises:
    means for receiving the request for the one or more personalized plans, the request indicating one or more preferences of the end user.

7. The computationally-implemented system of claim 1, wherein said means for receiving a request for one or more personalized plans designed to facilitate an end user to achieve one or more target outcomes when one or more emulatable aspects indicated by the one or more personalized plans are emulated, the request identifying the one or more target outcomes, comprises:
    means for receiving the request for the one or more personalized plans, the request indicating one or more limitations associated with the end user.

8. The computationally-implemented system of claim 7, wherein said means for receiving the request for the one or more personalized plans, the request indicating one or more limitations associated with the end user, comprises:
    means for receiving the request for the one or more personalized plans, the request indicating one or more physical limitations associated with the end user.

9. The computationally-implemented system of claim 7, wherein said means for receiving the request for the one or more personalized plans, the request indicating one or more limitations associated with the end user, comprises:
 means for receiving the request for the one or more personalized plans, the request indicating one or more contextual limitations associated with the end user.

10. The computationally-implemented system of claim 7, wherein said means for receiving the request for the one or more personalized plans, the request indicating one or more limitations associated with the end user, comprises:
 means for receiving the request for the one or more personalized plans, the request indicating one or more personal limitations associated with the end user.

11. The computationally-implemented system of claim 7, wherein said means for receiving the request for the one or more personalized plans, the request indicating one or more limitations associated with the end user, comprises:
 means for receiving the request for the one or more personalized plans, the request indicating one or more medical or health limitations associated with the end user.

12. The computationally-implemented system of claim 7, wherein said means for receiving the request for the one or more personalized plans, the request indicating one or more limitations associated with the end user, comprises:
 means for receiving the request for the one or more personalized plans, the request indicating one or more user state limitations associated with the end user.

13. The computationally-implemented system of claim 7, wherein said means for receiving the request for the one or more personalized plans, the request indicating one or more limitations associated with the end user, comprises:
 means for receiving the request for the one or more personalized plans, the request indicating one or more legal or regulatory limitations associated with the end user.

14. The computationally-implemented system of claim 1, wherein said means for seeking one or more reported aspects that are relevant to achieving the one or more target outcomes in response to receiving the request, comprises:
 means for seeking the one or more reported aspects that are relevant to achieving the one or more target outcomes by seeking one or more reported aspects that were at least originally reported through one or more log entries.

15. The computationally-implemented system of claim 14, wherein said means for seeking the one or more reported aspects that are relevant to achieving the one or more target outcomes by seeking one or more reported aspects that were at least originally reported through one or more log entries, comprises:
 means for seeking the one or more reported aspects that are relevant to achieving the one or more target outcomes by seeking one or more reported aspects that were at least originally reported through one or more social networking entries.

16. The computationally-implemented system of claim 15, wherein said means for seeking the one or more reported aspects that are relevant to achieving the one or more target outcomes by seeking one or more reported aspects that were at least originally reported through one or more social networking entries, comprises:
 means for seeking the one or more reported aspects that are relevant to achieving the one or more target outcomes by seeking one or more reported aspects that were at least originally reported through one or more blog entries.

17. The computationally-implemented system of claim 15, wherein said means for seeking the one or more reported aspects that are relevant to achieving the one or more target outcomes by seeking one or more reported aspects that were at least originally reported through one or more social networking entries, comprises:
 means for seeking the one or more reported aspects that are relevant to achieving the one or more target outcomes by seeking one or more reported aspects that were at least originally reported through one or more status reports.

18. The computationally-implemented system of claim 14, wherein said means for seeking the one or more reported aspects that are relevant to achieving the one or more target outcomes by seeking one or more reported aspects that were at least originally reported through one or more log entries, comprises:
 means for seeking the one or more reported aspects that are relevant to achieving the one or more target outcomes by seeking one or more reported aspects that were at least originally reported through one or more diary entries.

19. The computationally-implemented system of claim 14, wherein said means for seeking the one or more reported aspects that are relevant to achieving the one or more target outcomes by seeking one or more reported aspects that were at least originally reported through one or more log entries, comprises:
 means for seeking the one or more reported aspects that are relevant to achieving the one or more target outcomes by seeking one or more reported aspects that were at least originally reported through one or more log entries as provided by one or more sensors.

20. The computationally-implemented system of claim 1, wherein said means for identifying one or more reported outcomes that correspond to the one or more target outcomes to facilitate the seeking, comprises:
 means for identifying the one or more reported aspects that are relevant to achieving the one or more target outcomes including identifying the one or more reported aspects that indicates one or more aspects that occurred within one or more predefined time periods, respectively, from one or more occurrences of the one or more reported outcomes.

21. The computationally-implemented system of claim 20, wherein said means for identifying the one or more reported aspects that are relevant to achieving the one or more target outcomes including identifying the one or more reported aspects that indicates one or more aspects that occurred within one or more predefined time periods, respectively, from one or more occurrences of the one or more reported outcomes, comprises:
 means for identifying the one or more reported aspects that are relevant to achieving the one or more target outcomes including identifying the one or more reported aspects that indicates one or more aspects that occurred prior to and within one or more predefined time periods, respectively, from one or more occurrences of the one or more reported outcomes.

22. The computationally-implemented system of claim 1, wherein said means for identifying one or more reported outcomes that correspond to the one or more target outcomes to facilitate the seeking, comprises:
 means for identifying the one or more reported aspects that are relevant to achieving the one or more target outcomes including identifying one or more reported aspects that are particularly associated with a source user who is also associated with the one or more reported outcomes.

23. The computationally-implemented system of claim 1, wherein said means for identifying one or more reported outcomes that correspond to the one or more target outcomes to facilitate the seeking, comprises:

means for identifying the one or more reported aspects that are relevant to achieving the one or more target outcomes including identifying one or more reported aspects that are particularly associated with one or more members of a source user group, the one or more members of the source user group having at least one common trait and being further associated with the one or more reported outcomes.

24. The computationally-implemented system of claim 23, wherein said means for identifying the one or more reported aspects that are relevant to achieving the one or more target outcomes including identifying one or more reported aspects that are particularly associated with one or more members of a source user group, the one or more members of the source user group having at least one common trait and being further associated with the one or more reported outcomes, comprises:

means for identifying the one or more reported aspects that are relevant to achieving the one or more target outcomes including identifying one or more reported aspects that are particularly associated with one or more members of a social networking group, the one or more members being further associated with the one or more reported outcomes.

25. The computationally-implemented system of claim 23, wherein said means for identifying the one or more reported aspects that are relevant to achieving the one or more target outcomes including identifying one or more reported aspects that are particularly associated with one or more members of a source user group, the one or more members of the source user group having at least one common trait and being further associated with the one or more reported outcomes, comprises:

means for identifying the one or more reported aspects that are relevant to achieving the one or more target outcomes including identifying one or more reported aspects that are particularly associated with one or more members of an ethnic, religious, or social group, the one or more members being further associated with the one or more reported outcomes.

26. The computationally-implemented system of claim 23, wherein said means for identifying the one or more reported aspects that are relevant to achieving the one or more target outcomes including identifying one or more reported aspects that are particularly associated with one or more members of a source user group, the one or more members of the source user group having at least one common trait and being further associated with the one or more reported outcomes, comprises:

means for identifying the one or more reported aspects that are relevant to achieving the one or more target outcomes including identifying one or more reported aspects that are particularly associated with one or more members of a gender or age group, the one or more members being further associated with the one or more reported outcomes.

27. The computationally-implemented system of claim 23, wherein said means for identifying the one or more reported aspects that are relevant to achieving the one or more target outcomes including identifying one or more reported aspects that are particularly associated with one or more members of a source user group, the one or more members of the source user group having at least one common trait and being further associated with the one or more reported outcomes, comprises:

means for identifying the one or more reported aspects that are relevant to achieving the one or more target outcomes including identifying one or more reported aspects that are particularly associated with one or more members of a health-related group, the one or more members being further associated with the one or more reported outcomes.

28. The computationally-implemented system of claim 23, wherein said means for identifying the one or more reported aspects that are relevant to achieving the one or more target outcomes including identifying one or more reported aspects that are particularly associated with one or more members of a source user group, the one or more members of the source user group having at least one common trait and being further associated with the one or more reported outcomes, comprises:

means for identifying the one or more reported aspects that are relevant to achieving the one or more target outcomes including identifying one or more reported aspects that are particularly associated with one or more members of an educational or academic group, the one or more members being further associated with the one or more reported outcomes.

29. The computationally-implemented system of claim 23, wherein said means for identifying the one or more reported aspects that are relevant to achieving the one or more target outcomes including identifying one or more reported aspects that are particularly associated with one or more members of a source user group, the one or more members of the source user group having at least one common trait and being further associated with the one or more reported outcomes, comprises:

means for identifying the one or more reported aspects that are relevant to achieving the one or more target outcomes including identifying one or more reported aspects that are particularly associated with one or more members of a fitness or athletic group, the one or more members being further associated with the one or more reported outcomes.

30. The computationally-implemented system of claim 23, wherein said means for identifying the one or more reported aspects that are relevant to achieving the one or more target outcomes including identifying one or more reported aspects that are particularly associated with one or more members of a source user group, the one or more members of the source user group having at least one common trait and being further associated with the one or more reported outcomes, comprises:

means for identifying the one or more reported aspects that are relevant to achieving the one or more target outcomes including identifying one or more reported aspects that are particularly associated with one or more members of a social status group, the one or more members being further associated with the one or more reported outcomes.

31. The computationally-implemented system of claim 23, wherein said means for identifying the one or more reported aspects that are relevant to achieving the one or more target outcomes including identifying one or more reported aspects that are particularly associated with one or more members of a source user group, the one or more members of the source user group having at least one common trait and being further associated with the one or more reported outcomes, comprises:

means for identifying the one or more reported aspects that are relevant to achieving the one or more target outcomes including identifying one or more reported aspects that are particularly associated with one or more members of a work or employment group, the one or more members being further associated with the one or more reported outcomes.

32. The computationally-implemented system of claim 1, wherein said means for identifying one or more reported outcomes that correspond to the one or more target outcomes to facilitate the seeking, comprises:
means for identifying the one or more reported aspects that are relevant to achieving the one or more target outcomes including identifying one or more reported aspects that complies with one or more preferences of the end user and that are associated with the one or more reported outcomes.

33. The computationally-implemented system of claim 1, wherein said means for identifying one or more reported outcomes that correspond to the one or more target outcomes to facilitate the seeking, comprises:
means for identifying the one or more reported aspects that are relevant to achieving the one or more target outcomes including identifying one or more reported plausible aspects that are associated with the one or more reported outcomes that corresponds to the one or more target outcomes, the one or more reported plausible aspects being aspects that have been successfully emulated by one or more third parties.

34. The computationally-implemented system of claim 33, wherein said means for identifying the one or more reported aspects that are relevant to achieving the one or more target outcomes including identifying one or more reported plausible aspects that are associated with the one or more reported outcomes that corresponds to the one or more target outcomes, the one or more reported plausible aspects being aspects that have been successfully emulated by one or more third parties, comprises:
means for identifying the one or more reported aspects that are relevant to achieving the one or more target outcomes including identifying one or more reported plausible aspects that are associated with the one or more reported outcomes that corresponds to the one or more target outcomes, the one or more reported plausible aspects being aspects that have been successfully emulated by the one or more third parties in order to achieve at least one of the one or more target outcomes.

35. The computationally-implemented system of claim 1, wherein said means for developing the one or more personalized plans based, at least in part, on the seeking, comprises:
means for developing the one or more personalized plans based, at least in part, on the one or more reported aspects that are relevant to achieving at least one of the one or more target outcomes and that are particularly associated with one or more members of a source user group.

36. The computationally-implemented system of claim 1, wherein said means for developing the one or more personalized plans based, at least in part, on the seeking, comprises:
means for including into each of the one or more personalized plans one or more emulatable aspects that corresponds to the one or more reported aspects that are relevant to the achievement of the one or more target outcomes.

37. The computationally-implemented system of claim 1, wherein said means for developing the one or more personalized plans based, at least in part, on the seeking, comprises:
means for including into the one or more personalized plans one or more emulatable aspects that corresponds to the one or more reported aspects that are relevant to achieving the one or more target outcomes and that complies with one or more preferences of the end user.

38. The computationally-implemented system of claim 1, wherein said means for developing the one or more personalized plans based, at least in part, on the seeking, comprises:
means for including into the one or more personalized plans one or more emulatable aspects that corresponds to the one or more reported aspects that are relevant to achieving the one or more target outcomes and that complies with one or more limitations associated with the end user.

39. The computationally-implemented system of claim 1, wherein said means for developing the one or more personalized plans based, at least in part, on the seeking, comprises:
means for including into at least one of the one or more personalized plans at least one emulatable aspect that corresponds to at least one reported plausible aspect that is relevant to achieving the one or more target outcomes, the at least one reported plausible aspect being an aspect that has been successfully emulated by one or more third parties.

40. The computationally-implemented system of claim 1, further comprising:
means for presenting the one or more personalized plans.

41. A method for developing one or more personalized plans, comprising:
receiving a request for one or more personalized plans designed to facilitate an end user to achieve one or more target outcomes when one or more emulatable aspects indicated by the one or more personalized plans are emulated, the request identifying the one or more target outcomes;
seeking, by electrical circuitry, one or more reported aspects that are relevant to achieving the one or more target outcomes in response to receiving the request, wherein said seeking, by electrical circuitry, one or more reported aspects that are relevant to achieving the one or more target outcomes in response to receiving the request, comprises:
identifying one or more reported outcomes that correspond to the one or more target outcomes to facilitate the seeking, wherein said identifying one or more reported outcomes that correspond to the one or more target outcomes to facilitate the seeking, comprises:
identifying the one or more reported aspects that are relevant to achieving the one or more target outcomes including identifying one or more reported aspects that complies with one or more limitations associated with the end user and that are associated with the one or more reported outcomes; and
developing the one or more personalized plans based, at least in part, on the seeking.

42. A server, comprising:
a request reception module configured to receive a request for one or more personalized plans designed to facilitate an end user to achieve one or more target outcomes when one or more emulatable aspects indicated by the one or more personalized plans are emulated, the request identifying the one or more target outcomes;
a reported aspect seeking module configured to seek one or more reported aspects that are relevant to achieving the one or more target outcomes in response to receiving the request, wherein said reported aspect seeking module configured to seek one or more reported aspects that are relevant to achieving the one or more target outcomes in response to receiving the request comprises:

a reported outcome identification module configured to identify one or more reported outcomes that correspond to the one or more target outcomes to facilitate the seeking, wherein said reported outcome identification module configured to identify one or more reported outcomes that correspond to the one or more target outcomes to facilitate the seeking comprises
a limitation compliant reported aspect identification module configured to identify the one or more reported aspects that are relevant to achieving the one or more target outcomes including identifying one or more reported aspects that complies with one or more limitations associated with the end user and that are associated with the one or more reported outcomes;
a personalized plan development module configured to develop the one or more personalized plans based, at least in part, on the seeking; and
a memory.

* * * * *